US012569592B2

(12) United States Patent
Ayares

(10) Patent No.: US 12,569,592 B2
(45) Date of Patent: *Mar. 10, 2026

(54) GENETICALLY MODIFIED PIGS FOR XENOTRANSPLANTATION OF VASCULARIZED XENOGRAFTS AND DERIVATIVES THEREOF

(71) Applicant: Revivicor, Inc.

(72) Inventor: David Ayares, Blacksburg, VA (US)

(73) Assignee: Revivicor, Inc., Blacksburg, VA (US)

( * ) Notice: Subject to any disclaimer, the term of this patent is extended or adjusted under 35 U.S.C. 154(b) by 1122 days.

This patent is subject to a terminal disclaimer.

(21) Appl. No.: 17/532,893

(22) Filed: Nov. 22, 2021

(65) Prior Publication Data

US 2022/0072200 A1 Mar. 10, 2022

Related U.S. Application Data

(63) Continuation of application No. 13/966,121, filed on Aug. 13, 2013, now Pat. No. 11,179,496, which is a continuation of application No. PCT/US2012/025097, filed on Feb. 14, 2012.

(60) Provisional application No. 61/442,504, filed on Feb. 14, 2011.

(51) Int. Cl.
| | |
|---|---|
| *A61L 27/36* | (2006.01) |
| *A01K 67/0271* | (2024.01) |
| *A01K 67/0275* | (2024.01) |
| *A01K 67/0278* | (2024.01) |
| *A61K 45/06* | (2006.01) |
| *C12N 15/85* | (2006.01) |

(52) U.S. Cl.
CPC ...... *A61L 27/3604* (2013.01); *A01K 67/0271* (2013.01); *A01K 67/0275* (2013.01); *A01K 67/0278* (2013.01); *A61K 45/06* (2013.01); *C12N 15/8509* (2013.01); *A01K 2217/052* (2013.01); *A01K 2217/075* (2013.01); *A01K 2227/108* (2013.01); *A01K 2267/02* (2013.01)

(58) Field of Classification Search
None
See application file for complete search history.

(56) References Cited

U.S. PATENT DOCUMENTS

| | | | |
|---|---|---|---|
| 4,736,866 | A | 4/1988 | Leder et al. |
| 4,873,191 | A | 10/1989 | Wagner et al. |
| 4,888,274 | A | 12/1989 | Radding et al. |
| 4,944,384 | A | 7/1990 | Herron |
| 5,057,420 | A | 10/1991 | Massey |
| 5,334,575 | A | 8/1994 | Noonan et al. |
| 5,453,457 | A | 9/1995 | Meltzer et al. |
| 5,496,720 | A | 3/1996 | Susko-Parrish et al. |
| 5,523,226 | A | 6/1996 | Wheeler |
| 5,730,403 | A | 3/1998 | Johnson |
| 5,747,340 | A | 5/1998 | Harats et al. |
| 5,821,117 | A | 10/1998 | Sandrin et al. |
| 5,859,307 | A | 1/1999 | Mombaerts et al. |
| 5,945,577 | A | 8/1999 | Stice et al. |
| 5,977,318 | A | 11/1999 | Linsley et al. |
| 6,066,725 | A | 5/2000 | DeBoer et al. |
| 6,147,276 | A | 11/2000 | Campbell et al. |
| 6,153,428 | A | 11/2000 | Gustafsson et al. |
| 6,166,288 | A | 12/2000 | Diamond et al. |
| 6,215,041 | B1 | 4/2001 | Stice et al. |
| 6,235,969 | B1 | 5/2001 | Stice et al. |
| 6,252,133 | B1 | 6/2001 | Campbell et al. |
| 6,258,998 | B1 | 7/2001 | Damiani et al. |
| 6,376,743 | B1 | 4/2002 | Yanagimachi |
| 6,413,769 | B1 | 7/2002 | Gustafsson et al. |
| 6,423,316 | B1 | 7/2002 | Riesbeck et al. |
| 6,506,559 | B1 | 1/2003 | Fire et al. |
| 6,525,243 | B1 | 2/2003 | Stockman Campbell et al. |
| 6,548,741 | B2 | 4/2003 | Desousa et al. |
| 6,573,099 | B2 | 6/2003 | Graham |
| 6,639,122 | B1 | 10/2003 | Tu et al. |
| 6,872,868 | B1 | 3/2005 | Wagner et al. |
| 7,304,033 | B2 | 12/2007 | Larsen et al. |
| 7,368,284 | B2 | 5/2008 | Koike |
| 7,378,569 | B2 | 5/2008 | Tu et al. |
| 7,462,466 | B2 | 12/2008 | Morgan et al. |

(Continued)

FOREIGN PATENT DOCUMENTS

| | | |
|---|---|---|
| CN | 1582332 | 2/2005 |
| CN | 108949832 A | 12/2018 |

(Continued)

OTHER PUBLICATIONS

D'Apice et al. Xenotransplantation: The Next Generation of Engineered Animals. Transplant Immunology, 2009. 21:111-115.*
Fisicaro et al. Efficient Co-Expression of Multiple Graft-Protective Transgenes Using The 2A System. Xenotransplantation 2007; 14(4):383.*
Cooper et al., "Clinical lung xenotransplantation—what donor genetic modifications may be necessary?", Xenotransplantation, 2012, 19:144-158.
Li et al., "Rosa26-targeted swine models for stable gene over-expression and Cre-mediated lineage tracing," Cell Research, 2014, 24:501-504.
Mohiuddin et al., "Chimeric 2C1OR4 anti-CD40 antibody therapy is critical for long-term survival of GTKO.ACD46.hTBM pig-to-primate cardiac xenograft," Nature Communications, vol. 7:11138, Apr. 5, 2016, pp. 1-10.

(Continued)

*Primary Examiner* — Christopher M Babic
*Assistant Examiner* — Kimberly A Aron
(74) *Attorney, Agent, or Firm* — Foley & Lardner LLP

(57) ABSTRACT

The present invention provides certain donor animals, tissues and cells that are particularly useful for xenotransplantation therapies. In particular, the invention includes porcine animals, as well as tissue and cells derived from these, which lack any expression of functional alpha 1,3 galactosyltransferase (aGT) and express one or more additional transgenes which make these animals suitable donors for xenotransplantation of vascularized xenografts and derivatives thereof. Methods of treatment and using organs, tissues and cells derived from such animals are also provided.

18 Claims, 6 Drawing Sheets

Specification includes a Sequence Listing.

(56)                    References Cited

U.S. PATENT DOCUMENTS

| | | | |
|---|---|---|---|
| 7,755,462 | B2 | 7/2010 | Fullerton et al. |
| 2001/0044937 | A1 | 11/2001 | Schatten et al. |
| 2002/0062492 | A1 | 5/2002 | Lubon et al. |
| 2002/0068713 | A1 | 6/2002 | Rade et al. |
| 2002/0108132 | A1 | 8/2002 | Rapp |
| 2003/0014770 | A1 | 1/2003 | Gustafsson et al. |
| 2005/0155095 | A1 | 7/2005 | Koike |
| 2005/0223418 | A1 | 10/2005 | Koike |
| 2006/0068479 | A1 | 3/2006 | Koike |
| 2007/0113297 | A1 | 5/2007 | Yang et al. |
| 2007/0286845 | A1 | 12/2007 | Harats et al. |
| 2009/0186097 | A1 | 7/2009 | Ayares |
| 2013/0347134 | A1 | 12/2013 | Diacovo et al. |
| 2014/0017215 | A1 | 1/2014 | Ayares |
| 2015/0106962 | A1 | 4/2015 | Sachs et al. |
| 2018/0249688 | A1 | 9/2018 | Ayares et al. |
| 2021/0392863 | A1 | 12/2021 | Kim et al. |

FOREIGN PATENT DOCUMENTS

| | | |
|---|---|---|
| WO | WO-90/03432 | 4/1990 |
| WO | WO-94/21799 | 9/1994 |
| WO | WO-94/24274 | 10/1994 |
| WO | WO-94/26884 | 11/1994 |
| WO | WO-95/20661 | 8/1995 |
| WO | WO-95/28412 | 10/1995 |
| WO | WO-97/07668 | 3/1997 |
| WO | WO-97/07669 | 3/1997 |
| WO | WO-98/07841 | 2/1998 |
| WO | WO-98/15626 A2 | 4/1998 |
| WO | WO-98/30683 | 7/1998 |
| WO | WO-99/07829 | 2/1999 |
| WO | WO-99/49029 | 9/1999 |
| WO | WO-99/53042 | 10/1999 |
| WO | WO-99/57266 | 11/1999 |
| WO | WO-00/04217 | 1/2000 |
| WO | WO-00/22098 | 4/2000 |
| WO | WO-00/31126 | 6/2000 |
| WO | WO-00/51424 | 9/2000 |
| WO | WO-01/30966 | 5/2001 |
| WO | WO-03/005810 | 1/2003 |
| WO | WO-03/055302 | 7/2003 |
| WO | WO-03/059923 | 7/2003 |
| WO | WO-2004/016742 | 2/2004 |
| WO | WO-2004/028243 | 4/2004 |
| WO | WO-2007/035213 | 3/2007 |
| WO | WO-2009/069986 | 6/2009 |
| WO | WO-2011/020120 | 2/2011 |
| WO | WO-2012/112586 A1 | 8/2012 |
| WO | WO-2014/066505 | 5/2014 |
| WO | WO-2016/065046 | 4/2016 |
| WO | WO-2017/044864 A1 | 3/2017 |
| WO | WO-2019/185936 A2 | 10/2019 |
| WO | WO-2020/085788 A1 | 4/2020 |

OTHER PUBLICATIONS

Lee et al., "Recombinase mediated cassette exchange at AAVS1 site in porcine fibroblast cell line," Proceedings of the Korean Veterinary Medical Association, Oct. 2015, 544, abstract P300.

Aigner et al., "Transgenic pigs for xenotransplantation: Selection of promoter sequences for reliable transgene expression," Current Opinion in Organ Transplantation, 2010, 15:201-206.

Ayares, "Genetic Modification of Pigs for Regenerative Medicine", Presentation from UC Davis Transgenic Animal Research Conference VII, Aug. 20, 2009.

Ayares, David. "Genetic Modification of Pigs for Xenotransplantation," Transgenic Research, vol. 19, No. 143 (2010) (pp. 12-31).

Bach et al., "Delayed xenograft rejection", Immunol Today, 1996, vol. 17(8), pp. 379-384.

Bronson et al., "Single-copy transgenic mice with chosen-site integration," Proc. Natl. Acad. Sci. USA, Aug. 1996, 93:9067-9072.

Byrne et al., "Increased Immunosuppression, Not Anticoagulation, Extends Cardiac Xenograft Survival," Transplantation, 2006, 82:1787-1791.

Byrne et al., "Transgenes Expressing Human CD59 and Decay-Accelerative Factor Produce an Intrinsic Barrier to Complement-Mediated Damage1," Transplantation, 1997, 63(1):149-155.

Chen et al., "Complete Inhibition-of Acute Humoral Rejection Using Regulated Expression of Membrane-tethered Anticoagulants on Xenograft Endothelium", American Journal of Transplantation, 2004, vol. 4, pp. 1958-1963.

Chen et al., "Inhibition of intravascular thrombosis in murine endotoxemia by targeted expression of hirudin and tissue factor pathway inhibitor analogs to activated endothelium", Blood, 2004, vol. 104(5), pp. 1344-1349.

Costa et al., "Expression of the human al ,2-fucosyltransferase in transgenic pigs modifies the cell surf ace carbohydrate phenotype and confers resistance to human serum-mediated cytolysis", FASEB J, 1999, vol. 13, pp. 1762-1773.

Cowan et al., "Coagulation and the xenograft endothelium", Xenotransplantation, 2007, vol. 14(1), pp. 7-12.

Cozzi et al., "Preliminary study in a life supporting pig to primate xenotransplantation model using GAL KO pigs transgenic for human CD39, CD55, CD59 and fucosyltransferase," (Abstract LB IXA O-4), Xenotransplantation, 2009, 16:544.

Dai et al., "Targeted disruption of the al ,3-galactosyltransferase gene in cloned pigs", Nature Biotechnology, 2002, vol. 20, pp. 251-255.

Dalmasso et al., "Reaction of Complement With Endothelial Cells in a Model of Xenotransplantation", Clin. Exp. Immunol., 1991, vol. 86, pp. 31-35.

Dalmasso et al., "Inhibition of Complement-Mediated Endothelial Cell Cytotoxicity By Decay-Accelerating Factor", Transplantation, 1991, vol. 52(3), pp. 530-533.

Denning et al., "Deletion of the a(1,3)galactosyl transferase (GGTA 1) gene and the prion protein (PrP) gene in sheep", Nature Biotechnology, 2001, vol. 19, pp. 559-562.

Diamond et al., "Human CD59 expressed in transgenic mouse hearts inhibits the activation of complement", Transplant Immunology, 1995, vol. 3, pp. 305-312.

Dwyer et al., "Thromboregulatory manifestations in human CD39 transgenic mice and the implications for thrombotic disease and transplantation", The Journal of Clinical Investigation, 2004, vol. 113(10), pp. 1440-1446.

Galili et al., "Man, Apes, and Old World Monkeys Differ from Other Mammals in the Expression of a-Galactosyl Epitopes on Nucleated Cells", The Journal of Biological Chemistry, 1988, vol. 263, pp. 17755-17762.

Genbank Accession No. NM_213888.1, 2 pages, downloaded from http://www.ncbi.nlm.nih.gov/nuccore/NM_213888.1 on Feb. 9, 2015.

Giraldo et al,. "Size matters: use of YACs, BACs and PACs in transgenic animals," Transgenic Research, 2001, 10:83-103.

Gock et al., "Genetic modification of pigs for solid organ xenotransplantation," Transplantation Reviews, Jan. 2011, 25:9-20.

Godwin et al., "Towards endothelial cell-specific transgene expression in pigs: characterization of the pig ICAM-2 promoter", Xenotransplantation, 2006, vol. 13(6), pp. 514-521.

Harrison et al., "Efficient generation of a.(1,3) galactosyltransferase knockout porcine fetal fibroblasts for nuclear transfer", Transgenic Research, 2002, vol. 11, pp. 143-150.

Houdebine, Louis-Marie, "Relations between animal transgenesis and reproduction," Reprod. Nutr. Dev., 2005, 45:363-376.

Koike et al., "Direct gene replacement of the mouse a(l,3)-galactosyltransferase gene with human a(l,2)-fucosyltransferase gene: Converting a-galactosyl epitopes into H anti.gens", Xenotransplantation, 1997, vol. 4, pp. 147-152.

Lai et al., ".Production of a-1,3-Galactosyltransferase Knockout Pigs by Nuclear Transfer Cloning", Science, 2002, vol. 295, pp. 1089-1092.

Larin et al., "A method for linking yeast artificial chromosomes," Nucleic Acids Research, 1996, 24(21):4192-4196.

(56) References Cited

OTHER PUBLICATIONS

Lee et al., "Characterization of Transgenic Pigs That Express Human Decay Accelerating Factor and Cell Membrane-tethered Human Tissue Factor Pathway Inhibitor", Reprod Dom Anim, 2010, pp. 1-8.

Lui et al., "Mammary gland-specific secretion of biologically active immunosuppressive agent cytotoxic-T lymphocyte antigen 4 human immunoglobulin fusion protein (CTLA4lg) in milk by transgenesis", Journal of Immunological Methods, 2003, vol. 277, pp. 171-183.

Martin et al., "Transgenic expression of CTLA4-Ig by fetal pig neurons for xenotransplantation", Transgenic Research, 2005, vol. 14, pp. 373-384.

Mirenda et al., "Achieving Permanent Survival of Islet Xenografts by Independent Manipulation of Direct and Indirect T-Cell Responses", Diabetes, 2005, vol. 54, pp. 1048-1055.

Miyagawa et al., "Remodeling of the Major Pig Xenoantigen by N-Acetylglucosaminyltransferase III in Transgenic Pig", The Journal of Biological Chemistry, 2001, vol. 276(42), pp. 39310-39319.

Mohiuddin et al., "One-Year Heterotopic Cardiac Xenograph Survival in a Pig to Baboon Model," Am. J. Transplant, Feb. 2014, 14(2):488-489.

Neimann et al. "Production and characterization of multi-transgenic pigs for xenotransplantation," Transgenic Research, vol. 19 (2010) (pp. 143-144).

Niemann et al., "Production and Characterization of Multi-transgenic Pigs for Xeno Transplantation," Transgenic Research, 2010, 19:143-144.

Phelps et al., "Production of u 1,3-Galactosyltransferase Deficient Pigs", Science, 2003, vol. 299, pp. 411-414.

Piedrahita et al., "Cloning and transgenesis in mammals: Implications for xenotransplantation," American Journal of Transplantation, 2004, 4(Suppl.6):43-50.

Ramsoondar et al., "Production of al, 3-Galactosyltransferase-Knockout Cloned Pigs Expressing Human al, 2-Fucosylosyltransferase", Biology of Reproduction, 2003, vol. 69, pp. 437-445.

Sachs et al., "Genetic Manipulation in Pigs," Curr. Opin. Organ Transplant., Apr. 2009, 14(2):148-153.

Schlaeger et al., "Uniform vascular-endothelial-cell-specific gene expression in both embryonic and adult transgenic mice", 1997, vol. 94(7), pp. 3058-3063.

Shimizu et al., "Thrombotic Microangiopathic Glomerulopathy in Human Decay Accelerating Factor-Transgenic Swine-to-Baboon Kidney Xenografts," J. Am. Soc. Nephrol., 2005, 16:2732-2745.

Sprangers et al., "Xenotransplantation: Where are we in 2008?", Kidney International, Apr. 16, 2008, 74:14-21.

Squinto, "Xenogeneic organ transplantation", Current Opinion in Biotechnology, Dec. 1996, vol. 7(6), pp. 641-645.

Stone et al., "Porcine and Bovine Cartilage Transplants in Cynomolgus Monkey", Transplantation, 1997, vol. 63(5), pp. 640-645.

Strahan et al., "Pig alphal,3Galactosyltransferase: a Major Target for Genetic Manipulation in Xenotransplantation", Frontiers in Bioscience, 1996, vol. 1, pp. 34-41.

Sutherland et al., "Protective Effect Of CTLA4lg Secreted By Transgenic Fetal Pancreas Allografts", Transplantation, 2000, vol. 69(9), pp. 1806-1812.

Tai et al., "Progress in Xenotransplantation Following the Introduction of Gene-knockout Technology," Transplant International, 2007, 20:107-117.

Tanemura et al., "Reduction of the Major Swine Xenoantigen, the a-Galactosyl Epitope by Transfection of the a2,3-Sialyltransferase Gene", The Journal of Biological Chemistry, 1998, vol. 273(26), pp. 16421-16425.

Van de Wouwer et al., "Thrombomodulin-Protein C-EPCR System : Integrated to Regulate Coagulation and Inflammation", Arterioscler Thromb Vasc Biol, 2004, vol. 24, pp. 1374-1383.

Van der Windt et al., "Rapid loss of intraportally transplanted islets: an overview of pathophysiology and preventive strategies", Xenotransplantation, Jul. 2007, vol. 14(4), pp. 288-297.

Vaughan et al., "Porcine CTLA4-lg Lacks a MYPPPY Motif, Binds Inefficiently to Human B7 and Specifically Suppresses Human CD4

T Cell Responses Costimulated by Pig But Not Human B7", The Journal of Immunology, 2000, pp. 3175-3181.

Ye et al., "Evidence That Intravenously Administered a-Galactosyl Carbohydrates Reduce Baboon Serum Cytotoxicity To Pig Kidney Cells (PK15) and Transplanted Pig Hearts", Transplantation, 1994, vol. 58, pp. 330-337.

Quadros et al., "Insertion of sequences at the original provirus integration site of mouse ROSA26 locus using the CRISPR/Cas9 system", FEBS Open Bio, 2015, 5:191-197.

Beaton et al., "GGTA-1 targeting efficiency with a xenograft transgene", 2012, retrieved from https://mospace.umsystem.edu/xmlui/handle/10355/35385# on Aug. 31, 2022.

Kim et al., "Knock-in Somatic Cells of Human Decay Accelerating Factor and a1,2-Fucosyltransferase Gene on the a1,3-Galactosyltransferase Gene Locus of Miniature Pig", Reprod Dev Biol, 2015, 39(3):59-67.

Kim et al., "Porcine Knock-in Fibroblasts Expressing hDAF on a-1,3-Galactosyltransferase (GGTA1) Gene Locus", Asian-Aust. J. Anim. Sci., 2012, 25:1473-1480.

Olsson et al., "The pancreatic islet endothelial cell: Emerging roles in islet function and disease," The International Journal of Biochemistry & Cell Biology, 2006, 38:492-497.

U.S. Appl. No. 17/531,416, filed Nov. 19, 2021.

Ayares, David et al.: "Genetic Engineering of Source Pigs for Xenotransplantation: Progress and Prospects", Xenotransplantation, Sep.-Oct. 2013, vol. 20, No. 5, 408, Sep. 20, 2013 (Sep. 20, 2013), p. 361.

Burdorf et al., "Day Xeno Lung Recipient Survival—Progress towards the Clinic," Journal of Heart and Lung Transplantation, Apr. 2019, 38(4):S39, 72.

Cooper et al., "Recent Advances in Understanding Xenotransplantation: Implications for the Clinic", Expert Review of Clinical Immunology, Sep. 1, 2015, 11(12):1379-1390.

Deng et al., "Use of a 2A Peptide for Generation of Multi-Transgenic Pigs through a Single Round of Nuclear Transfer," PLos One, May 13, 2011, 6(5):1-9, e19986.

Estrada et al., "Evaluation of Human and Non-Human Primate Antibody Binding to Pig Cells Lacking GGTA1/CMAH/b4GalNT2 genes," Xenotransplantation, Mar. 1, 2015, 22:194-202.

Fisicaro et al., "Versatile Co-Expression of Graft-Protective Proteins Using 2A-Linked Cassettes: Transgene Co-Expression Using 2A," Xenotransplantation, Mar. 1, 2011, 18(2):121-130.

Gock et al., "Genetic Modification of Pigs for Solid Organ Xenotransplantation," Transplantation Reviews, Jan. 2011, 25(1):9-20.

Hai et al. "One-step generation of knockout pigs by zygote injection of CRISPR/Cas system," Cell Research, vol. 24 (2014) (pp. 372-375).

Harris et al., "Lung Xenotransplantation: Recent Progress and Current Status, " Xenotransplantation, 2014, 21(6):496-506.

Harris et al., "Meta-Analysis of 1-8, the Independent and Cumulative Effects of 11-27 Multiple Genetic Modifications on Pig Lung Xenograft Performance During Ex Vivo Perfusion with Human Blood," Xenotransplantation, Dec. 2014, 22(2):102-111.

Iwase et al., "Immunological and Physiological Observations in Baboons with Life-Supporting Genetically Engineered Pig Kidney Grafts," Xenotransplantation, Mar. 17, 2017, 24(2):e12293, 1-31.

Iwase et al., "Pig Kidney Graft Survival in a Baboon for 136 Days: Longest Life-Supporting Organ Graft Survival to Date," Xenotransplantation, Jun. 29, 2015, 22(4):302-309.

Kemter et al., "Xeno-organ donor pigs with multiple genetic modifications—the more the better?", Current Opinion in Genetics & Development, Jun. 30, 2020, 64:60-65.

Kriz et al., "A plasmid-based multigene expression system for mammalian cells," Nat. Commun., 2010, 1:120, 1-6 and Supplemental material 1-21.

Niu et al., "Porcine genome engineering for xenotransplantation," Advanced Drug Delivery Reviews, 2021, 168:229-245.

Nottle et al. "Production of homozygous a-1,3-galactosyh:ransferase knockout pigs by breeding and somatic cell nuclear transfer," Xenotransplantation, vol. 14, No. 4 (2007) (pp. 339-344).

Pierson et al., "Progress Toward Cardiac Xenotransplantation," Circulation, 142(14):1389-1398.

(56) References Cited

OTHER PUBLICATIONS

Salvaris et al., "IXA-0-7.1: Multi-Gene Constructs to Accelerate the Generation of Multi-Transgenic GalT Knockout Pigs," Xenotransplantation, Sep. 2009, 16(5):373.

Tena et al., "Transgenic Expression of Human CD47 Markedly Increases Engraftment in a Murine Model of Pig-to-Human Hematopoietic Cell Transplantation," Am. J. Transplant., 2014, 14(12):2713-2722.

Ulrichts et al., "Shielding of the A1 Doman by the D D3 Domains of von Willebrand Factor Modulates its Interaction with Platelet Glycoprotein lb-IX-V *;" The Journal of Biological Chemistry, Feb. 24, 2006; 281(8):4699-4707.

Wei, Deng et al.: "Use of the 2A Peptide for Generation of Multi-Transgenic Pigs through a Single Round of Nuclear Transfer", Plos One, vol. 6, No. 5, May 13, 2011 (May 13, 2011), p. e19986.

Yu et al., "Lentiviral Vectors with two Independent Internal Promoters Transfer High-Level Expression of Multiple Transgenes to Human Hematopoietic Stem-Progenitor Cells," Mol. Ther., 2003, 7(6):827-838.

Cooper et al., "Experimental Pig Heart Xenotransplantation—Recent Progress and Remaining Problems," Ann. Thorac. Surg., Apr. 2019, 107(4):989-992.

Definition of "permit", Dictionary.com, 2024, 1-6.

Hinrichs et al., "Inactivation of the GHR gene—a strategy to overcome excess growth of orthotopic pig-to-baboon cardiac xenografts?", Xenotransplantation, 2017, 24(e12328):39-40, Abstract O.6.2, Abstracts of the 14th Congress of the International Xenotransplantation Association, Sep. 20-23, 2017, Baltimore, MD, https://doi.org/10.1111/xen.12328.

Ohtsuka et al., "One-step generation of multiple transgenic mouse lines using an improved Pronuclear Injection-based Targeted Transgenesis (i-PITT)," MBC Genomics, 2015, 16:274, 1-16.

Phelps et al., "Production and characterization of transgenic pigs expressing porcine CTLA4-lg," Xenotransplantation, Nov.-Dec. 2009, 16(6):477-485.

Fischer et al., "Multi-transgenic pigs for xenotransplantation," Xenotransplantation, 2013, 20:64; Berlin Symposium on Xenotransplantation 2012—Abstracts.

Hinrichs et al., "Growth hormone receptor knockout in GTKO/hCD46/hTM pigs as a strategy to prevent overgrowth of orthotopic xeno-hearts in baboons," Xenotransplantation, 2019, 26(5):Abstract 225.3.

Hurh et al., "Expression Analysis of Combinatorial Genes Using a Bi-Cistronic T2A Expression System in Porcine Fibroblasts," PLoS One, Jul. 2013, 8(7): e70486, 1-11.

* cited by examiner pREV 859B pREV 861 pREV 871 pREV 872 pREV 873

Pig 424-3 Tail

GENETICALLY MODIFIED PIGS FOR XENOTRANSPLANTATION OF VASCULARIZED XENOGRAFTS AND DERIVATIVES THEREOF

CROSS-REFERENCE TO RELATED APPLICATIONS

This application is a Continuation of U.S. application Ser. No. 13/966,121, which is the U.S. National Stage of PCT/US2012/025091, filed Feb. 14, 2012, which claims priority to U.S. provisional patent application 61/442,504, filed on Feb. 14, 2011.

The instant application contains a Sequence Listing which has been submitted in ASCII format via EFS-WEB and is hereby incorporated by reference in its entirety. Said ASCII copy, created on Nov. 22, 2021, is named sequence.txt and is 4,722 bytes.

FIELD OF THE INVENTION

The present invention provides certain donor animals, tissues and cells that are particularly useful for xenotransplantation therapies. In particular, the invention includes porcine animals, as well as tissue and cells derived from these, which lack any expression of functional alpha 1,3 galactosyltransferase (aGT) and express one or more additional transgenes which make these animals suitable donors for xenotransplantation of vascularized xenografts and derivatives thereof. Methods of treatment and using organs, tissues and cells derived from such animals are also provided.

BACKGROUND OF THE INVENTION

There is a critical shortage of human organs for the purposes of organ transplantation. In the United States alone approximately 110,000 patients are on waiting lists to receive organs, and yet only 30,000 organs will become available from deceased donors. Almost 20 patients die each day (7000 per year) waiting for an organ (Cooper and Ayares, 2010 International Journal of Surgery, In Press, doi:10.1016/j.ijsu.2010.11.002). The supply of human organs and tissues for use in allotransplantation will never fully meet the population's need. A new source of donor materials is urgently needed.

Xenotransplantation

Xenotransplantation (transplant of organs, tissues and cells from a donor of a different species) could effectively address the shortage of human donor material. Xenotransplants are also advantageously (i) supplied on a predictable, non-emergency basis; (ii) produced in a controlled environment; and (iii) available for characterization and study prior to transplant.

Depending on the relationship between donor and recipient species, the xenotransplant can be described as concordant or discordant. Concordant species are phylogenetically closely related species (e.g., mouse to rat). Discordant species are not closely related (e.g., pig to human). Pigs have been the focus of most research in the xenotransplanation area, since the pig shares many anatomical and physiological characteristics with human. Pigs also have relatively short gestation periods, can be bred in pathogen-free environments and may not present the same ethical issues associated with animals not commonly used as food sources (e.g., primates).

Scientific knowledge and expertise in the field of pig-to-primate xenotransplantation has grown rapidly over the last decade, resulting in the considerably prolonged survival of primate recipients of lifesaving porcine xenografts. (Cozzi et al., Xenotransplantation, 16:203-214. 2009). Recently, significant achievements have been reported in the field of organ xenotransplantation. For a review of organ xenotransplantation results, see Ekser et al., 2009, Transplant Immunology June; 21 (2): 87-92

Genetic Modification

While advantageous in many ways, xenotransplantation also creates a more complex immunological scenario than allotransplantation. As such, considerable effort has been directed at addressing the immune barrier through genetic modification (van der Windt et al., Xenotransplantation. 2007 July; 14 (4): 288-97, Cowan and D'Apice, Curr Opin Organ Transplant. 2008 April; 13 (2): 178-83).

Xenograft rejection can be divided into three phases: hyperacute rejection, acute humoral xenograft rejection, and T cell-mediated cellular rejection. Hyperacute rejection (HAR) is a very rapid event that results in irreversible graft damage and loss within minutes to hours following graft reperfusion. It is triggered by the presence of xenoreactive natural antibodies present within the recipient at the time of transplantation. Humans have a naturally occurring antibody to the alpha 1,3-galactose (Gal) epitope found on pig cells. This antibody is produced in high quantity and, it is now believed, is the principle mediator of HAR. (Sandrin et al., Proc Natl Acad Sci 1993 Dec. 1; 90 (23): 11391-5, 1993; review by Sandrin and Mckenzie, Immunol Rev. 1994 October; 141:169-90).

Initial efforts to genetically modify pigs have focused on removing the alpha 1,3-galactose (Gal) epitope from pig cells. In 2003, Phelps et al. (Science, 2003, 299:411-414) reported the production of the first live pigs lacking any functional expression of αGT (GTKO), which represented a major breakthrough in xenotransplantation (see also PCT publication No. WO 04/028243 to Revivicor, Inc. and PCT Publication No. WO 04/016742 to Immerge Biotherapeutics, Inc.). Subsequent studies have shown that organ grafts from GTKO pigs do not undergo HAR (Kuwaki et al., Nat Med. 2005 January; 11 (1): 29-31, Yamada et al., Nat Med. 2005 January; 11 (1): 32-4). Expression of complement regulators in xenotransplant tissue has been suggested as a different strategy to combat HAR (Squinto, Curr Opin Biotechnol. 1996 December; 7 (6): 641-5). European patent 0495852 to Imutran suggests associating xenograft tissues with recipient complement restriction factors to reduce complement activation in the recipient (see also Diamond, et al., Transpl Immunol. 1995 December; 3 (4): 305-12). Transgenic pigs expressing human DAF (hDAF) and/or human CD59 (hCD59) have been reported (Byrne et al., Transplant Proc., 1996 April; 28 (2): 758).

CD46 has been expressed in pig cells using a minigene that was optimized for high ubiquitous expression and kidneys from these CD46 transgenic pigs were protected from hyperacute rejection in a primate xenotransplantation model (Loveland et al., Xenotransplantation, 2004, 11:171: 183). Transgenic pigs with the combination of GTKO and expression of CD46 were recently tested in a heterotopic heart model (pig-to-baboon) and provided prolonged survival and function of xenograft hearts for up to 8 months without any evidence of immune rejection (Mohiuddin et al., Abstract TTS-1383. Transplantation 2010; 90 (suppl): 325; Mohiuddin et al. (2011), online publication American Journal of Transplantation). However, the primates were placed on a ATG, anti-CD154 and MMF-based immunosuppressive regimen, which prolonged GTKO.hCD46Tg graft survival for up to 236 days (n=9, median survival 71 days and mean survival 94 days). It is not possible for this type of immunosuppressive regimen to be used in humans. Ekser et al. (Transplantation 2010 Sep. 15; 90 (5): 483-93) reported hepatic function in baboons after transplant of livers from alpha-1,3-galactosyltransferase gene-knockout pigs transgenic for CD46. The recipient baboons died or were euthanized after 4 to 7 days but was limited by the rapid development of a profound thrombocytopenia.

Even where HAR is avoided, the xenograft undergoes a delayed form of rejection, acute humoral or acute vascular xenograft rejection (AHXR/AVXR)—also referred to as delayed xenograft rejection (DXR) (Shimizu et al 2008 Am J Pathol. 2008 June; 172 (6): 1471-81). It is generally thought to be initiated by xeno-reactive antibodies, including non-Gal antibodies and subsequent activation of the graft endothelium, the complement and the coagulation systems (Miyagawa et al. Xenotransplantation, 2010, 1:11-25). Although the threats presented by the humoral response are critical with regard to the survival and function of vascularized grafts, the risk of graft damage by cellular mechanisms is also important. T-cell mediated acute responses play an important role in xenotransplant rejection. Of several T cell costimulatory pathways identified to date, the most prominent is the CD28 pathway and the related cytoxic T-lymphocyte associated protein (CTLA4) pathway.

To date, much of the research on CTLA4-Ig as an immunosuppressive agent has focused on administering soluble forms of CTLA4-Ig to a patient (see U.S. Pat. No. 7,304,033; PCT Publication No. WO 99/57266; and Lui et al. J Immunol Methods 2003 277:171-183). To reduce the overall immunosuppressive burden on a patient, transgenic expression of such a protein has been suggested. Transgenic mice expressing CTLA4-Ig have been developed (Ronchese et al. J Exp Med (1994) 179:809; Lane et al. J Exp Med. (1994) March 1; 179 (3): 819; Sutherland et al. Transplantation. 2000 69 (9): 1806-12). In addition, PCT Publication No. WO 01/30966 to Alexion Pharmaceuticals, Inc. and PCT Publication No. WO 07/035213 to Revivicor discloses transgenic pigs expressing only the CTLA4-Ig transgene (see also Phelps et al., Xenotransplantation, 16 (6): 477-485. 2009). Pigs expressing CTLA4-Ig in brain tissue were produced, but high plasma expression was shown to cause negative effects (Martin, et al. (2005) Transg. Rsch. 14:373-84). There remains doubt as to whether long term expression of immunosuppressive transgenes in ungulates raises safety concerns either for the ungulate or for the recipient of any tissues from such an animal.

In addition to the cellular and humoral immune responses, a significant challenge associated with xenotransplantation is coagulation dysregulation and thrombotic microangiopathy in the vasculature of the graft (Ekser et al, 2009 June; 21 (2): 87-92). This phenomenon came to light when HAR was prevented by removal of the Gal epitope and/or transgenic expression of complement inhibitors, and classical AHXR was also prevented with high levels of immunosuprression. This intravascular coagulation is triggered by either antibody/cell-mediated damage of the endothelium or by coagulation factor incompatibilities between the discordant species (pig and non-human primate), which leads to endothelial activation. In a transplant setting, the endothelium of a donor vascularized graft is where donor antigens come into contact with a recipient's (or host's) bloodstream, leading to an antibody mediated immune response, and potential rejection of the graft. Depending on the relatedness of the donor and the recipient, various types of immune rejection can occur. (see, for example, Fundamental Immunology, Ed. William E. Paul, Lippincott Williams & Wilkins; Sixth edition (May 22, 2008), Chapter 44)

Once the endothelium is activated, it changes from its anticoagulant state to a procoagulant state by up regulation of von Willebrand factor and production of tissue factor leading to thrombus formation, hemorrhage, and rejection of the graft (Mohiuddin, 2007, PLOS Medicine, Vol 4 (3) p. 0429-0434). Until this intravascular coagulation issue is addressed, obtaining long-term survival of a vascularized xenograft will remain a formidable challenge.

The addition of an anticoagulant transgene has been suggested to prevent coagulation responses to xenografts (reviewed by Cowan, Xenotransplantation, 2007; 14:7-12), yet to date, very few transgenic pigs expressing anticoagulants have been produced and none have been tested in vivo in xenotransplantation models. Significant health and viability issues in pigs produced with an anticoagulant phenotype has led to a low rate of production of viable transgenic animals. In mice, expression of the anticoagulant CD39 driven by an murine H2-K (MHC class I) promoter, led to impaired platelet aggregation and prolonged bleeding times (see Dwyer et al. (2004) J Clin Invest 113:1440-46). Another group attempted to produce TFPI transgenic pigs in combination with a DAF transgene driven by the pCMVIE constiutive promoter enhancer via nuclear transfer (Lee et al 2010 Reprod Domest Anim. 2010 Jul. 4 epub ahead of print PMID: 20626677). Only one viable transgenic piglet was obtained from this effort and it was shown to express DAF and TFPI in heart, liver and ear cells examined.

Multi-transgenic pigs have also been generated which contain hCD59, DAF and TM transgenes, with the anticoagulant TM driven by a CMV promoter (Petersen et al., Xenotransplantation 2009: 16: 486-495), however there was considerable variability in TM expression level in these pigs. Further, Dwyer et al. (Transplantation Reviews 21 (2007) 54-63), briefly reported the generation of CD39 transgenic pigs. U.S. Pat. No. 7,378,569 discloses transgenic pigs carrying two transgenes, one encoding a human decay accelerating factor (hDAF) and the other encoding a human heme oxygenase-1 (hHO)-1, which are useful for providing cells, tissues or organs therefrom for xenotransplantation. Ayares (2009 Xenotransplantation 16(5) 373) discusses further genetic modification, building on the GTKO genetic background, has been initiated by a number of groups to address issues such as induced antibody responses to non-Gal antigens, thrombosis, and cell-mediated immune responses.

Although xenotransplantation of organs, particularly from porcine donors, is an appealing alternative to the use of allografts because of the limited supply and quality of human donor materials, major obstacles remain. Both immediate and delayed immune responses require potentially toxic cocktails of immunosuppressant therapies, and even then, endothelial activation and subsequent coagulation dysregulation and thrombosis in the graft can cause graft failure. The production of genetically modified animals to address certain immune responses has been suggested; however, this requires the coordinated elimination and appropriate expression of multiple transgenes that are capable of addressing each immune response without significantly curtailing the overall health and viability of the pig. Thus, there remains a need for improved animals and tissues suitable for xenotransplantation therapies. In particular, there remains a need for improved donor animals, organs and tissues for use in xenotransplantation without requiring significant or long term immunosuppressive or anticoagulant therapies.

It is an object of the present invention to provide genetically modified porcine animals for xenotransplantation of vascularized xenografts and derivatives thereof.

It is another object of the present invention to provide vascularized xenografts from genetically modified porcine animals which express of one or more immunosuppressant and/or anticoagulant transgenes and lack expression of alpha-1,3-galactosyltransferase.

It is a further object of the present invention to provide genetically modified porcine animals which express of one or more immunosuppressant and/or anticoagulant transgenes spherically in the endothelium.

SUMMARY OF THE INVENTION

The present invention provides genetically modified porcine animals, organs, tissues and cells thereof that are particularly useful for xenotransplantation of vascularized xenografts and derivatives thereof. Vascularized xenografts can include any organ, tissue, cell or combination thereof, that contains porcine blood vessels and/or is derived from an organ, tissue or cell therefrom. The genetically modified donor animals serve as a source of organs, tissues and cells that overcome significant humoral (HAR and AHXR/AVXR/DXR) and cellular immune responses (ACXR), making them particular useful for xenotransplantation. Specifically, the genetically modified donor animals have transgenes specifically expressed in the vascular endothelium.

Since the vascular endothelium is the site of first contact between the recipient's bloodstream and a donor graft, and the site of the initial immune activation and response; modification of the pig's endothelium will reduce graft damage and rejection due to the consumptive coagulopathy (also known as disseminated intravascular coagulation (DIC)), and thrombotic microangiopathy currently observed following discordant xenotransplantation. Such genetically modified donor animals can serve as a source of vascularized xenografts (as well as the organs, tissues and cells derived therefrom), making them particular useful for xenotransplantation, using a clinically relevant immunosuppressant regimen.

The viable, genetically modified porcine animals of the present invention are characterized by globally reduced immune reactivity (i.e., due to the lack of expression of functional alpha 1,3 galactosyl transferase ($\alpha$GT)) as well as the expression of transgenes critical to overcome transplant rejection, selected from the group including anticoagulants, immunomodulators and cytoprotectants. Prior to the present invention, it was unknown whether these types of transgenes, which can cause the animal to be immuno-compromised and hemophilic, could be expressed in a single animal that would be able to be a suitable transplantation donor because it was expected that the animals' viability would be severely curtailed. The present inventors have found that such donor animals, tissues and cells can be obtained, in particular when globally reduce immune reactivity due to lack of expression of functional alpha 1,3 galactosyltransferase (GTKO) is combined with endothelial specific expression of certain transgenes.

Further embodiments of the present invention include the addition of an immunomodulator transgene that is specifically expressed in the endothelium. The immunomodulator can be an immunosuppressor molecule, such as CTLA4, in particular, CTLA4-Ig. The local expression of an immunomodulator allows for the ultimate use of a clinically relevant immunosuppressant regimen in the human following xenotransplantation of the organ, tissue or cell.

In one embodiment of the present invention, GTKO porcine animals, organs, tissues and cells are provided that specifically express at least one transgene in endothelium.

In a particular embodiment, the transgene specifically expressed in endothelium is at least one anticoagulant. In another particular embodiment, the transgene specifically expressed in endothelium is at least one immunomodulator. In specific embodiment, the transgene specifically expressed in endothelium is at least one immunosuppressant. In a further particular embodiment, the transgene specifically expressed in endothelium is at least one cytoprotective transgene.

In another embodiment of the present invention, GTKO animals, tissues and cells are provided that specifically express multiple transgenes in endothelium. In a particular embodiment, the multiple transgenes are selected from the group that includes anticoagulants, immunomodulators and cytoprotective transgenes.

In a particular embodiment, GTKO animals, tissues and cells are provided that specifically express at least two transgenes in endothelium. In a specific embodiment, the at least two transgenes are both anticoagulants.

In a particular embodiment, GTKO animals, tissues and cells are provided specifically express at least three transgenes in endothelium. In a specific embodiment, the at least three transgenes include two anticoagulant transgenes and an immunosuppressant transgene.

In a further specific embodiment, GTKO animals, tissues and cells are provided that lack any expression of functional alpha 1,3 galactosyltransferase (GTKO) and that specifically express thrombomodulin and EPCR (Endothelial Protein C Receptor) in endothelium.

In a further embodiment of the present invention, porcine animals, tissues and cells are provided that lack any expression of functional alpha 1,3 galactosyltransferase (GTKO) and that express at least one first transgene and at least one second transgene, wherein the second transgene is specifically expressed in endothelium.

In one embodiment, the at least one first transgene is an immunomodulator. In a particular embodiment, the at least one first transgene is a compliment inhibitor.

In another embodiment, the at least one first transgene is a compliment inhibitor and the at least one second transgene specifically expressed in endothelium is selected from the group that includes (i) an anticoagulant; (ii) an immunosuppressive; and (iii) a cytoprotectant.

In one embodiment, porcine animals, tissues and cells are provided that lack any expression of functional alpha 1,3 galactosyltransferase (GTKO) and expresses at least one compliment inhibitor and at least one additional transgene selected from the group consisting of anticoagulants, immunosuppressants and cytoprotectants.

In a specific embodiment, porcine animals, tissues and cells are provide that lack any expression of functional alpha 1,3 galactosyltransferase (GTKO) and expresses at least one compliment inhibitor and at least one anticoagulant. In a particular embodiment, the compliment inhibitor is CD46 and the at least one anticoagulant is selected from the group that consists of TFPI, CD39, hirudin, thrombomodulin and EPCR. In a particular embodiment, the at least one compliment inhibitor is CD46 and the at least one anticoagulant is thrombomodulin. In a further particular embodiment, the at least one compliment inhibitor is CD46 and the at least one additional transgene is an immunosuppressant, e.g., CTLA4.

In a specific embodiment, porcine animals, tissues and cells are provided that lack any expression of functional alpha 1,3 galactosyltransferase (GTKO) and further express at least one compliment inhibitor, at least one anticoagulant and at least one immunosuppressant. Optionally, the porcine animals, tissues and cells also express at least one cytoprotective transgene.

In one embodiment, the transgene is specifically expressed in endothelium. In a particular embodiment, the transgene is specifically expressed in endothelial cells. In a specific embodiment, the transgene is expressed in the vascular endothelium. The vascular endothelium refers to the endothelial cells lining blood vessels. It is understood that these blood vessels innervate the organs and tissues of the present invention. In a specific embodiment, the transgene is expressed in vascular endothelium of a tissue or organ selected from the group including but not limited to: heart, kidney, liver, lung, cornea and blood vessels. The expression can be at any level, but in a specific embodiment, the expression is at a high level. In one embodiment, expression of transgenes described herein is driven by an endothelial-specific promoter. In a specific embodiment, the endothelial-specific promoter is intercellular adhesion molecule 2 (ICAM-2). In another specific embodiment, the endothelial-specific promoter is TIE-2. In certain embodiments, the promoter is a porcine promoter.

An anticoagulant according to the present invention can be selected from the group that includes tissue factor pathway inhibitor (TFPI), hirudin, thrombomodulin (TM), endothelial protein C receptor (EPCR), and CD39. In a particular embodiment, the anticoagulant is TFPI. In another embodiment, the anticoagulant is CD39. In another embodiment, the anticoagulant is thrombomodulin.

An immunomodulator according to the present invention can be a complement inhibitor or an immunosuppressant. In specific embodiments, the immunomodulator is a complement inhibitor. The complement inhibitor can be CD46 (or MCP), CD55, CD59 and/or CR1. In a specific embodiment, at least two complement inhibitors can be expressed. In one embodiment, the complement inhibitors can be CD55 and CD59. In another embodiment, the immunomodulator can be a class II transactivator or mutants thereof. In certain embodiments, the immunomodulator can be a class II transactivator dominant negative mutant (CIITA-DN). In another specific embodiment, the immunomodulator is an immunosuppressant. The immunosuppressor can be CTLA4-Ig. Other immunomodulators can be selected from the group but not limited to CIITA-DN, PDL1, PDL2, or tumor necrosis factor-α-related apoptosis-inducing ligand (TRAIL), Fas ligand (FasL, CD95L) CD47, known as integrin-associated protein (CD47), HLA-E, HLA-DP, HLA-DQ, and/or HLA-DR.

The cytoprotective transgene according to the present invention can be an anti-apoptotic, an anti-oxidant or an anti-inflammatory transgene. In certain embodiments, the cytoprotective transgene is selected from the group that includes A20, HO-1, FAT-1, catalase, and soluble TNF-alpha receptor (sTNFR1).

In a specific embodiment, the present invention provides porcine animals, tissues and cells with at least the following genetic modifications: lack of expression of GT, expression of CD46 and endothelial-specific expression of thrombomodulin. In a particular embodiment, CD46 is ubiquitously expressed.

In another embodiment, the present invention provides porcine animals, tissues and cells with at least the following genetic modifications: lack of expression of GT, expression of a complement inhibitor, endothelial-specific expression of an anticoagulant and/or endothelial-specific expression of an immunomodulator. In another specific embodiment, the present invention provides porcine animals, tissues and cells with at least the following genetic modifications: lack of expression of GT, expression of CD46, and endothelial-specific expression of thrombomodulin. In a further embodiment, the present invention provides porcine animals, tissues and cells with at least the following genetic modifications: lack of expression of GT, expression of CD46 and endothelial-specific expression of CD39. In a specific embodiment, the present invention provides porcine animals, tissues and cells with at least the following genetic modifications: lack of expression of GT, expression of CD46, endothelial-specific expression of thrombomodulin, and endothelial-specific expression of CD39. In particular embodiments, CD46 can be ubiquitously expressed.

In another specific embodiment, the present invention provides porcine animals, tissues and cells with at least the following genetic modifications: lack of expression of GT, expression of CD46, endothelial-specific expression of thrombomodulin, and endothelial-specific expression of CTLA4-Ig. In a further specific embodiment, the present invention provides porcine animals, tissues and cells with at least the following genetic modifications: lack of expression of GT, expression of CD46, endothelial-specific expression of thrombomodulin, and endothelial-specific expression of CIITA-DN. In a particular embodiment, CD46 is ubiquitously expressed.

In another specific embodiment, the present invention provides porcine animals, tissues and cells with at least the following genetic modifications: lack of expression of GT, expression of CD46, endothelial-specific expression of thrombomodulin, and expression of EPCR. In a particular embodiment, CD46 is ubiquitously expressed. In one embodiment, expression of EPCR is driven by a endothelial-specific promoter. In a specific embodiment, the endothelial-specific promoter is porcine ICAM-2. In another specific embodiment, the endothelial-specific promoter is TIE-2. In one embodiment, expression of EPCR is driven by a ubiquitous promoter. In a specific embodiment, the ubiquitous promoter is CAG.

In a further specific embodiment, the present invention provides porcine animals, tissues and cells with at least the following genetic modifications: lack of expression of GT, expression of CD46, endothelial-specific expression of thrombomodulin, endothelial-specific expression of CD39, and endothelial-specific expression of CTLA4-Ig. In a particular embodiment, CD46 is ubiquitously expressed. In an alternate embodiment, the porcine can express TFPI in place of or in addition to thrombomodulin.

In another specific embodiment, the present invention provides porcine animals, tissues and cells with at least the following genetic modifications: lack of expression of GT, expression of CD46, expression of an cytoprotective transgene, endothelial-specific expression of thrombomodulin, endothelial-specific expression of CD39, and endothelial-specific expression of CTLA4-Ig. In a particular embodiment, CD46 is ubiquitously expressed.

In another specific embodiment, the present invention provides porcine animals, tissues and cells with at least the following genetic modifications: lack of expression of GT, expression of CD46, expression of a cytoprotective transgene, endothelial-specific expression of thrombomodulin and endothelial-specific expression of CD39. In a particular embodiment, CD46 is ubiquitously expressed. In an alternate embodiment, the porcine can express TFPI in place of or in addition to thrombomodulin.

In a further specific embodiment, the present invention provides porcine animals, tissues and cells with at least the following genetic modifications: lack of expression of GT, expression of CD46, expression of CIITA-DN, and endothelial specific expression of thrombomodulin and/or endothelial specific expression of CD39. In a particular embodiment, CD46 is ubiquitously expressed.

In a further specific embodiment, the present invention provides porcine animals, tissues and cells with at least the following genetic modifications: lack of expression of GT, expression of CD46, expression of DAF, expression of CIITA-DN, and endothelial-specific expression of thrombomodulin and/or endothelial-specific expression of CD39. Alternately, the present invention provides porcine animals, tissues and cells with at least the following genetic modifications: lack of expression of GT, expression of CD46, endothelial-specific expression of thrombomodulin and/or endothelial-specific expression of EPCR. In a further specific embodiment, the present invention provides porcine animals, tissues, particularly lungs, and cells, particularly lung cells, with at least the following genetic modifications: lack of expression of GT, expression of CD46, and endothelial-specific expression of thrombomodulin. In a particular embodiment, CD46 is ubiquitously expressed.

In one embodiment, a method is provided for treatment or prophylaxis of organ dysfunction including administering the organs or cells of the present invention to a host in need thereof. In a particular embodiment, the host has heart, liver, kidney or lung dysfunction. In another embodiment, the host is administered a vascularized xenograft and/or is derived from an organ, tissue or cell therefrom.

In one embodiment, the host is a primate. In a particular embodiment, the host is a human. In a specific embodiment, the host is a human suffering from organ dysfunction.

In one embodiment, the organ is a porcine heart. In another embodiment, the organ is a porcine kidney. In another embodiment, the organ is a porcine lung. In another embodiment, the organ in is a porcine liver. In another embodiment, the cells are porcine liver-derived cells, liver tissue slices; or isolated liver cells. In a particular embodiment, the cells are porcine hepatocytes. In a particular embodiment porcine hepatocytes or porcine liver tissue slices can be used in a medical device. In additional embodiments, organs according to the present invention can be selected from the following: heart, lung, liver, kidney, intestine, spleen, and pancreas. In one embodiment, the organs can be used as bridge organs until a human organ becomes available. In other embodiments, the xenotransplanted organs of the present invention can survive and function in the recipient like an allograft.

In a particular embodiment, a porcine donor liver may be used as a bridge transplant, allowing for stabilization of a patient until a human donor liver (allograft) becomes available.

It is envisioned that in certain embodiments of the present invention, the endothelial cells themselves produced by the methods disclosed herein can be used as the xenotransplanted cell.

In a particular embodiment, porcine endothelial cells from the cornea can be used as a transplant material to treat cornea dysfunction.

In a particular embodiment, porcine endothelial cells from the retina can be used as a transplant material to treat retina dysfunction.

In further embodiments, it is envisioned that the vasculature itself can be used as the xenograft as a vascular graft. In some embodiments, vessels can be used as grafts for the following including but not limited to vascular reconstructive surgery, coronary bypass surgery, or peripheral bypass surgery to treat atherosclerosis, coronary artery disease, peripheral vascular disease or aortic aneurysm. In embodiments of the present invention, vessels can include large and microvasculature tissue, such as microvessels, capillaries, microcappilaries and capillary beds.

In one embodiment, the dose of immunosuppressive drug(s)/agent(s) is/are reduced compared to other methods. In a specific embodiment, the dosage of one or more of daclizumab, tacrolimus, and/or sirolimus is reduced compared to dosages used in other methods of transplantation. In particular embodiments of the present invention, clinically relevant immunosuppressant regimens are provided in conjunction with the organs, tissues and cells described herein.

In another embodiment, the number of types of immunosuppressive drug(s)/agent(s) is/are reduced compared to other methods.

In one embodiment, the duration of immunosuppression is shortened compared to other methods.

In another embodiment, lower or no maintenance immunosuppression is used compared to other methods.

In one embodiment, a method is provided for treatment or prophylaxis of organ dysfunction including administering the organs, tissues or cells of the present invention to a host, wherein post-transplant there are not numerous, or serious life-threatening, complications associated with one or more of the transplant procedure, the immunosuppressive regime or the tolerance inducing regime. In one embodiment, a method is provided for treatment or prophylaxis of organ dysfunction including administering the organs, tissues or cells of the present invention to a host, wherein post-transplant there are not numerous, or serious life-threatening, complications associated with one or more of the transplant procedures. In a specific embodiment, a method is provided for treatment or prophylaxis of organ dysfunction including administering the organs, tissues or cells of the present invention to a host, wherein post-transplant there are not numerous, or serious life-threatening, complications, including consumptive coagulopathy.

In another embodiment, a method is provided for treatment or prophylaxis eye disease, including for treatment of cornea or retina dysfunction, including administering the organs, tissues or cells of the present invention to a host, wherein post-transplant there are not numerous, or serious life-threatening, complications associated with one or more of the transplant procedure, the immunosuppressive regime or the tolerance inducing regime.

Other embodiments of the present invention will be apparent to one of ordinary skill in light of the following description of the invention, the claims and what is known in the art.

DESCRIPTION OF FIGURES

FIG. 1a: vector pREV859B is the Tie-2 promoter/enhancer linked to a CD39 transgene; vector pREV861 is the ICAM-2 promoter/enhancer linked to a CD39 transgene.

FIG. 1b: vector pREV 871 is the ICAM-2 promoter/enhancer linked to a TFPI transgene; vector pREV 872 is the is the ICAM-2 promoter/enhancer linked to a TM transgene; vector pREV 873 is the ICAM-2 promoter/enhancer linked to an EPCR transgene.

DETAILED DESCRIPTION OF THE INVENTION

Figure 1A:
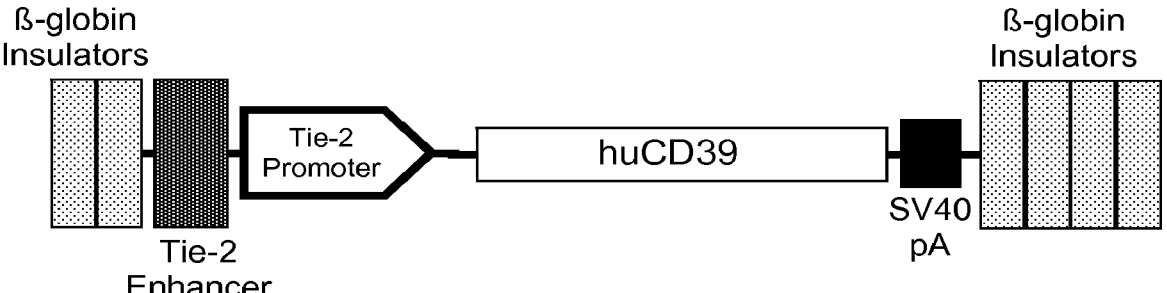
FIGS. 1a and 1b are representative figures of the vectors used in the invention.
Figure 1A:
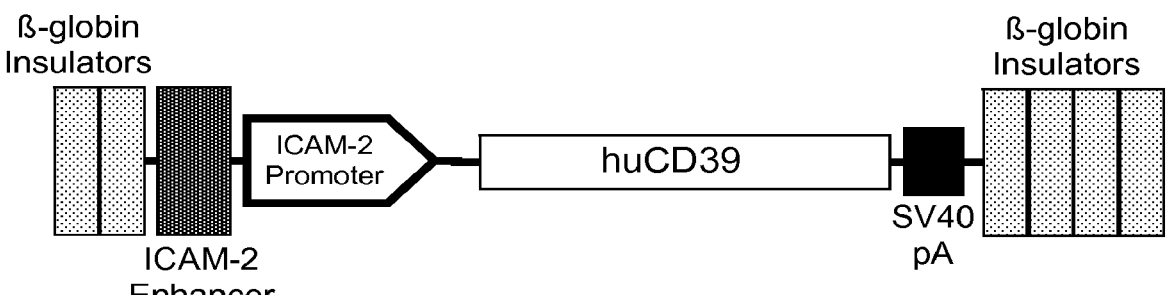
Figure 1B:
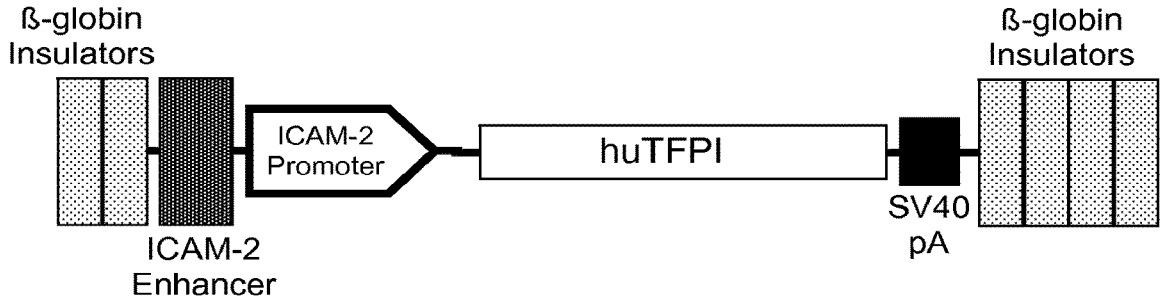
Figure 1B:
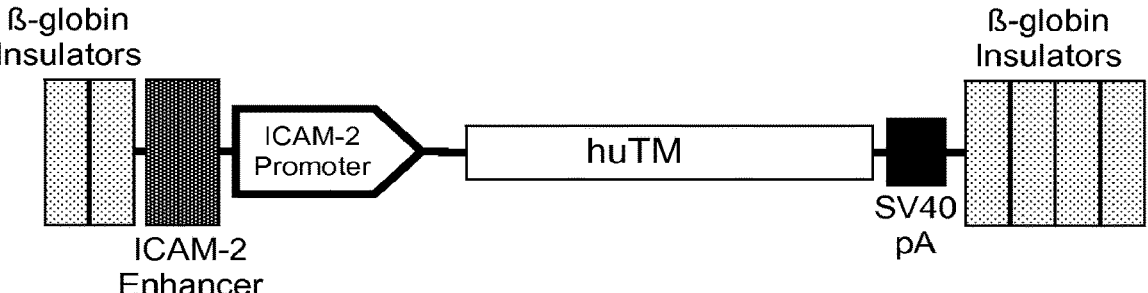
Figure 1B:
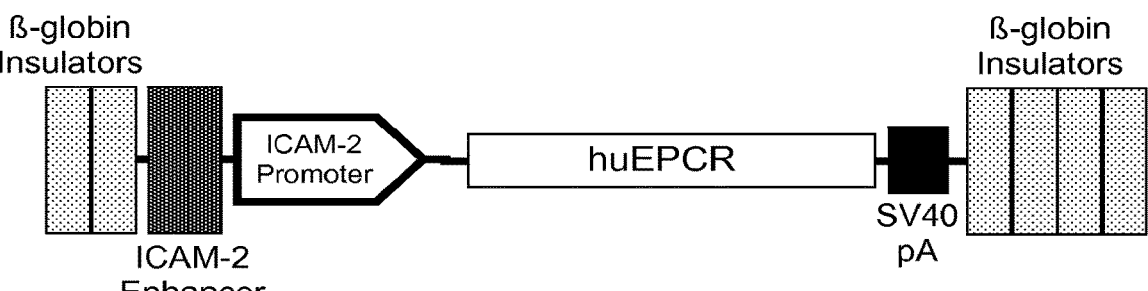
Figure 2:
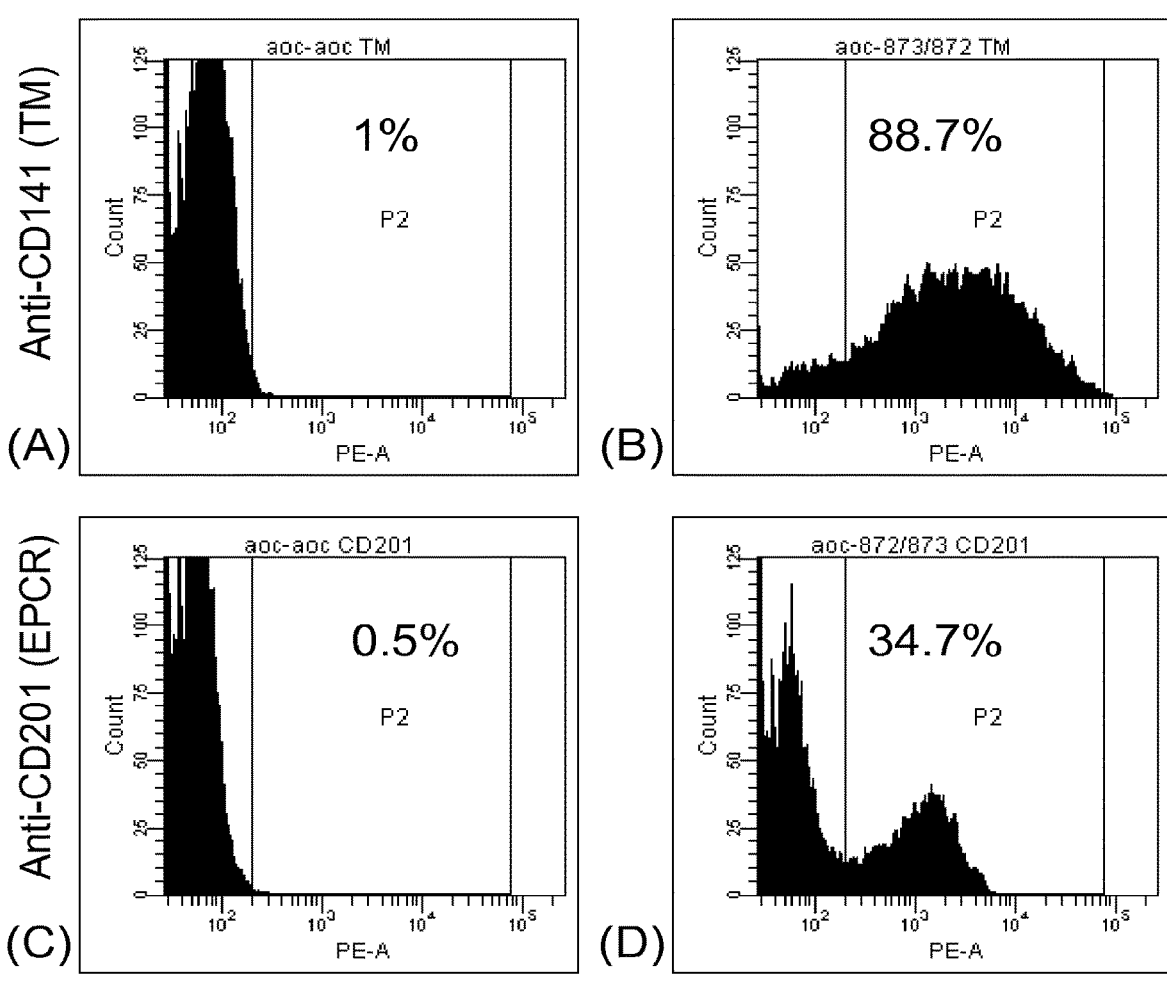
FIG. 2 shows flow cytometric analysis of transgenic protein expression in transfected porcine immortal aortic endothelial cells (AOCs). Anti-human thrombomodulin (TM) monoclonal antibody (mAb) reacted with (A), non-transfected AOCs and (B) AOC's transfected with human TM and human EPCR. Anti-human endothelial protein C receptor (EPCR) mAb reacted with (C) non-transfected AOC's and (D) AOCs transfected with human TM and human EPCR.

The immunobiology of xenotransplantation, between discordant species, has been well detailed in the pig-to-primate model (reviewed by Ekser and Cooper, 2010 Expert Rev. Clin. Immuol. 6 (2): 219-230; Li et al., Transpl Immunol. 2009 June; 21 (2): 70-4; Le Bas-Bernardet and Blancho Transpl Immunol. 2009 June; 21 (2): 60-4; Pierson et al., Xenotransplantation. 2009 September-October; 16(5): 263-80). In initial studies, wild-type pig organs transplanted into non-human primates were rejected due to the binding of natural (preformed) antibodies to the pig vascular endothelium and initiation of the complement cascade. Endothelial cells responded to this immune activation by converting from an anticoagulant to a coagulant phenotype, and HAR resulted (Robson et al., Int Arch Allergy Immunol. 1995 April; 106 (4): 305-22.). The removal of the Gal epitope from the cell surface in genetically engineered "Gal knock-out" (GTKO) pigs eliminated HAR (Kuwaki et al., Nat Med. 2005 January; 11 (1): 29-31). Subsequently, studies utilizing GTKO pigs identified further forms of xenorejection, characterized by intravascular coagulation, and thrombosis in the graft. The first, termed acute humoral xenograft rejection (AHXR) or delayed xenograft rejection (DXR), is triggered by either antibody/cell-mediated damage of the endothelium or by coagulation factor incompatibilities between the discordant species (pig and non-human primate), leading to endothelial activation. Once activated, the endothelium changes from its anticoagulant state to a procoagulant state by up regulation of von Willebrand factor and production of tissue factor leading to thrombus formation, hemorrhage, and rejection of the graft (Mohiuddin, 2007, PLOS Medicine, Vol 4 (3) p. 0429-0434). In addition to AHXR, in the absence of intense immunosuppression regimes, xenografts may undergo acute cellular rejection, characterized by T- and B-cell infiltration of the graft and T-cell activation (Ekser and Cooper, 2010). Therefore, in this challenging endothelial environment, a xenograft must be capable of preventing or dampening all of these immunological responses, to remain viable and functional. Expression of multiple transgenes, such as anticoagulants, immunosuppressant and cytoprotective transgenes, in a tissue specific manner within the porcine endothelium of a xenografts, on a GTKO genetic background, will address these multiple immunological challenges. Therefore, the present invention provides genetically engineered pigs with the GTKO genetic background plus other transgenes towards improved outcomes in organ, tissue or endothelial cell xenotransplantation. Organs, tissues and cells from GTKO pigs expressing other transgenes specifically in endothelium, will provide significant protection of the xenografted material from the recipient's immune response.

A "transgene" is a gene or genetic material that has been transferred from one organism to another. Typically, the term describes a segment of DNA containing a gene sequence that has been isolated from one organism and is introduced into a different organism. This non-native segment of DNA may retain the ability to produce RNA or protein in the transgenic organism, or it may alter the normal function of the transgenic organism's genetic code. In general, the DNA is incorporated into the organism's germ line. For example, in higher vertebrates this can be accomplished by injecting the foreign DNA into the nucleus of a fertilized ovum. When inserted into a cell, a transgene can be either a cDNA (complementary DNA) segment, which is a copy of mRNA (messenger RNA), or the gene itself residing in its original region of genomic DNA. The transgene can be a genome sequence, in particular when introduced as large clones in BACs (bacterial artificial chromosomes) or cosmid. Transgene "expression" in the context of the present specification, unless otherwise specified, means that a peptide sequence from a non-native nucleic acid is expressed in at least one cell in a host. The peptide can be expressed from a transgene that is incorporated in the host genome.

A "donor" is meant to include any non-human organism that may serve as a source of donor tissue or cells for xenotransplantation including, but not limited to, mammals, birds, chickens, reptiles, fish, and insects. The donor may be in any stage of development, including, but not limited to fetal, neonatal, young and adult. An "animal" is typically a mammal. A "mammal" is meant to include any non-human mammal, including but not limited to pigs, sheep, goats, cattle (bovine), deer, mules, horses, monkeys, dogs, cats, rats, and mice. In one embodiment of the invention, genetically altered pigs and methods of production thereof are provided. The animals of the invention are "genetically modified" or "transgenic," which means that they have a transgene, or other foreign DNA, added or incorporated, or an endogenous gene modified, including, targeted, recombined, interrupted, deleted, disrupted, replaced, suppressed, enhanced, or otherwise altered, to mediate a genotypic or phenotypic effect in at least one cell of the animal, and typically into at least one germ line cell of the animal. In some embodiments, animals may have the transgene integrated on one allele of its genome (heterozygous transgenic). In other embodiments, animals may have the transgene on two alleles (homozygous transgenic).

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs. The term ungulate as used herein refers to an adult, embryonic or fetal ungulate animal.

The terms "porcine", "porcine animal", "pig" and "swine" are generic terms referring to the same type of animal without regard to gender, size, or breed.

The "cells" "tissues" and "organs" of the invention are derived from an animal. Although the cells, tissues and organs can be derived from a mature animal, in some embodiments the cells, tissues and organs are derived from a fetal or neonatal tissue. In particular embodiments of the invention, the cells, tissues and organs, are derived from a transgenic porcine animal and in particular, a transgenic porcine that has grown to a sufficient size to be useful as a transplant donor. In certain embodiments, the animals survive past weaning age. In specific embodiments, the animals are at least six months old. In certain embodiments, the animal survives to reach breeding age. In certain embodiments, the animal is a porcine animal of at least 300 pounds. In specific embodiments, the animal is a porcine sow and has given birth at least one time.

"High" levels of expression are considered sufficient to provide a phenotype (detectable expression or therapeutic benefit). Typically a 'high' level of expression is sufficient to be capable of imparting a phenotypic or therapeutic benefit to the animal. For example, it can be capable of reducing graft rejection including hyperacute rejection (HAR), acute humoral/vascular rejection (AHXR/AVXR), and T cell-mediated cellular rejection. It was previously unknown whether anticoagulant and immunosuppressive transgenes could be expressed in porcine endothelium at levels capable of reducing these types of rejection.

The "endothelium" is an epithelium of mesoblastic origin composed of a single layer of thin flattened cells that lines internal body cavities. For example, the serous cavities or the interior of the heart contain an endothelial cells lining and the "vascular endothelium" is the endothelium that lines blood vessels. (Medline Plus, National Library of Medicine)

The term "clinically relevant immunosuppressive regimen" refers to a clinically acceptable regimen of immunosuppressant drugs provided to a patient following organ, tissue or cell transplantation of a genetically modified pig as disclosed herein. Determining clinical relevance requires a judgment call generally by the FDA balancing acceptable risk versus potential benefit such that human safety is preserved while the efficacy of the drug or treatment is maintained. In one example, the FDA can examine the number of adverse event associated with a particular regimen. An adverse event is any unfavorable and unintended sign (including an abnormal laboratory finding, for example), symptom, or disease temporally associated with the use of a medicinal product, whether or not considered related to the medical product.

As used herein, the terms "endothelial-specific", "specific transgene expression in endothelial tissue", "specifically expresses at least one transgene in endothelial tissue" and the like, it is understood that these terms refer to a transgene under control of a endothelial-specific regulatory element that allows for the restricted expression of a transgene in endothelial tissue and/or cells. The transgene function and expression is restricted to endothelial tissue and/or cells.

"Endothelial-specific regulatory element" and the like refer to a promoter, enhancer or a combination thereof wherein the promoter, enhancer or a combination thereof drives restricted expression of a transgene in endothelial tissue and/or cells. The regulatory element provides transgene function and expression restricted to endothelial tissue and/or cells.

Transgenic Animals

In one embodiment, porcine animals, organs, tissues and cells are provided that have at least four genetic modifications. Such genetic modifications can include, without limitation, additions and/or deletions of genes, including knock-outs and knock-ins, knock-down, as well as re-arrangements. In a particular embodiment, porcine animals, organs, tissues and cells are provided that have at least three or at least four genetic modifications, wherein at least one, at least two, at least three or four of the genetic modifications are transgenes and at least one, at least two, at least three or four of the transgenes are ubiquitously expressed. In a particular embodiment, porcine animals, organs, tissues and cells are provided that have at least four genetic modifications, wherein at least one genetic modification is a knock-out.

In a particular embodiment, porcine animals, tissues organs, and cells are provided that have at least one gene knocked out and express at least three transgenes. In a specific embodiment, the at least one gene is knocked out by homologous recombination.

In one embodiment, porcine animals, organs, tissues and cells are provided that have at least five genetic modifications. Such genetic modifications can include, for example, additions and/or deletions of other genes, including knock-outs and knock-ins, as well as rearrangements. In a particular embodiment, porcine animals, organs, tissues and cells are provided that have at least five genetic modifications, wherein at least one, at least two, at least three, at least four or five of the genetic modifications are transgenes and at least one, at least two, at least three, at least four or five of the transgenes are ubiquitously expressed. In a particular embodiment, porcine animals, organs, tissues and cells are provided that have at least five genetic modifications, wherein at least one genetic modification is a knock-out.

In a particular embodiment, porcine animals, tissues and cells are provided that have at least one gene knocked out and express at least four transgenes. In a specific embodiment, the at least one gene is knocked out by homologous recombination.

In one embodiment, porcine animals, organs, tissues and cells are provided that lack any expression of functional alpha 1,3 galactosyltransferase (GTKO) and express at least one transgene in endothelium. In other embodiments, GTKO animals, organs, tissues and cells are provided which express multiple transgenes in endothelium. In particular subembodiments, the animals, tissues and cells express at least one immunomodulator. In certain embodiments, the animals, organs, tissues and cells express more than one immunomodulator. In particular embodiments, GTKO animals, organs, tissues and cells are provided that express at least one immunomodulator and at least one anticoagulant transgene. In one embodiment, the immunomodulator is an immunosuppressant. In an alternate embodiment, the immunomodulator is a complement inhibitor. In a particular embodiment, expression of the immunomodulator is specific to the endothelium. In a further particular embodiment, expression of the immunosuppressant is specific to the endothelium. In a still further specific embodiment, expression of the compliment inhibitor is specific to the endothelium. In other subembodiments, the animals, organs, tissues and cells express at least one anticoagulant. In certain embodiments, the animals, organs, tissues and cells express more than one anticoagulant. In a particular embodiment, the expression of the anticoagulant is specific to the endothelium. In one subembodiment, the animals, organs, tissues and cells express at least one cytoprotective transgene. In another embodiment, the animals, organs, tissues and cells express more than one cytoprotective transgene. In one embodiment, the transgene is specifically expressed in endothelium.

In one embodiment, the present invention includes GTKO animals, organs, tissues and cells that lack any expression of functional alpha 1,3 galactosyltransferase (GTKO) and expresses at least one compliment inhibitor and at least one additional transgene selected from the group consisting of anticoagulants, immunosuppressants and cytoprotectants. In a particular embodiment, the expression of the at least one additional transgene is specific to the endothelium.

In a specific embodiment, GTKO animals, organs, tissues and cells are provided that express at least one compliment inhibitor (e.g., CD46) and at least one anticoagulant (e.g., thrombomodulin).

In another specific embodiment, GTKO animals, organs, tissues and cells are provided that express at least one compliment inhibitor (e.g., CD46) and at least two anticoagulants (e.g., thrombomodulin and CD39).

In another specific embodiment, GTKO animals, organs, tissues and cells are provided that express at least one compliment inhibitor (e.g., CD46) and at least one immunosuppressant (e.g., CTLA4).

In a still further specific embodiment, GTKO animals, organs, tissues and cells are provided that express at least one compliment inhibitor (e.g., CD46) and a cytoprotective transgene (e.g., A20).

In certain embodiments, GTKO animals, organs, tissues and cells are provided that express at least one immunosuppressant, at least one complement inhibitor and at least one anticoagulant transgene. In an further particular embodiment, GTKO animals, organs, tissues and cells are provided that express at least one immunosuppressant, at least one complement inhibitor and at least two anticoagulant transgenes. In a specific embodiment, GTKO animals, organs, tissues and cells are provided that express at least one immunosuppressant, at least one complement inhibitor and at least one anticoagulant transgenes, wherein expression of the at least one immunosuppressant and the at least one anticoagulant transgenes is specific to the endothelium. In yet another specific embodiment, GTKO animals, organs, tissues and cells are provided that express at least one immunosuppressant, at least one complement inhibitor and at least two anticoagulant transgenes, wherein expression of the at least one immunosuppressant and the at least two anticoagulant transgenes is specific to the endothelium. In one embodiment, GTKO animals, organs, tissues and cells are provided that express at least one immunomodulator, at least one anticoagulant and at least one cytoprotective transgene. In a further embodiment, GTKO animals, organs, tissues and cells are provided that express at least one immunosuppressant, at least one complement inhibitor, at least one anticoagulant transgene and at least one cytoprotective transgene. In a further particular embodiment, GTKO animals, organs, tissues and cells are provided that express at least one immunosuppressant, at least one complement inhibitor, at least two anticoagulant transgenes and at least one anti-cytoprotective transgene. In a particular embodiment, GTKO animals, organs, tissues and cells are provided that express at least one immunosuppressant, at least one complement inhibitor, at least one anticoagulant transgene and at least one cytoprotective transgene, wherein the expression of the at least one immunosuppressant and the at least one anticoagulant transgenes is specific to the endothelium. In a particular embodiment, GTKO animals, organs, tissues and cells are provided that express at least one immunosuppressant, at least one complement inhibitor, at least two anticoagulant transgenes and at least one cytoprotective transgene, wherein the expression of the at least one immunosuppressant and the at least two anticoagulant transgenes is specific to the endothelium. In a specific embodiment, the expression of the anti-apoptotic transgene is specific to the endothelium.

In one embodiment, the transgenic porcine animals described herein are viable. In another embodiment, the animals described herein are fertile. In further embodiments, the animals described herein can stably transmit some of its genetic modifications to its offspring. In still further embodiments, the animals described herein can stably transmit all of its genetic modifications to its offspring. In certain embodiments, the animals can stably transmit all of its genetic modifications to its offspring when the animals are bred naturally. In other embodiments, the multiple transgenes exhibit co-segregation to offspring. In a particular embodiment, porcine animal, organs, tissues and cells are provided with at least the following genetic modifications: lack of expression of GT, expression of a complement inhibitor, endothelial-specific expression of an anticoagulant transgene, and endothelial-specific expression of an immunosuppressant transgene. In a particular embodiment, porcine animals, organs, tissues and cells are provided with at least the following genetic modifications: lack of expression of GT, expression of a complement inhibitor, endothelial-specific expression of two anticoagulant transgenes, and expression of an immunosuppressant transgene. In another embodiment, porcine animals, organs, tissues and cells are provided with at least the following genetic modifications: lack of expression of GT, expression of a complement inhibitor, expression of a cytoprotective transgene, endothelial-specific expression of an anticoagulant transgene, and expression of an immunosuppressant transgene. In a particular embodiment, porcine animals, organs, tissues and cells are provided with at least the following genetic modifications: lack of expression of GT, expression of a complement inhibitor, expression of a cytoprotective transgene, endothelial-specific expression of two anticoagulant transgenes, and expression of an immunosuppressant transgene. In a specific embodiment, the expression of the cytoprotective transgene is also endothelium-specific. An immunomodulator can be a complement inhibitor or an immunosuppressant. In specific embodiments, the immunomodulator is a complement inhibitor. The complement inhibitor can be CD46 (or MCP). In other embodiments, the complement inhibitor is CD55, CD59 or CR1. In certain embodiments, the transgene is expressed from a ubiquitous promoter. In certain other embodiments, the transgene is expressed from a promoter active primarily in endothelium. The expression can be at any level, but in specific embodiments, the expression is at high levels. Typically a 'high' level of expression is sufficient to be capable of imparting a phenotypic or therapeutic benefit to the animal.

An immunomodulator can also be an immunosuppressant. The immunosuppressant can be capable of down-regulating a T-cell mediated response. In particular, the immunosuppressant can be CTLA4-Ig or mutants thereof. In other embodiments, the immunosuppressant transgene is a ligand that interferes with CD28 activity, such as a B7 receptor peptide or mutant thereof. In certain embodiments, the transgene is expressed from a promoter active primarily in endothelium. The expression can be at any level, but in specific embodiments, the expression is at high levels.

In other embodiments, the immunomodulator can be selected from the group that includes class II transactivators (CIITA) and mutants, including dominant negative mutants thereof (CIITA-DN), PDL1, PDL2, tumor necrosis factor-α-related apoptosis-inducing ligand (TRAIL), Fas ligand (FasL, CD95L) integrin-associated protein (CD47), HLA-E, HLA-DP, HLA-DQ, or HLA-DR. In certain other embodiments, the transgene is expressed from a promoter active primarily in endothelium. In certain embodiments, the immunomodulator transgene is expressed from a ubiquitous promoter. The expression can be at any level, but in specific embodiments, the expression is at high levels.

In one embodiments, the anticoagulant is selected from the group that includes tissue factor pathway inhibitor (TFPI), hirudin, thrombomodulin, endothelial protein C receptor (EPCR), and CD39. In a particular embodiment, the anticoagulant is thrombomodulin. In another particular embodiment, the anticoagulant is CD39. In certain other embodiments, the transgene is expressed from a promoter active primarily in endothelium. The expression can be at any level, but in specific embodiments, the expression is at high levels.

The cytoprotective transgene can be an anti-apoptotic, anti-oxidant or anti-inflammatory transgene. In certain embodiments, the cytoprotective transgene is selected from the group that includes A20, HO-1, FAT-1, catalase, and soluble TNF-alpha receptor (sTNFR1). In certain other embodiments, the transgene is expressed from a promoter active primarily in endothelial cells. The expression can be at any level, but in specific embodiments, the expression is at high levels.

In certain embodiments, the one or more immunosuppressant or anticoagulant transgenes is expressed in the endothelium of tissues of GTKO porcine animals which express high levels of CD46. In particular embodiments, porcine animals, tissues and cells are provided derived from GTKO animals that express high levels of CD46 and express thrombomodulin in endothelium. In a separate embodiment, porcine animals, tissues and cells derived from GTKO animals are provided that express high levels of CD46 and express CD39 in endothelium. In a further embodiment, porcine animals, tissues and cells derived from GTKO animals are provided that express high levels of CD46 and express CD39 and/or thrombomodulin in endothelium.

In some embodiments, the immunomodulator has the sequence of a human protein. In other embodiments, the immunomodulator has the sequence of a porcine protein. In some embodiments, the anticoagulant has the sequence of a human protein. In other embodiments, the anticoagulant has the sequence of a porcine protein. In some embodiments, the cytoprotective transgene has the sequence of a porcine protein. In another embodiment, the cytoprotective transgene has the sequence of a human protein. In particular embodiments, the porcine animal, organ, tissue or cell expresses a human CD46 transgene. In particular embodiments, the porcine animal, organ, tissue or cell expresses a human CTLA4-Ig transgene. In certain embodiments, the porcine animal, organ, tissue or cell expresses a human thrombomodulin. In certain embodiments, the porcine animal, organ, tissue or cell expresses a human CD39. In certain embodiments, the porcine animal, organ, tissue or cell expresses a human TFPI. In particular embodiments, the porcine animal, tissue or cell expresses a porcine CTLA4 transgene. In a particular embodiment, porcine animals, organs, tissues and cells are provided with at least the following genetic modifications: lack of expression of GT, expression of CD46, endothelial-specific expression of TFPI, and endothelial-specific expression of CTLA4-Ig. In another particular embodiment, porcine animals, organs, tissues and cells are provided with at least the following genetic modifications: lack of expression of GT, expression of CD46, endothelial-specific expression of TFPI, endothelial-specific expression of CD39, and endothelial-specific expression of CTLA4-Ig. In a particular embodiment, the CD46 can be a human CD46. In another particular embodiment, the human CD46 can be expressed at high levels.

In another particular embodiment, porcine animals, organs, tissues and cells are provided with at least the following genetic modifications: lack of expression of GT, expression of CD46, expression of a cytoprotective transgene, endothelial-specific expression of thrombomodulin, and endothelial-specific expression of CTLA4-Ig. In another particular embodiment, porcine animal, tissues and cells are provided with at least the following genetic modifications: lack of expression of GT, expression of CD46, expression of a cytoprotective transgene, endothelial-specific expression of thrombomodulin, endothelial-specific expression of CD39, and endothelial-specific expression of CTLA4-Ig.

In another particular embodiment, porcine animals, organs, tissues and cells are provided with at least the following genetic modifications: lack of expression of GT, expression of CD46, endothelial-specific expression of thrombomodulin and/or CD39, and expression of CIITA.

In another particular embodiment, porcine animal, tissues and cells are provided with at least the following genetic modifications: lack of expression of GT, expression of CD46, expression of DAF, endothelial-specific expression of thrombomodulin and/or CD39, and expression of CIITA.

In certain embodiments, the transgene is expressed from a promoter active primarily in endothelial cells (EC) ("endothelium specific promoters"). Endothelium specific promoters of the present invention include, but are not limited to: vascular cell adhesion molecule-1 (VCAM-1), von Willebrand factor (vWF), endothelial nitric oxide synthase (eNOS), tyrosine kinase (Tie), fms-like tyrosine kinase-1 (FIT-1), kinase domain receptor (KDR/flk-1), intercellular adhesion molecule-2 (ICAM-2) and endoglin. (For example, all reviewed (for use in adenoviral gene transfer vectors) by Beck et al., Current Gene Therapy, 2004, 4, 457-467, Table 2A.) Others promoters which can be used for expression of transgenes in the vasculature include but are not limited to CD31 (platelet endothelial cell adhesion molecule [PE-CAM]) promoter, E-selectin, Pre-Proendothelin-1 (PPE-1) Promoter (see, for example, U.S. Pat. No. 5,747,340 and US Patent Publication No. 2007/0286845), and LDL LOX-1 (White et al., Gene Ther. 2008 March; 15 (5): 340-6; which targets the arterial vasculature). CD31 (platelet endothelial cell adhesion molecule [PECAM]) promoter limits expression to endothelial cells, monocytes, and platelets and has been used to target hirudin and TFPI to activated endothelium in transgenic mice (Chen et al., Blood. 2004 Sep. 1; 104 (5): 1344-9). Also embodied herein are smooth muscle cell (SMC) promoters, which localize transgene expression in the smooth muscle layer of blood vessels, in close proximity to the vascular endothelium (for a list of SMC promoters, see for example Beck et al., see Table 2B).

In certain embodiments the promoter is an endothelium specific promoter including but not limited to the Tie-2 promoter, the ICAM-2 promoter or the PECAM promoter. The promoters of the present invention can be from a vertebrate animal, including but not limited to fish or mammalian promoters such as tilapia, human, pig, rat, or mouse. In specific embodiments, the promoter is an ICAM-2 promoter from a vertebrate animal, including but not limited to fish or mammalian promoters such as tilapia, human, pig, rat, or mouse. In specific embodiments, the promoter is the mouse Tic-2 promoter. In specific embodiments, the promoter is the porcine ICAM-2 promoter.

In certain embodiments additional regulatory elements can be incorporated into the transgene expression system, including enhancer elements. In one embodiment, the enhancer can be an endothelial-specific enhancer. The enhancers can be selected from but not limited to one of the following: Tie-2 enhancer; the ICAM-2 enhancer; the PECAM enhancer, the pdx-1 enhancer and the chicken actine enhancer. The enhancer can be, for example, a pdx-1 enhancer or a chicken actin enhancer, or can be an insulator element for example, a chicken beta-globin insulator, for enhanced expression of the transgene (Chung J H, Bell A C, Felsenfeld G., Proc Natl Acad Sci USA. 1997 Jan. 21; 94 (2): 575-80). In specific embodiments, the enhancer element used is the Tie-2 enhancer. In specific embodiments, the promoter is used in combination with an enhancer element that is a non-coding or intronic region of DNA intrinsically associated or co-localized with the promoter. Particular specific embodiments of the present invention include the: Tie-2 promoter combined with the Tic-2 enhancer; the ICAM-2 promoter combined with the ICAM-2 enhancer; the PECAM promoter with the PECAm enhancer; and/or any promoter disclosed herein combined with its intrinsically associated enhancer element.

As used herein, the terms "endothelial-specific", "specific transgene expression in endothelial tissue", "specifically expresses at least one transgene in endothelial tissue" and the like, it is understood that these terms refer to a transgene under control of an endothelial-specific regulatory element that allows for the restricted expression of a transgene in endothelial tissue and/or cells. The transgene function and expression is restricted to endothelial tissue and/or cells.

"Endothelial-specific regulatory element" and the like refer to a promoter, enhancer or a combination thereof wherein the promoter, enhancer or a combination thereof drives restricted expression of a transgene in endothelial tissue and/or cells. The regulatory element provides transgene function and expression restricted to endothelial tissue and/or cells.

In certain embodiments, the expression is restricted to endothelium and is not present in other porcine tissues. To analyze tissue specific expression, one skilled in the art can use techniques to ascertain the relative expression pattern in endothelial tissues and cells versus other tissues and cells. In one embodiment, immunohistochemistry can be used to analyze endothelial-specific expression. In another embodiment, there will be immunohistochemical staining of cells containing the transgene under control of endothelial-specific regulatory elements whereas the cells without the transgene will not exhibit the staining. In another embodiment, real-time PCR can be used to analyze endothelial-specific expression. In one embodiment, the number of copies of amplified DNA from total RNA from cells containing the transgene under control of endothelial-specific regulatory elements will be at least one logarithm higher than cells without the transgene. In another embodiment, flow cytometry can be used to analyze endothelial-specific expression. In one embodiment, fluorescence intensity from cells containing the transgene under control of endothelial-specific regulatory elements will be approximately 95-100% whereas fluorescence intensity form cells without the transgene will be approximately 0-5%.

In addition, expression can be present in fetal, neonatal, and mature tissues, each of which can be a source of donor material. In particular embodiments of the invention, the cells, and especially the endothelial cells, are derived from a transgenic porcine animal and in particular, a transgenic porcine that has grown to a sufficient size to be useful as a donor. In certain embodiments, the animals survive past weaning age. In specific embodiments, the animals are at least six months old. In certain embodiments, the animal survives to reach breeding age. In certain embodiments, the animal is a porcine animal of at least 300 pounds.

In one embodiment, a method is provided for treatment or prophylaxis of organ dysfunction including administering donor porcine tissues, organs or cells to a host suffering from organ dysfunction, wherein the porcine donor material exhibits expresses at least one anticoagulant transgene.

In another embodiment, a method is provided for treatment or prophylaxis of cornea or retina dysfunction including administering donor porcine corneal endothelial cells to a host suffering from eye disease, including cornea or retina dysfunction, wherein the porcine donor material exhibits expresses at least one anticoagulant transgene.

In one embodiment, the donor organ is a porcine heart. In another embodiment, the donor organ is a porcine kidney. In another embodiment, the donor organ is a porcine lung. In another embodiment, the donor organ in is a porcine liver. In another embodiment, the donor cells are porcine liver-derived cells, liver tissue slices; or isolated liver cells. In a particular embodiment, the donor cells are porcine hepatocytes. In a particular embodiment porcine hepatocytes or porcine liver tissue slices may be used in a medical device.

In a particular embodiment, the porcine donor cells are endothelial cells from the cornea or retina used as a graft to treat cornea or retina dysfunction.

In another particular embodiment, the donor tissues are porcine blood vessels or vascular tissues used as a graft, to treat vascular diseases or defects.

In a further particular embodiment, the porcine donor cells are endothelial cells used to seed vascular grafts, or may be used for seeding during coronary procedures, such as stenting or bypass surgery. Vascular graft materials may be allografts (human origin), or bioengineered devices, or any other material used as a vascular graft.

In other embodiments, cells provided herein can be used in re-transplant procedures.

In certain embodiments of the present invention, methods of treating or preventing organ dysfunction in primates are provided involving administration of the organs, tissues or cells of the present invention to primates in need thereof. In one embodiment, the primate is a non-human primate, in one non-limiting example, a monkey. In another embodiment, the primate is a human. In additional embodiments, the animals can also contain genetic modifications to express an immunomodulator. The immunomodulator can be a complement pathway inhibitor gene and in particular embodiments is selected from CD55, CD59, CR1 and CD46 (MCP). The complement inhibitor can be human CD46 (hCD46) wherein expression is through a mini-gene construct (See Loveland et al., Xenotransplantation, 11 (2): 171-183. 2004). The immunomodulator can also be an immunosuppressor gene that has a T-cell modulating effect-such as CTLA4-Ig, or a dominant negative inhibitor (downregulator) of class II MHC (CIITA), or other genes that modulate the expression of B-cell or T cell mediated immune function. Transgenic pigs expressing a CIITA dominant negative mutant driven by a CAG promoter have recently been produced and shown to have a down regulated SLA class II expression (after cytokine stimulation) and a reduced human T-cell response (see Hara et al., 2010 Am J Transplant. 2010 (Supplement 4); 10:187. (Abstract 503). In further embodiments, such animals can be further modified to eliminate the expression of genes which affect immune function.

In additional embodiments, the animals can also contain genetic modifications to express an anticoagulant. The anti-coagulant may include, but is not limited to, TFPI, hirudin, thrombomodulin, EPCR and CD39. In addition, the animals can be genetically modified to inhibit the expression of a CMP-Neu5Ac hydroxylase gene (see, for example, U.S. Patent Publication. 2005-0223418), the iGb3 synthase gene (see, for example, U.S. Patent Publication 2005-0155095), and/or the Forssman synthase gene (see, for example, U.S. Patent Publication 2006-0068479). In addition, the animals can be genetically modified to reduce expression of a pro-coagulant. In particular, in one embodiment, the animals are genetically modified to reduce or eliminate expression of a procoagulant gene such as the FGL2 (fibrinogen-like protein 2) (see, for example, Marsden, et al. (2003) J din Invest. 112:58-66; Ghanckar, et al. (2004) J Immunol. 172: 5693-701; Mendicino, et al. (2005) Circulation. 112:248-56; Mu, et al. (2007) Physiol Genomics. 31 (1): 53-62).

In embodiments wherein a transgene is expressed, this expression may be via a ubiquitous or tissue-specific pro-moter and may include additional regulatory elements such as enhancers, insulators, matrix attachment regions (MAR) and the like.

To achieve these additional genetic modifications, in one embodiment, cells isolated from a genetically modified pig can be further modified to contain multiple genetic modifi-cations. In some embodiments these cells can be used as donors to produce pigs with multiple genetic modifications via nuclear transfer. In other embodiments, genetically modified animals can be bred together to achieve multiple genetic modifications.

Transgenes to Target Acute Humoral Rejection

Xenografting is currently hindered by the severe and well-documented problems of rejection. This process can be divided into distinct stages, the first of which occurs within minutes of transplantation and is called "hyperacute rejec-tion" (HAR). HAR is defined by the ubiquitous presence of high titers of pre-formed natural antibodies binding to the foreign tissue. The binding of these natural antibodies to target epitopes on the donor tissue endothelium is believed to be the initiating event in HAR. This binding, within minutes of perfusion of the donor tissue with the recipient blood, is followed by complement activation, platelet and fibrin deposition, and ultimately by interstitial edema and hemorrhage in the donor organ, all of which cause rejection of the tissue in the recipient (Strahan et al. (1996) Frontiers in Bioscience 1, c34-41). The primary course of HAR in humans is the natural anti-Gal antibody, which comprises approximately 1% of antibodies in humans and monkeys.

This initial hyperacute rejection is then reinforced by the delayed vascular response (also known as acute humoral xenograft rejection (AHXR), acute vascular xenorejection (AVXR) or delayed xenograft rejection (DXR)). The lysis and death of endothelial cells during the hyperacute response is accompanied by edema and the exposure of adventitial cells, which constitutively express tissue factor (TF) on their surface. Tissue factor is thought to be pivotal in the initiation of the in vivo coagulation cascade, and its exposure to plasma triggers the clotting reactions. Thrombin and TNF-alpha become localized around the damaged tissue and this induces further synthesis and expression of TF by endothelial cells.

The environment around resting endothelial cells does not favor coagulation. Several natural coagulation inhibitors are associated with the extracellular proteoglycans of endothe-lial cells, such as tissue factor pathway inhibitor, antithrom-bin III, and thrombomodulin. The recognition of the foreign tissue by xenoreactive natural antibodies (XNAs), however, causes the loss of these molecules.

Together with the exposure and induction of tissue factor, the anticoagulant environment around endothelial cells thus becomes pro-coagulant. The vascularised regions of the xenograft thus become sites of blood clots, a characteristic of damaged tissue. Blood flow is impaired and the trans-planted organ becomes ischemic. A fuller account of delayed vascular rejection can be found in Bach et al. (1996) Immunol Today. 1996 August; 17 (8): 379-84.

The present invention provides for animals, tissues or cells that may be used in xenotransplantation to produce low to no levels of one or more of the following: HAR, AHXR/ AVXR/DXR and/or ACXR. In one embodiment, the ani-mals, tissues or cells may be used in xenotransplantation to produce low to no levels of HAR and AHXR/AVXR. In another embodiment, the animals, tissues or cells may be used in xenotransplantation to produce low to no levels of HAR, AHXR/AVXR and ACXR. As will be discussed in detail in the following sections, embodiments of the present invention include various combinations of complement regulator expression, immunosuppressor expression, antico-agulant expression, and/or partially or fully depleted func-tional αGT expression in donor tissue.

In one embodiment, porcine animals, we well as organs, tissues and cells thereof, are provided herein and express one or more transgenes. In another embodiment, porcine ani-mals, we well as organs, tissues and cells thereof, are provided herein and express one or more transgenes selected from but not limited to the following: at least two trans-genes, at least three transgenes, at least four transgenes, at least five transgenes, at least six transgenes, at least seven transgenes and at least eight transgenes. In further embodi-ments, cells from the porcine animals provided herein can elicit a decreased immune response by human lymphocytes (MLR assay) to said porcine cells. In another embodiment, cells expressing transgenes are shown to inhibit clotting and thrombosis which occurs in the xenograft environment.

Alpha 1,3 Galactosyltransferase (αGT)

As noted previously, the primary course of HAR in humans is the natural anti-galactose alpha 1,3-galactose (Gal) antibody, which comprises approximately 1% of IgG antibodies in humans and monkeys. Except for Old World monkeys, apes and humans, most mammals carry glycopro-teins on their cell surfaces that contain the Gal epitope (Galili et al., J. Biol. Chem. 263:17755-17762, 1988). Humans, apes and old world monkeys do not express Gal, but rather produce in high quantities a naturally occurring anti-Gal antibody that causes an immediate hyperacute reaction upon xenotransplantation into humans of tissues from animals carrying the Gal epitope (Sandrin et al., Proc Natl Acad Sci USA. 1993 Dec. 1; 90 (23): 11391-5, 1993; review by Sandrin and Mckenzie, Immunol Rev. 1994 October; 141:169-90).

A variety of strategies have been implemented to elimi-nate or modulate the anti-Gal humoral response caused by xenotransplantation, including enzymatic removal of the epitope with alpha-galactosidases (Stone et al., Transplan-tation 63:640-645, 1997), specific anti-gal antibody removal (Ye et al., Transplantation 58:330-337,1994), capping of the epitope with other carbohydrate moieties, which failed to eliminate αGT expression (Tanemura et al., J. Biol. Chem. 27321:16421-16425, 1998 and Koike et al., Xenotransplan-tation 4:147-153, 1997) and the introduction of complement inhibitory proteins (Dalmasso et al., Clin. Exp. Immunol. 86:31-35, 1991, Dalmasso et al. Transplantation 52:530-533 (1991)). C. Costa et al. (FASEB J 13, 1762 (1999)) reported that competitive inhibition of αGT in transgenic pigs results in only partial reduction in epitope numbers. Similarly, S. Miyagawa et al. (J. Biol. Chem 276, 39310 (2000)) reported that attempts to block expression of gal epitopes in N-acetyl-glucosaminyltransferasc III transgenic pigs also resulted in only partial reduction of gal epitopes numbers and failed to significantly extend graft survival in primate recipients.

Single allele knockouts of the αGT locus in porcine cells and live animals have been reported. Denning et al. (Nature Biotechnology 19:559-562, 2001) reported the targeted gene deletion of one allele of the αGT gene in sheep. Harrison et al. (Transgenics Research 11:143-150, 2002) reported the production of heterozygous αGT knock out somatic porcine fetal fibroblasts cells. In 2002, Lai et al. (Science 295:1089-1092, 2002) and Dai et al. (Nature Biotechnology 20:251-255, 2002) reported the production of pigs, in which one allele of the αGT gene was successfully rendered inactive. Ramsoondar et al. (Biol of Reproduc 69, 437-445 (2003)) reported the generation of heterozygous αGT knockout pigs that also express human alpha-1,2-fucosyltransferase (HT), which expressed both the HT and αGT epitopes. PCT publication No. WO 03/055302 to The Curators of the University of Missouri confirms the production of heterozygous αGT knockout miniature swine for use in xenotransplantation in which expression of functional αGT in the knockout swine is decreased as compared to the wildtype.

PCT publication No. WO 94/21799 and U.S. Pat. No. 5,821,117 to the Austin Research Institute; PCT publication No. WO 95/20661 to Bresatec; and PCT publication No. WO 95/28412, U.S. Pat. Nos. 6,153,428, 6,413,769 and US publication No. 2003/0014770 to BioTransplant, Inc. and The General Hospital Corporation provide a discussion of the production of αGT negative porcine cells based on the cDNA of the αGT gene.

A recent, major breakthrough in the field of xenotransplantation was the production of the first live pigs lacking any functional expression of αGT (Phelps et al. Science 299:411-414 (2003); see also PCT publication No. WO 04/028243 by Revivicor, Inc. and PCT Publication No. WO 04/016742 by Immerge Biotherapeutics, Inc.).

In one embodiment, animals, tissues and cells are provided that lack any expression of functional αGT (GTKO) and express at least one additional transgene in endothelium. The additional transgene is typically selected from: 1) an immunomodulator including a complement inhibitor (i.e. CD46 (MCP), CD55, CD59, CR1 and the like) or an immunosuppressor (i.e. CTLA-4, B7 and the like) or 2) an anticoagulant (i.e. TFPI, hirudin, thrombomodulin, EPCR, CD39 and the like). In other embodiments, animals, tissue and cells are provided that lack any expression of functional αGT and express both at least one immunomodulator and at least one anticoagulant in endothelium. Animals, tissues and cells with a reduced level of expression of functional αGT that concurrently express at least one of the following in endothelium: 1) an immunomodulator including a complement inhibitor (i.e. CD46, CD55, CD59, CR1 and the like) or an immunosuppressor (i.e. CTLA-4, B7 and the like) or 2) an anticoagulant (i.e. TFPI, hirudin, thrombomodulin, EPCR, CD39 and the like) are also included in this invention. In some embodiments, animals, tissue and cells are provided that have a reduced level of expression of functional αGT and express both at least one immunomodulator and at least one anticoagulant in endothelium. The complete or reduced level of expression of functional αGT may be achieved by any means known to one of skill in the art. In one aspect of the present invention, porcine animals are provided in which one allele of the αGT gene is inactivated via a genetic targeting event. In another aspect of the present invention, porcine animals are provided in which both alleles of the αGT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In embodiments of the present invention, the alleles of the αGT gene are rendered inactive, such that the resultant αGT enzyme can no longer generate Gal on the cell surface. In one embodiment, the αGT gene can be transcribed into RNA, but not translated into protein. In another embodiment, the αGT gene can be transcribed in a truncated form. Such a truncated RNA can either not be translated or can be translated into a nonfunctional protein. In an alternative embodiment, the αGT gene can be inactivated in such a way that no transcription of the gene occurs. In a further embodiment, the αGT gene can be transcribed and then translated into a nonfunctional protein. In some embodiments, the expression of active αGT can be reduced by use of alternative methods, such as those targeting transcription or translation of the gene. For example, the expression can be reduced by use of antisense RNA or siRNA targeting the native αGT gene or an mRNA thereof. In other embodiments, site specific recombinases are used to target a region of the genome for recombination. Examples of such systems are the CRE-lox system and the Flp-Frt systems.

Pigs that possess two inactive alleles of the αGT gene are not naturally occurring. It was previously discovered that while attempting to knockout the second allele of the αGT gene through a genetic targeting event, a point mutation was identified, which prevented the second allele from producing functional αGT enzyme.

Thus, in another aspect of the present invention, the αGT gene can be rendered inactive through at least one point mutation. In one embodiment, one allele of the αGT gene can be rendered inactive through at least one point mutation. In another embodiment, both alleles of the αGT gene can be rendered inactive through at least one point mutation. In one embodiment, this point mutation can occur via a genetic targeting event. In another embodiment, this point mutation can be naturally occurring. In a further embodiment, mutations can be induced in the αGT gene via a mutagenic agent.

In one specific embodiment the point mutation can be a T-to-G mutation at the second base of exon 9 of the αGT gene. Pigs carrying a naturally occurring point mutation in the αGT gene allow for the production of αGT-deficient pigs free of antibiotic-resistance genes and thus have the potential to make a safer product for human use. In other embodiments, at least two, at least three, at least four, at least five, at least ten or at least twenty point mutations can exist to render the αGT gene inactive. In other embodiments, pigs are provided in which both alleles of the αGT gene contain point mutations that prevent any expression of functional αGT enzyme. In a specific embodiment, pigs are provided that contain the T-to-G mutation at the second base of exon 9 in both alleles of the αGT gene.

Another aspect of the present invention provides a porcine animal, in which both alleles of the αGT gene are inactivated, whereby one allele is inactivated by a genetic targeting event and the other allele is inactivated via a mutation. In one embodiment, a porcine animal is provided, in which both alleles of the αGT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the αGT gene are inactivated, whereby one allele is inactivated via a targeting construct directed to Exon 9 and the other allele is inactivated due to presence of a T-to-G point mutation at the second base of exon 9.

Immunomodulators

Immunomodulators can be complement regulators and immunosuppressants.

(i) Complement Regulators

Complement is the collective term for a series of blood proteins and is a major effector mechanism of the immune system. Complement activation and its deposition on target structures can lead to direct complement-mediated cell lysis or can lead indirectly to cell or tissue destruction due to the generation of powerful modulators of inflammation and the recruitment and activation of immune effector cells. Complement activation products that mediate tissue injury are generated at various points in the complement pathway. Inappropriate complement activation on host tissue plays an important role in the pathology of many autoimmune and inflammatory diseases, and is also responsible for many disease states associated with bioincompatibility, e.g. post-cardiopulmonary inflammation and transplant rejection. Complement deposition on host cell membranes is prevented by complement inhibitory proteins expressed at the cell surface.

The complement system comprises a collection of about 30 proteins and is one of the major effector mechanisms of the immune system. The complement cascade is activated principally via either the classical (usually antibody-dependent) or alternative (usually antibody-independent) pathways. Activation via either pathway leads to the generation of C3 convertase, which is the central enzymatic complex of the cascade. C3 convertase cleaves serum C3 into C3a and C3b, the latter of which binds covalently to the site of activation and leads to the further generation of C3 convertase (amplification loop). The activation product C3b (and also C4b generated only via the classical pathway) and its breakdown products are important opsonins and are involved in promoting cell-mediated lysis of target cells (by phagocytes and NK cells) as well as immune complex transport and solubilization. C3/C4 activation products and their receptors on various cells of the immune system are also important in modulating the cellular immune response. C3 convertases participate in the formation of C5 convertase, a complex that cleaves C5 to yield C5a and C5b. C5a has powerful proinflammatory and chemotactic properties and can recruit and activate immune effector cells. Formation of C5b initiates the terminal complement pathway resulting in the sequential assembly of complement proteins C6, C7, C8 and (C9) n to form the membrane attack complex (MAC or C5b-9). Formation of MAC in a target cell membrane can result in direct cell lysis, but can also cause cell activation and the expression/release of various inflammatory modulators.

There are two broad classes of membrane complement inhibitor: inhibitors of the complement activation pathway (inhibit C3 convertase formation), and inhibitors of the terminal complement pathway (inhibit MAC formation). Membrane inhibitors of complement activation include complement receptor 1 (CR1), decay-accelerating factor (DAF or CD55) and membrane cofactor protein (MCP or CD46). They all have a protein structure that consists of varying numbers of repeating units of about 60-70 amino acids termed short consensus repeats (SCR) that are a common feature of C3/C4 binding proteins. Rodent homologues of human complement activation inhibitors have been identified. The rodent protein Cr1 is a widely distributed inhibitor of complement activation that functions similar to both DAF and MCP. Rodents also express DAF and MCP, although Cr1 appears to be functionally the most important regulator of complement activation in rodents. Although there is no homolog of Cr1 found in humans, the study of Cr1 and its use in animal models is clinically relevant.

Control of the terminal complement pathway and MAC formation in host cell membranes occurs principally through the activity of CD59, a widely distributed 20 kD glycoprotein attached to plasma membranes by a glucosylphosphatidylinositol (GPI) anchor. CD59 binds to C8 and C9 in the assembling MAC and prevents membrane insertion.

Host cells are protected from their own complement by membrane-bound complement regulatory proteins like DAF, MCP and CD59. When an organ is transplanted into another species, natural antibodies in the recipient bind the endothelium of the donor organ and activate complement, thereby initiating rapid rejection. It has previously been suggested that, in contrast to human cells, those of the pig are very susceptible to human complement, and it was thought that this was because pig cell-surface complement regulatory proteins are ineffective against human complement. When an organ is transplanted into another species, natural antibodies in the recipient bind the endothelium of the donor organ and activate complement, thereby initiating rapid rejection. Several strategies have been shown to prevent or delay rejection, including removal of IgM natural antibodies and systemic decomplementation or inhibition of complement using sCR1, heparin or C1 inhibitor.

An alternative approach to the problem of rejection is to express human, membrane-bound, complement-regulatory molecules in transgenic pigs. Transgenic pigs expressing decay acceleration factor DAF (CD55), membrane co-factor protein MCP (CD46) and membrane inhibitor of reactive lysis, MIRL (CD59) have been generated. (see Klymium et al. Mol Reprod Dev (2010) 77:209-221). These human inhibitors have been shown to be abundantly expressed on porcine vascular endothelium. Ex vivo perfusion of hearts from control animals with human blood caused complement-mediated destruction of the organ within minutes, whereas hearts obtained from transgenic animals were refractory to complement and survived for hours.

The rationale for expressing human complement regulatory proteins in pig organs to "humanize" them as outlined above is based on the assumption that endogenous pig regulatory proteins are inefficient at inhibiting human complement and thus will contribute little to organ survival in the context of xenotransplantation. U.S. Pat. No. 7,462, 466 to Morgan et al. describes the isolation and characterization of porcine analogues of several of the human complement regulatory proteins (CRP). The studies illustrated that pig organs expressing human complement regulatory protein molecules were resistant to complement damage not because they expressed human CRP molecules, but because they expressed greatly increased amounts of functional CRP molecules. Morgan et al. found that increased expression of porcine CRP could be equally effective in protecting the donor organ from complement damage leading to hyperacute rejection as donor organs expressing human complement regulatory proteins.

CD46 has been characterized as a protein with regulatory properties able to protect the host cell against complement mediated attacks activated via both classical and alternative pathways (Barilla-LaBarca, M. L. et al., J. Immunol. 168, 6298-6304 (2002)). hCD46 may offer protection against complement lysis during inflammation and humoral rejection mediated by low levels of natural or induced anti-Gal or anti-nonGal antibodies. Transgenic pigs with the combination of GTKO and expression of CD46 provided prolonged survival and function of xenograft hearts (pig-to baboon) for up to 8 months without any evidence of immune rejection (Mohiuddin et al., Abstract TTS-1383. Transplantation 2010; 90 (suppl): 325).

In one embodiment of the present invention, animals, organs, tissues and cells are provided that express at least one complement regulator and either lack any expression of functional αGT or express at least one of the following in endothelium: 1) an immunosuppressor (i.e. CTLA-4, B7 and the like) or 2) an anticoagulant (i.e. TFPI, hirudin, thrombomodulin, EPCR, CD39 and the like).

In other embodiments, animals, organs, tissue and cells are provided that express at least one complement regulator, lack any expression of functional αGT and express at least one of the following in endothelium: 1) an immunosuppressor (i.e. CTLA-4, B7 and the like) or 2) an anticoagulant (i.e. TFPI, hirudin, thrombomodulin, EPCR, CD39 and the like).

In still further embodiments, animals, organs, tissue and cells are provided that express at least one complement regulator, lack any expression of functional αGT, express at least one immunosuppressor (i.e. CTLA-4, B7 and the like), and express at least one anticoagulant (i.e. TFPI, hirudin, thrombomodulin, EPCR, CD39 and the like) in endothelium. In some embodiments, the complement regulator may be a complement inhibitor. In further embodiments, the complement inhibitor may be a membrane complement inhibitor. The membrane complement inhibitor may be either an inhibitor of the complement activation pathway (inhibit C3 convertase formation) or an inhibitor of the terminal complement pathway (inhibit MAC formation). Membrane inhibitors of complement activation include complement receptor 1 (CR1), decay-accelerating factor (DAF or CD55), membrane cofactor protein (MCP or CD46) and the like. Membrane inhibitors of the terminal complement pathway may include CD59 and the like. In instances where complement regulators are expressed, two or more different complement regulators may be expressed.

In some embodiments of the present invention, the complement regulators are human complement regulators. In other embodiments, the complement regulators are porcine complement regulators.

In a particular embodiment, the compliment inhibitor (e.g., CD46 or DAF) is expressed in every cell where it would normally be expressed. In another embodiment, the compliment inhibitor is expressed ubiquitously.

In one embodiment, the animals, organs, tissues or cells according to the present invention, can be modified to transgenically express the one or more complement regulators. The animals, organs, tissues or cells can be modified to express a complement regulator peptide, a biologically active fragment or derivative thereof. In one embodiment, the complement regulator peptide is the full length complement regulator. In a further embodiment, the complement regulator peptide can contain less than the full length complement regulator protein.

Any human or porcine complement regulator sequences or biologically active portion or fragment thereof known to one skilled in the art can be according to the compositions and methods of the present invention. In additional embodiments, any consensus complement regulator peptide can be used according to the present invention. In another embodiment, nucleic acid and/or peptide sequences at least 80%, 85%, 90% or 95% homologous to the complement regulator peptides and nucleotide sequences described herein. In further embodiments, any fragment or homologous sequence that exhibits similar activity as complement regulator can be used.

(ii) Immunosuppressants

An "immunosuppressant" transgene is capable of down-regulating an immune response. For any type of transplantation procedure, a balance between efficacy and toxicity is a key factor for its clinical acceptance.

Biological agents that block key T cell costimulatory signals, in particular the CD28 pathway, have potential to protect xenografts. Examples of agents that block the CD28 pathway include but are not limited to soluble CTLA4 including mutant CTLA4 molecules.

T-cell activation is involved in the pathogenesis of transplant rejection. Activation of T-cells requires at least two sets of signaling events. The first is initiated by the specific recognition through the T-cell receptor of an antigenic peptide combined with major histocampatibility complex (MHC) molecules on antigen presenting cells (APC5). The second set of signals is antigen nonspecific and is delivered by T-cell costimulatory receptors interacting with their ligands on APCs. In the absence of costimulation, T-cell activation is impaired or aborted, which may result in an antigen specific unresponsive state of clonal anergy, or in deletion by apoptotic death. Hence, the blockade of T-cell costimulation may provide an approach for suppressing unwanted immune responses in an antigen specific manner while preserving normal immune functions. (Dumont, F. J. 2004 Therapy 1, 289-304).

Of several T cell costimulatory pathways identified to date, the most prominent is the CD28 pathway. CD28, a cell surface molecule expressed on T-cells, and its counter receptors, the B7.1 (CD80) and B7.2 (CD86) molecules, present on dendritic cells, macrophages, and B-cells, have been characterized and identified as attractive targets for interrupting T-cell costimulatory signals. A second T-cell surface molecule homologous to CD28 is known as cytoxic T-lymphocyte associated protein (CTLA4). CTLA4 is a cell surface signaling molecule, but contrary to the actions of CD28, CTLA4 negatively regulates T cell function. CTLA4 has 20-fold higher affinity for the B7 ligands than CD28. The gene for human CTLA4 was cloned in 1988 and chromosomally mapped in 1990 (Dariavach et al., Eur. J. Immunol. 18:1901-1905 (1988); Lafage-Pochitaloff et al., Immunogenetics 31:198-201 (1990); U.S. Pat. No. 5,977,318).

The CD28/B7 pathway has become an attractive target for interrupting T cell costimulatory signals. The design of a CD28/B7 inhibitor has exploited the endogenous negative regulator of this system, CTLA4. A CTLA4-immunoglobulin (CTLA4-Ig) fusion protein has been studied extensively as a means to inhibit T cell costimulation. A difficult balance must be reached with any immunosuppressive therapy; one must provide enough suppression to overcome the disease or rejection, but excessive immunosuppression will inhibit the entire immune system. The immunosuppressive activity of CTLA4-Ig has been demonstrated in preclinical studies of animal models of organ transplantation and autoimmune disease. In certain embodiments, LEA29Y is substituted for CTLA4 when CTLA4 is embodied as the immunomodulator of the present invention.

Soluble CTLA4 has recently been tested in human patients with kidney failure, psoriasis and rheumatoid arthritis and has been formulated as a drug developed by Bristol-Myers Squibb (Abatacept, soluble CTLA4-Ig) that has been approved for the treatment of rheumatoid arthritis. This drug is the first in the new class of selective T cell costimulation modulators. Bristol-Myers Squibb is also conducting Phase II clinical trials with Belatacept (LEA29Y) for allograft kidney transplants. LEA29Y is a mutated form of CTLA4, which has been engineered to have a higher affinity for the B7 receptors than wild-type CTLA4, fused to immunoglobulin. Repligen Corporation is also conducting clinical trials with its CTLA4-Ig for idiopathic thrombocytopenia purpura. US patent U5730403 entitled "Methods for protecting allogeneic islet transplant using soluble CTLA4 mutant molecules", describes the use of soluble CTLA4-Ig and CTLA4 mutant molecules to protect allogencic islet transplants. Although CTLA-4 from one organism is able to bind to B7 from another organism, the highest avidity is found for allogeneic B7. Thus, while soluble CTLA-4 from the donor organism can thus bind to both recipient B7 (on normal cells) and donor B7 (on xenotransplanted cells), it preferentially binds B7 on the xenograft. Thus in the embodiments of the invention comprising porcine animals or cells for xenotransplantation, porcine CTLA4 is typical. PCT Publication No. WO 99/5 7266 by Imperial College describes a porcine CTLA4 sequence and the administration of soluble CTLA4-Ig for xenotransplantation therapy. Vaughn A. et al., J Immunol (2000) 3175-3181, describes binding and function of soluble porcine CTLA4-Ig. Porcine CTLA4-Ig binds porcine (but not human) B7, blocking CD28 on recipient T cells and rendering these local T cells anergic without causing global T cell immunosuppression (see Mirenda et. al., Diabetes 54:1048-1055, 2005).

To date, much of the research on CTLA4-Ig as an immunosuppressive agent has focused on administering soluble forms of CTLA4-Ig to the patient. Transgenic mice engineered to express CTLA4-Ig have been created and subject to several lines of experimentation. Ronchese et al. examined immune system function generally after expression of CTLA4 in mice (Ronchese et al. J Exp Med (1994) 179:809; Lane et al. J Exp Med. (1994) March 1; 179 (3): 819). Sutherland et al. (Transplantation. 2000 69 (9): 1806-12) described the protective effect of CTLA4-lg secreted by transgenic fetal pancreas allografts in mice to test the effects of transgenically expressed CTLA4-Ig on allogenic islet transplantation. Lui et al. (J Immunol Methods 2003 277: 171-183) reported the production of transgenic mice that expressed CTLA4-Ig under control of a mammary specific promoter to induce expression of soluble CTLA4-Ig in the milk of transgenic animals for use as a bioreactor.

PCT Publication No. WO 01/30966 by Alexion Pharmaceuticals Inc. describes chimeric DNA constructs containing the T cell inhibitor CTLA-4 attached to the complement protein CD59, as well as transgenic porcine cells, tissues, and organs containing the same. PCT Publication No. WO2007035213 (Revivicor) describes transgenic porcine animals that have been genetically modified to express CTLA4-Ig.

Although the development of CTLA4-Ig expressing animals has been suggested, these animals are severely immunocompromised. Recently, pigs produced by Revivicor, Inc. expressing CTLA4-Ig ubiquitously using a CAG (ubiquitous) enhancer/promoter were found to have an immunocompromised phenotype and were not viable in a typical husbandry environment (Phelps et al., 2009 Xenotransplantation. November-December; 16 (6): 477-85. Therefore there is a need to express such immunosuppressant transgenes in a tissue specific manner, such as in the endothelium of a xenograft, where high but localized levels of protein expression are possible, without any resulting phenotypic problems in the transgenic animal.

Additional immunomodulators, and in particular immunosuppressors can be expressed in the animals, tissues or cells. For example, genes which have been inactivated in mice to produce an immuno compromised phenotype, can be cloned and disrupted by gene targeting in pigs. Some genes which have been targeted in mice and may be targeted to produce immuno compromised pigs include beta 2-microglobulin (MHC class I deficiency, Koller et al., Science, 248:1227-1230), TCR alpha, TCR beta (Mombaerts et al., Nature, 360:225-231), RAG-1 and RAG-2 (Mombaerts et al., (1992) Cell 68, 869-877, Shinkai, et al., (1992) Cell 68, 855-867, U.S. Pat. No. 5,859,307).

In one embodiment, the animals, organs, tissues, or cells according to the present invention, can be modified to transgenically express a cytoxic T-lymphocyte associated protein 4-immunoglobin (CTLA4). The animals or cells can be modified to express CTLA4 peptide or a biologically active fragment (e.g., extracellular domain, truncated form of the peptide in which at least the transmembrane domain has been removed) or derivative thereof. The peptide may be, e.g., human or porcine. The CTLA4 peptide can be mutated. Mutated peptides may have higher affinity than wildtype for porcine and/or human B7 molecules. In one specific embodiment, the mutated CTLA4 can be CTLA4 (Glu104, Tyr29). The CTLA4 peptide can be modified such that it is expressed intracellularly. Other modifications of the CTLA4 peptide include addition of an endoplasmic reticulum retention signal to the N or C terminus. The endoplasmic reticulum retention signal may be, e.g., the sequence KDEL. The CTLA4 peptide can be fused to a peptide dimerization domain or an immunoglobulin (Ig) molecule. The CTLA4 fusion peptides can include a linker sequence that can join the two peptides. In another embodiment, animals lacking expression of functional immunoglobulin, produced according to the present invention, can be administered a CTLA4 peptide or a variant thereof (pCTLA4-Ig, or hCTLA4-Ig (Abatacept/Orencia, or Belatacept) as a drug to suppress their T-cell response.

In one embodiment, the CTLA4 peptide is the full length CTLA4. In a further embodiment, the CTLA4 peptide can contain less than the full length CTLA4 protein. In one embodiment, the CTLA4 peptide can contain the extracellular domain of a CTLA-4 peptide. In a particular embodiment, the CTLA4 peptide is the extracellular domain of CTIA4. In still further embodiments, the present invention provides mutated forms of CTLA4. In one embodiment, the mutated form of CTLA4 can have higher affinity than wild type for porcine and/or human B7. In one specific embodiment, the mutated CTLA4 can be human CTLA4 (Glu104, Tyr29).

In one embodiment, the CTLA4 can be a truncated form of CTLA4, in which at least the transmembrane domain of the protein has been removed. In another embodiment, the CTLA4 peptide can be modified such that it is expressed intracellularly. In one embodiment, a golgi retention signal can be added to the N or (terminus of the CTLA4 peptide. In one embodiment, the golgi retention signal can be the sequence KDEL, which can be added to the C or N terminal of the CTIA4 peptide. In further embodiments, the CTLA4 peptide can be fused to a peptide dimerization domain. In one embodiment, the CTLA4 peptide can be fused to an immunoglobulin (Ig). In another embodiment, the CTLA4 fusion peptides can include a linker sequence that can join the two peptides.

Any human CTLA4 sequences or biologically active portion or fragment thereof known to one skilled in the art can be according to the compositions and methods of the present invention. Non-limiting examples include, but are not limited to the following Genbank accession numbers that describe human CTLA4 sequences: NM005214.2; BC074893.2; BC074842.2; AF414120.1; AF414120; AY402333; AY209009.1; BC070162.1; BC069566.1; L15006.1; AF486806.1; AC010138.6; AJ535718.1; AF225900.1; AF225900; AF411058.1; M37243.1; U90273.1; and/or AF316875.1. Further nucleotide sequences encoding CTLA4 peptides can be selected from those including, but not limited to the following Genbank accession numbers from the EST database: CD639535.1; A1733018.1; BM997840.1; BG536887.1; BG236211.1; BG058720.1; A1860i99.1; AW207094.1; AA210929.1; A1791416.1; BX113243.1; AW515943.1; BE837454.1; AA210902.1; BF329809.1; A1819438.1; BE837501.1; BE837537.1; and/or AA873138.1.

In additional embodiments, any consensus CTLA4 peptide can be used according to the present invention. In another embodiment, nucleic acid and/or peptide sequences at least 80%, 85%, 90% or 95% homologous to the native CTLA4 peptides and nucleotide sequences. In further embodiments, any fragment or homologous sequence that exhibits similar activity as CTLA4 can be used.

In other embodiments, the amino acid sequence which exhibits T cell inhibitory activity can be amino acids 38 to 162 of the porcine CTLA4 sequence or amino acids 38 to 161 of the human CTLA4 sequence (see, for example, PCT Publication No. WO 01/30966). In one embodiment, the portion used should have at least about 25% and preferably at least about 50% of the activity of the parent molecule.

In other embodiments, the CTLA4 nucleic acids and peptides of the present invention can be fused to immunoglobulin genes and molecules or fragments or regions thereof. Reference to the CTLA4 sequences of the present invention include those sequences fused to immunoglobulins.

In one embodiment, the Ig can be a human Ig. In another embodiment, the Ig can be IgG, in particular, IgG1. In another embodiment, the Ig can be the constant region of IgG. In a particular embodiment, the constant region can be the Cγ1 chain of IgG1. In one particular embodiment of the present invention, the extracellular domain of porcine CTLA4 can be fused to human Cγ1 Ig. In another particular embodiment, the extracellular domain of human CTLA4 can be fused to IgG1 or IgG4. In a further particular embodiment, the extracellular domain of mutated CTLA4 (Glu 104, Tyr 29) can be fused to IgG1.

(iii) Other Immunomodulators

Other immunodulators that can be used include class II transactivators (CIITA) and mutants thereof, PDL1, PDL2, tumor necrosis factor-α-related apoptosis-inducing ligand (TRAIL), Fas ligand (FasL, CD95L) integrin-associated protein (CD47), HLA-E, HLA-DP, HLA-DQ, or HLA-DR.

(a) CIITA: The class II transactivator (CIITA) is a bi- or multifunctional domain protein that acts as a transcriptional activator and plays a critical role in the expression of MHC class II genes. It has been previously demonstrated that a mutated form of the human CIITA gene, coding for a protein lacking the amino terminal 151 amino acids, acts as a potent dominant-negative suppressor of HLA class II expression (Yun et al., Int Immunol. 1997 October; 9 (10): 1545-53). Porcine MHC class II antigens are potent stimulators of direct T-cell recognition by human CD4+ T cells and are, therefore, likely to play an important role in the rejection responses to transgenic pig donors in clinical xenotransplantation. It was reported that one mutated human CIITA construct was effective in pig cells, markedly suppressing IFN [gamma]-induced as well as constitutive porcine MHC class II expression. Moreover, stably transfected porcine vascular endothelial cell lines carrying mutated human CIITA constructs failed to stimulate direct T-cell xenorecognition by purified human CD4+ T cells (Yun et al., Transplantation. 2000 Mar. 15; 69 (5): 940-4). Organs, tissues and cells from CIITA-DN transgenic animals could induce a much reduced T-cell rejection responses in human recipients. In combination with other transgenes, transgenic expression of a mutated CIITA might enable long-term xenograft survival with clinically acceptable levels of immunosuppression. In one embodiment, a human CIITA can be used. In particular, a human CIITA-DN. In another embodiment, a porcine CIITA can be used. In particular, a porcine CITTA-DN.

(b) PDL1, PDL2: Typical costimulatory molecules for T-cell activation are CD80/86 or CD40. In addition to these positive costimulatory pathways over the past several years, new costimulatory pathways that mediate negative signals and are important for the regulation of T-cell activation have been found. One of these newer pathways is the pathway consisting of Programmed death 1 (PD-1) receptor and its ligands, PD-L1 and PD-L2. The PD-1 receptor is not expressed in resting cells but is upregulated after T and B cell activation. PD-1 contains a cytoplasmatic immunoreceptor tyrosine-based switch motif and binding of PD-L1 or PD-L2 to PD-1 leads to inhibitory signals in T cells. Recent data suggest that PD1/PDLigand pathways may play a role in the control of T-cell subsets exhibiting regulatory activity. In mice, PD-1 signals have been shown to be required for the suppressive activity of regulatory T cells (Treg) and the generation of adaptive Treg. These observations suggest that PD-1/PDLig and interactions do not only inhibit T-cell responses but may also provoke immunoregulation. Several lines of evidence demonstrate that PD-1/PDLigand pathways can control engraftment and rejection of allografts implying that these molecules are interesting targets for immunomodulation after organ transplantation. Indeed, prolongation of allograft survival could be obtained by PDL1Ig gene transfer to donor hearts in a rat transplantation model. Moreover, enhancing PD-1 signaling by injection of PD-L1Ig has also been reported to protect grafts from rejection in mice. Recent data also show that overexpression of PD-L1IG on islet grafts in mice can partially prolong islet graft survival. Transgenic expression of human PD-L1 or PD-L2 in pig cells and tissues should reduce early human anti-pig T-cell responses initiated via the direct route of sensitization (Plege et al., Transplantation. 2009 Apr. 15; 87 (7): 975-82). By the induction of Treg it might also be possible to control T cells sensitized to the xenograft through the indirect route that is required to achieve long-lasting tolerance.

(c) TRAIL/Fas L: Expression of apoptosis inducing ligands, such as Fas ligand (FasL, CD95L) or tumor necrosis factor-α-related apoptosis-inducing ligand (TRAIL, Apo-2L) may eliminate T cells attacking a xenograft. TRAIL is a type II membrane protein with an extracellular domain homologous to that of other tumor necrosis factor family members showing the highest amino acid identity to FasL (28%). TRAIL exerts its apoptosis-inducing action preferentially on tumor cells. In normal cells, binding of TRAIL receptors does not lead to cell death. Recent studies have shown that the cytotoxic effects of immune cells, including T cells, natural killer cells, macrophages, and dendritic cells, are mediated at least partly by TRAIL. Expression of human TRAIL, in transgenic pigs may provide a reasonable strategy for protecting pig tissues against cell-mediated rejection after xenotransplantation to primates. Stable expression of human TRAIL has been achieved in transgenic pigs and TRAIL expressed has been shown to be biologically functional in vitro (Klose et al., Transplantation. 2005 Jul. 27; 80 (2): 222-30).

(d) CD47: CD47, known as integrin-associated protein, is a ubiquitously expressed 50-kDa cell surface glycoprotein that serves as a ligand for signal regulatory protein (SIRP)α (also known as CD172a, SHPS-1), an immune inhibitory receptor on macrophages. CD47 and SIRPα constitute a cell-cell communication system (the CD47-SIRPα system) that plays important roles in a variety of cellular processes including cell migration, adhesion of B cells, and T cell activation. In addition, the CD47-SIRPα system is implicated in negative regulation of phagocytosis by macrophages. CD47 on the surface of several cell types (i.e., erythrocytes, platelets, or leukocytes) can protect against phagocytosis by macrophages by binding to the inhibitory macrophage receptor SIRPα. The role of CD47-SIRPα interactions in the recognition of self and inhibition of phagocytosis has been illustrated by the observation that primary, wild-type mouse macrophages rapidly phagocytose unopsonized RBCs obtained from CD47-deficient mice but not those from wild-type mice. It has also been reported that through its SIRPα receptors, CD47 inhibits both Fcγ and complement receptor-mediated phagocytosis. It has been demonstrated that porcine CD47 does not induce SIRPα tyrosine phosphorylation in human macrophage-like cell line, and a soluble human CD47-Fc fusion protein inhibits the phagocytic activity of human macrophages toward porcine cells. It was also indicated that manipulation of porcine cells for expression of human CD47 radically reduces the susceptibility of the cells to phagocytosis by human macrophages (Ide et al., Proc Natl Acad Sci USA. 2007 Mar. 20; 104 (12): 5062-6). Expression of human CD47 on porcine cells could provide inhibitory signaling to SIRPα on human macrophages, providing an approach to preventing macrophage-mediated xenograft rejection.

(e) NK Cell Response. HLA-E/Beta 2 microglobulin and HLA-DP. HLA-DQ, HLA-DR: Human natural killer (NK) cells represent a potential hurdle to successful pig-to-human xenotransplantation because they infiltrate pig organs perfused with human blood ex vivo and lyse porcine cells in vitro both directly and, in the presence of human serum, by antibody-dependent cell-mediated cytotoxicity. NK cell autoreactivity is prevented by the expression of major histocompatibility complex (MHC) class I ligands of inhibitory NK receptors on normal autologous cells. The inhibitory receptor CD94/NKG2A that is expressed on a majority of activated human NK cells binds specifically to human leukocyte antigen (HLA)-E. The nonclassical human MHC molecule HLA-E is a potent inhibitory ligand for CD94/NKG2A-bearing NK cells and, unlike classical MHC molecules, does not induce allogeneic T-cell responses. HLA-E is assembled in the endoplasmic reticulum and transported to the cell surface as a stable trimeric complex consisting of the HLA-E heavy chain, β2-microglobulin (β 2m), and a peptide derived from the leader sequence of some MHC class I molecules. The expression of HLA-E has been shown to provide partial protection against xenogeneic human NK cell cytotoxicity (Weiss et al., Transplantation. 2009 Jan. 15; 87 (1): 35-43). Transgenic expression of HLA-E on pig organs has the potential to substantially alleviate human NK cell-mediated rejection of porcine xenografts without the risk of allogeneic responses. In addition, transgenic pigs carrying other HLA genes have been successfully generated with the goal of "humanizing" porcine organs, tissues, and cells (Huang et al., Proteomics. 2006 November; 6 (21): 5815-25, see also U.S. Pat. No. 6,639,122).

Anticoagulants

In certain embodiments of the present invention, anticoagulant transgenes can be introduced into porcine animals. Such transgenes can be expressed specifically in the porcine endothelium. In one embodiment of the current invention, the Tic-2 enhancer and promoter can be used. The Tie-2 enhancer and promoter have been shown to provide uniform vascular-endothelial-cell-specific gene expression in embryonic and adult transgenic mice (Schlaeger et al., 1997 Proc Natl Acad Sci. April 1; 94 (7): 3058-63). In one example, the Tie-2 promoter and enhancer was utilized to construct a vector for driving expression of an anticoagulant, locally and specifically, in the endothelium of the resulting transgenic animals. In another embodiment of the current invention, the porcine ICAM-2 promoter, and portions of its first intron containing enhancer activity (also termed the "ICAM-2 enhancer" herein can be used. In one example, the porcine ICAM-2 promoter, and portions of its first intron containing enhancer activity (also termed the "ICAM-2 enhancer" herein) (Godwin et al., 2006. Xenotransplantation. November; 13 (6): 514-21) was utilized to construct a second vector for driving expression of an anticoagulant, locally and specifically, in the endothelium of the resulting transgenic animals.

In certain embodiments of the present invention, Tissue factor pathway inhibitor (TFPI) can be used as the anticoagulant, TFPI is a single-chain polypeptide which can reversibly inhibit Factor Xa (Xa) and Thrombin (Factor IIa) and thus inhibits TF dependent coagulation. For a review of TFPI, please see Crawley and Lane (Arterioscler Thromb Vasc Biol. 2008, 28 (2): 233-42). Dorling and colleagues generated transgenic mice expressing a fusion protein consisting of the three Kunitz domains of human TFPI linked to the transmembrane/cytoplasmic domains of human CD4, with a P-selectin tail for targeting to Weibel-Palade intracellular storage granules (Chen D, et al. Am J Transplant 2004; 4:1958-1963.). The resulting activation-dependent display of TFPI on the endothelium was sufficient to completely inhibit thrombosis-mediated acute humoral rejection of mouse cardiac xenografts by cyclosporine-treated rats. There was also a suggestion that effective regulation of coagulation may prevent chronic rejection. Similar results were obtained with transgenic mouse hearts expressing a hirudin/CD4/P-selectin fusion protein, indicating that inhibition of thrombin generation or activity was the key to protection in this model.

In certain embodiments, hirudin can be used as the anticoagulant of the present invention. Hirudin is a naturally occurring peptide in the salivary glands of medicinal leeches (such as Hirudo medicinalis) and is a potent inhibitor of thrombin. Dorling and coworkers (Chen et al., J Transplant. 2004 December; 4 (12): 1958-63) also generated transgenic mice expressing membrane-tethered hirudin fusion proteins, and transplanted their hearts into rats (mouse-rat Xeno-Tx). In contrast to control non-transgenic mouse hearts, which were all rejected within 3 days, 100% of the organs from both strains of transgenic mice were completely resistant to humoral rejection and survived for more than 100 days when T-cell-mediated rejection was inhibited by administration of ciclosporin A. Riesbeck et al., (Circulation. 1998 Dec. 15; 98 (24): 2744-52) also explored the expression of hirudin fusion proteins in mammalian cells as a strategy for prevention of intravascular thrombosis. Expression in cells reduced local thrombin levels and inhibited fibrin formation. Therefore, hirudin is another anticoagulant transgene of interest for preventing the thrombotic effects present in xenotransplantation.

In other certain embodiments, thrombomodulin can be used as the anticoagulant of the present invention. Thrombomodulin (TM) functions as a cofactor in the thrombin-induced activation of protein C in the anticoagulant pathway by forming a 1:1 stoichiometric complex with thrombin. Endothelial cell protein C receptor (EPCR) is an N-glyco-sylated type I membrane protein that enhances the activation of protein C. The role of these proteins in the protein C anticoagulant system is reviewed by Van de Wouwer et al., Arterioscler Thromb Vasc Biol. 2004 August; 24 (8): 1374-83. Expression of these and other anticoagulant transgenes has been explored by various groups to potentially address the coagulation barriers to xenotransplantation (reviewed by Cowan and D'Apice, Cur Opin Organ Transplant. 2008 April; 13 (2): 178-83). Esmon and coworkers (Li et al., J Thromb Haemost. 2005 July; 3 (7): 1351-9 over-expressed EPCR on the endothelium of transgenic mice and showed that such expression protected the mice from thrombotic challenge. Iino et al., (J Thromb Haemost. 2004 May; 2 (5): 833-4), suggested ex-vivo over expression of TM in donor islets via gene therapy as a means to prevent thrombotic complications in islet transplantation.

In certain embodiments, CD39 can be used as the anticoagulant of the present invention. CD39 is a major vascular nucleoside triphosphate diphosphohydrolase (NTPDase), and converts ATP, and ADP to AMP and ultimately adenosine. Extracellular adenosine plays an important role in thrombosis and inflammation, and thus has been studied for its beneficial role in transplantation (reviewed by Robson et al. Semin Thromb Hemost. 2005 April; 31 (2): 217-33). Recent studies have shown that CD39 has a major effect in reducing the inflammatory response (Beldi et al., Front Biosci, 2008, 13:2588-2603). Transgenic mice expressing hCD39 exhibited impaired platelet aggregation, prolonged bleeding times, and resistance to systemic thromboembolism in a heart transplant model (Dwyer et al., J Clin Invest. 2004 May; 113 (10): 1440-6). They were also shown to express CD39 on pancreatic islets and when incubated with human blood, these islets significantly delayed clotting time compared to wild type islets (Dwyer et al., Transplantation. 2006 Aug. 15; 82 (3): 428-32). Preliminary efforts at expressing hCD39 at high levels from a constitutive promoter system in transgenic pigs, showed high post-natal lethality (Revivicor, Inc., unpublished data). Thus there is a need to express anticoagulant transgenes in pigs in a manner that does not compromise the animal's well being, yet still provides adequate levels of expression for utility in clinical xenotransplantation.

Cytoprotective Transgenes

The present invention includes cytoprotective transgenes ("cytoprotectants'). Cytoprotective transgenes are considered to include anti-apoptotics, anti-oxidants and anti-inflammatories. Examples include:

(a) A20: In certain embodiments, A20 can be used as the cytoprotective transgene of the present invention. A20 provides anti-inflammatory and anti-apoptotic activity. Vascularized transplanted organs may be protected against endothelial cell activation and cellular damage by anti-inflammatory, anticoagulant and/or anti-apoptotic molecules. Among genes with great potential for modulation of acute vascular rejection (AVR) is the human A20 gene (hA20) that was first identified as a tumor necrosis factor (TNF)-$\alpha$ inducible factor in human umbilical vein endothelial cells. Human A20 has a double cytoprotective function by protecting endothelial cells from TNF-mediated apoptosis and inflammation, via blockade of several caspases, and the transcription factor nuclear factor-KB, respectively. Viable A20 transgenic piglets have been produced and in these animals expression of hA20 was restricted to skeletal muscle, heart and PAECs which were protected against TNF mediated apoptosis by hA20 expression and at least partly against CD95 (Fas) L-mediated cell death. In addition, cardiomyocytes from hA20-transgenic-cloned pigs were partially protected against cardiac insults (Oropeza et al., Xenotransplantation. 2009 November; 16 (6): 522-34).

(b) HO-1: In certain embodiments, HO can be used as the cytoprotective transgene of the present invention. HO provides anti-inflammatory, anti-apoptotic, and anti-oxidant activity. Heme oxygenases (HOs), rate-limiting enzymes in heme catabolism, also named HSP32, belong to members of heat shock proteins, wherein the heme ring is cleaved into ferrous iron, carbon monoxide (CO) and biliverdin that is then converted to bilirubin by biliverdin reductase. Three isoforms of HOS, including HO-1, HO-2 and HO-3, have been cloned. The expression of HO-1 is highly inducible, whereas HO-2 and HO-3 are constitutively expressed (Maines M D et al., Annual Review of Pharmacology & Toxicology 1997; 37:517-554, and Choi A M et al., American Journal of Respiratory Cell & Molecular Biology 1996; 15:9-19). An analysis of HO-1-/- mice suggests that the gene encoding HO-1 regulates iron homeostasis and acts as a cytoprotective gene having potent antioxidant, anti-inflammatory and anti-apoptotic effects (Poss K D et al., Proceedings of the National Academy of Sciences of the United States of America 1997; 94:10925-10930, Poss K D et al., Proceedings of the National Academy of Sciences of the United States of America 1997; 94:10919-10924, and Soares M P et al., Nature Medicine 1998; 4:1073-1077). Similar findings were recently described in a case report of HO-1 deficiency in humans (Yachie A et al., Journal of Clinical Investigation 1999; 103:129-135). The molecular mechanisms responsible for the cytoprotective effects of HO-1, including anti-inflammation, anti-oxidation and anti-apoptosis, are mediated by its' reaction products. HO-1 expression can be modulated in vitro and in vivo by protoporphyrins with different metals. Cobalt protoporphyrins (CoPP) and iron protoporphyrins (FePP) can up-regulate the expression of HO-1. In contrast, tin protoporphyrins (SnPP) and zinc protoporphyrins (ZnPP) inhibit the activity of HO-1 at the protein level. Recently, it has been proved that the expression of HO-1 suppresses the rejection of mouse-to-rat cardiac transplants (Sato K et al., J. Immunol. 2001; 166:4185-4194), protects islet cells from apoptosis, and improves the in vivo function of islet cells after transplantation (Pileggi A et al., Diabetes 2001; 50:1983-1991). It has also been proved that administration of HO-1 by gene transfer provides protection against hyperoxia-induced lung injury (Otterbein I. E et al., J Clin Invest 1999; 103:1047-1054), upregulation of HO-1 protects genetically fat Zucker rat livers from ischemia/reperfusion injury (Amersi F et al., J Clin Invest 1999; 104:1631-1639), and ablation or expression of HO-1 gene modulates cisplatin-induced renal tubular apoptosis (Shiraishi F et al., Am J Physiol Renal Physiol 2000; 278: F726-F736). In transgenic animal models, it was shown that over-expression of HO-1 prevents the pulmonary inflammatory and vascular responses to hypoxia (Minamino T et al., Proc. Natl. Acad. Sci. USA 2001; 98:8798-8803) and protects heart against ischemia and reperfusion injury (Yet S F, et al., Cir Res 2001; 89:168-173). Pigs carrying a HO-1 transgene have been produced however clinical effects related to their use in xenotransplantation were not reported (U.S. Pat. No. 7,378,569).

(c) FAT-1: In certain embodiments, FAT-1 can be used as the cytoprotective transgene of the present invention. FAT-1 provides anti-inflammatory activity. Polyunsaturated fatty acids (PUFAs) play a role in inhibiting (n-3 class) inflammation. Mammalian cells are devoid of desaturase that converts n-6 to n-3 PUFAs. Consequently, essential n-3 fatty acids must be supplied with the dict. Unlike mammals, however, the free-living nematode *Caenorhabditis elegans* expresses a n-3 fatty acid desaturase that introduces a double bond into n-6-fatty acids at the n-3 position of the hydrocarbon chains to form n-3 PUFAs. Transgenic mice have been generated that express the *C. elegans* fat-1 gene and, consequently, are able to efficiently convert dietary PUFAs of the 6 series to PUFAs of 3-series, such as EPA (20:5 n-3) and DHA (22-6 n-3). (Kang et al., Nature. 2004 Feb. 5; 427 (6974): 504). Another group produced a transgenic mouse model wherein the codons of fat-1 cDNA were further optimized for efficient translation in mammalian systems; endogenous production of n-3 PUFAs was achieved through overexpressing a *C. elegans* n-3 fatty acid desaturase gene, mfat-1. This group showed that cellular increase of n-3 PUFAs and reduction of n-6 PUFAs through transgenic expression of mfat-1 enhanced glucose-, amino acid-, and GLP-1-stimulated insulin secretion in isolated pancreatic islets of the mice, and rendered the islets strongly resistant to cytokine-induced cell death (Wei et al., Diabetes. 2010 February; 59 (2): 471-8).

(d) Soluble TNF-alpha receptor (sTNFR1): In certain embodiments, STNFR1 can be used as the cytoprotective transgene of the present invention. Tumor necrosis factor (TNF, cachexin or cachectin and formally known as tumor necrosis factor-alpha) is a cytokine involved in systemic inflammation and is a member of a group of cytokines that stimulate the acute phase reaction. The primary role of TNF is in the regulation of immune cells. TNF is able to induce apoptotic cell death, to induce inflammation. Soluble TNF-alpha receptor 1 (STNFR1) is an extracellular domain of TNFR1 and an antagonist to TNF-alpha (Su et al., 1998. Arthritis Rheum. 41, 139-149). Transgenic expression of sTNFR1 in xenografts may have beneficial anti-inflammatory effects.

In other certain embodiments, SOD can be used as the cytoprotective transgenes of the present invention. In other embodiments, catalase can be used as the cytoprotective transgenes of the present invention. Other cytoprotective with relevant anti-oxidant properties include, without limitation, SOD and catalase. Oxygen is the essential molecule for all aerobic organisms, and plays predominant role in ATP generation, namely, oxidative phosphorylation. During this process, reactive oxygen species (ROS) including superoxide anion $(O(2)(-))$ and hydrogen peroxide $(H(2)O(2))$ are produced as by-products. In man, an antioxidant defense system balances the generation of ROS. Superoxide dismutase (SOD) and catalase are two enzymes with anti-oxidant properties. SOD catalyses the dismutation of superoxide radicals to hydrogen peroxide, the latter being converted to water by catalase and glutathione peroxidase. Cellular damage resulting from generation of ROS can occur in a transplant setting. Therefore there is an interest in expressing anti-oxidant genes ex vivo or transgenically in donor tissues. Ex vivo gene transfer of EC-SOD and catalase were anti-inflammatory in a rat model of antigen induced arthritis (Dai et al., Gene Ther. 2003 April; 10 (7): 550-8). In addition, delivery of EC-SOD and/or catalase genes through the portal vein markedly attenuated hepatic I/R injury in a mouse model (He et al., Liver Transpl. 2006 December; 12 (12): 1869-79). Moreover, certain anticoagulants also provide anti-inflammatory activity including thrombomodulin, EPCR and CD39.

Production of Genetically Modified Animals

Genetically modified animals can be produced by any method known to one of skill in the art including, but not limited to, selective breeding, nuclear transfer, introduction of DNA into oocytes, sperm, zygotes, or blastomeres, or via the use of embryonic stem cells.

In some embodiments, genetic modifications may be identified in animals that are then bred together to form a herd of animals with a desired set of genetic modifications (or a single genetic modification). These progeny may be further bred to produce different or the same set of genetic modifications (or single genetic modification) in their progeny. This cycle of breeding for animals with desired genetic modification(s) may continue for as long as one desires. "Herd" in this context may comprise multiple generations of animals produced over time with the same or different genetic modification(s). "Herd" may also refer to a single generation of animals with the same or different genetic modification(s).

Cells useful for genetic modification (via, for example, but not limited to, homologous recombination) include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the cells used for producing the genetically modified animal (via, for example, but not limited to, nuclear transfer) can be obtained from different organs, e.g., skin, lung, pancreas, liver, stomach, intestine, heart, reproductive organs, bladder, kidney, urethra and other urinary organs, etc. Cells can be obtained from any cell or organ of the body, including all somatic or germ cells.

Additionally, animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, adult stem cells, mesenchymal stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B-cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts. In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Embryonic stem cells are a preferred germ cell type, an embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF).

Cells of particular interest include, among other lineages, stem cells, e.g. hematopoietic stem cells, embryonic stem cells, mesenchymal stem cells, etc., the islets of Langerhans, adrenal medulla cells which can secrete dopamine, osteoblasts, osteoclasts, epithelial cells, endothelial cells, leukocytes, e.g. B- and T-lymphocytes, myelomonocytic cells, etc., neurons, glial cells, ganglion cells, retinal cells, liver cells, e.g. hepatocytes, bone marrow cells, keratinocytes, hair follicle cells, and myoblast (muscle) cells.

In a particular embodiment, the cells can be fibroblasts or fibroblast-like cells having a morphology or a phenotype that is not distinguishable from fibroblasts, or a lifespan before senescence of at least 10 or at least 12 or at least 14 or at least 18 or at least 20 days, or a lifespan sufficient to allow homologous recombination and nuclear transfer of a non-senescent nucleus; in one specific embodiment, the cells can be fetal fibroblasts. Fibroblast cells are a suitable somatic cell type because they can be obtained from developing fetuses and adult animals in large quantities. These cells can be easily propagated in vitro with a rapid doubling time and can be clonally propagated for use in gene targeting procedures. The cells to be used can be from a fetal animal, or can be neonatal or from an adult animal in origin. The cells can be mature or immature and either differentiated or non-differentiated.

Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) Ann. Rev. Genet. 16:405; U.S. Pat. No. 4,888,274). The heteroduplex DNA can take several forms, including a three DNA strand containing triplex form wherein a single complementary strand invades the DNA duplex (Hsieh et al. (1990) Genes and Development 4:1951; Rao et al., (1991) PNAS 88:2984)) and, when two complementary DNA strands pair with a DNA duplex, a classical Holliday recombination joint or chi structure (Holliday, R. (1964) Genet. Res. 5:282) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, 3rd Ed. (1987) Lewin, B., John Wiley, New York, N.Y.; Lopez et al. (1987) Nucleic Acids Res. 15:5643). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules renders targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome). The present invention can us homologous recombination to inactivate a gene or insert and upregulate or activate a gene in cells, such as the cells described above. The DNA can comprise at least a portion of the gene(s) at the particular locus with introduction of an alteration into at least one, optionally both copies, of the native gene(s), so as to prevent expression of functional gene product. The alteration can be an insertion, deletion, replacement, mutation or combination thereof. When the alteration is introduced into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51:503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

Gene Knockdown/Knockout Via RNAi

An alternative technology for disrupting the expression of a gene is RNA interference. Interfering RNA (iRNA or siRNA) was originally described in the model organism *C. elegans* (Fire et al., Nature 391:806-811 (1998); U.S. Pat. No. 6,506,559 to Fire et al.). U.S. Pat. No. 6,573,099 and PCT Publication No. WO 99/49029 by Benitec Australia Ltd. claim isolated genetic constructs which are capable of delaying, repressing or otherwise reducing the expression of a target gene in an animal cell which is transfected with the genetic construct, wherein the genetic construct contains at least two copies of a structural gene sequence. The structural gene sequence is described as a nucleotide sequence which is substantially identical to at least a region of the target gene, and wherein at least two copies of the structural gene sequence are placed operably under the control of a single promoter sequence such that at least one copy of the structural gene sequence is placed operably in the sense orientation under the control of the promoter sequence. In the field of xenotransplantation, DNA constructs driving expression of siRNA's was used to knock down the expression of porcine endogenous retrovirous (PERV) in transgenic pigs, see for example Ramsoondar et al., Xenotransplantation. 2009 May-June; 16 (3): 164-80; Dieckhoff et al., Xenotransplantation. 2008 February; 15 (1): 36-45). siRNA technology has also been used to knock down alpha1,3 galactosyltransferase in porcine cells in vitro (Zhu et al., Transplantation. 2005 Feb. 15; 79 (3): 289-96).

Random Insertion

In one embodiment, the DNA encoding the transgene sequences can be randomly inserted into the chromosome of a cell. The random integration can result from any method of introducing DNA into the cell known to one of skill in the art. This may include, but is not limited to, electroporation, sonoporation, use of a gene gun, lipotransfection, calcium phosphate transfection, use of dendrimers, microinjection, the use of viral vectors including adenoviral, AAV, and retroviral vectors, and group II ribozymes. In one embodiment, the DNA encoding the can be designed to include a reporter gene so that the presence of the transgene or its expression product can be detected via the activation of the reporter gene. Any reporter gene known in the art can be used, such as those disclosed above. By selecting in cell culture those cells in which the reporter gene has been activated, cells can be selected that contain the transgene. In other embodiments, the DNA encoding the transgene can be introduced into a cell via electroporation. In other embodiments, the DNA can be introduced into a cell via lipofection, infection, or transformation. In one embodiment, the electroporation and/or lipofection can be used to transfect fibroblast cells. In a particular embodiment, the transfected fibroblast cells can be used as nuclear donors for nuclear transfer to generate transgenic animals as known in the art and described below.

Cells that have been stained for the presence of a reporter gene can then be sorted by FACS to enrich the cell population such that we have a higher percentage of cells that contain the DNA encoding the transgene of interest. In other embodiments, the FACS-sorted cells can then be cultured for a periods of time, such as 12, 24, 36, 48, 72, 96 or more hours or for such a time period to allow the DNA to integrate to yield a stable transfected cell population.

Vectors for Producing Transgenic Animals

Nucleic acid targeting vector constructs can be designed to accomplish homologous recombination in cells. In one embodiment, a targeting vector is designed using a "poly(A) trap". Unlike a promoter trap, a poly(A) trap vector captures a broader spectrum of genes including those not expressed in the target cell (i.e fibroblasts or ES cells). A polyA trap vector includes a constitutive promoter that drives expression of a selectable marker gene lacking a polyA signal. Replacing the polyA signal is a splice donor site designed to splice into downstream exons. In this strategy, the mRNA of the selectable marker gene can be stabilized upon trapping of a polyA signal of an endogenous gene regardless of its expression status in the target cells. In one embodiment, a targeting vector is constructed including a selectable marker that is deficient of signals for polyadenylation.

These targeting vectors can be introduced into mammalian cells by any suitable method including, but not limited, to transfection, transformation, virus-mediated transduction, or infection with a viral vector. In one embodiment, the targeting vectors can contain a 3' recombination arm and a 5' recombination arm (i.e. flanking sequence) that is homologous to the genomic sequence of interest. The 3' and 5' recombination arms can be designed such that they flank the 3' and 5' ends of at least one functional region of the genomic sequence. The targeting of a functional region can render it inactive, which results in the inability of the cell to produce functional protein. In another embodiment, the homologous DNA sequence can include one or more intron and/or exon sequences. In addition to the nucleic acid sequences, the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. The selectable marker can be located between the 5' and 3' recombination arm sequence.

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20:251-255, 2002; WO 00/51424.

A variety of enzymes can catalyze the insertion of foreign DNA into a host genome. Viral integrases, transposases and site-specific recombinases mediate the integration of virus genomes, transposons or bacteriophages into host genomes. An extensive collection of enzymes with these properties can be derived from a wide variety of sources. Retroviruses combine several useful features, including the relative simplicity of their genomes, case of use and their ability to integrate into the host cell genome, permitting long-term transgene expression in the transduced cells or their progeny. They have, therefore, been used in a large number of gene-therapy protocols. Vectors based on Lentivirus vectors, have been attractive candidates for both gene therapy and transgenic applications as have sdeno-associated virus, which is a small DNA virus (parvovirus) that is co-replicated in mammalian cells together with helper viruses such as adenovirus, herpes simplex virus or human cytomegalovirus. The viral genome essentially consists of only two ORFs (rep, a non-structural protein, and cap, a structural protein) from which (at least) seven different polypeptides are derived by alternative splicing and alternative promoter usage. In the presence of a helper-virus, the rep proteins mediate replication of the AAV genome. Integration, and thus a latent virus infection, occurs in the absence of helper virus. Transposons are also of interest. These are segments of mobile DNA that can be found in a variety of organisms. Although active transposons are found in many prokaryotic systems and insects, no functional natural transposons exist in vertebrates. The *Drosophila* P element transposon has been used for many years as a genome engineering tool. The sleeping beauty transposon was established from nonfunctional transposon copies found in salmonid fish and is significantly more active in mammalian cells than prokaryotic or insect transposons. Site-specific recombinases are enzymes that catalyze DNA strand exchange between DNA segments that possess only a limited degree of sequence homology. They bind to recognition sequences that are between 30 and 200 nucleotides in length, cleave the DNA backbone, exchange the two DNA double helices involved and relegate the DNA. In some site-specific recombination systems, a single polypeptide is sufficient to perform all of these reactions, whereas other recombinases require a varying number of accessory proteins to fulfill these tasks. Site-specific recombinases can be clustered into two protein families with distinct biochemical properties, namely tyrosine recombinases (in which the DNA is covalently attached to a tyrosine residue) and serine recombinases (where covalent attachment occurs at a serine residue). The most popular enzymes used for genome modification approaches are Cre (a tyrosine recombinase derived from *E. coli* bacteriophage P1) and fC31 integrase (a serine recombinase derived from the *Streptomyces* phage fC31). Several other bacteriophage derived site-specific recombinases (including Flp, lambda integrase, bacteriophage HK022 recombinase, bacteriophage R4 integrase and phage TP901-1 integrase) have been used successfully to mediate stable gene insertions into mammalian genomes. Recently, a site-specific recombinase has been purified from the *Streptomyces* bacteriophage. The fC31 recombinase is a member of the resolvase family and mediates phage integration. In this process the bacteriophage attP site recombines with the corresponding attB site in the bacterial genome. The crossover generates two sites, attL and attR, which are no longer a target for recombinase action, in the absence of accessory proteins. The reaction also takes place in mammalian cells and can therefore be used to mediate site-specific integration of therapeutic genes. The site-specificity of tyrosine-recombinases has been difficult to modify by direct protein engineering because the catalytic domain and the DNA recognition domain are closely interwoven. Therefore, changes in specificity are often accompanied by a loss in activity. Serine recombinases might be more amenable to engineering and a hyperactive derivative of Tn3 resolvase has been modified by exchange of the natural DBD for a zinc-finger domain of the human zinc-finger transcription factor Zif268. The DNA site-specificity of the resulting chimeric protein, termed Z-resolvase, had been switched to that of Zif268. Zinc-finger proteins can be modified by in vitro protein evolution to recognize any DNA sequence, therefore, this approach could enable development of chimeric recombinases that can integrate therapeutic genes into precise genomic locations. Methods for enhancing or mediating recombination include the combination of site-specific recombination and homologous recombination, AAV-vector mediated, and zinc-finger nuclease mediated recombination (ref: Geurts et. al., Science, 325:433, 2009)

The term "vector," as used herein, refers to a nucleic acid molecule (preferably DNA) that provides a useful biological or biochemical property to an inserted nucleic acid. "Expression vectors" according to the invention include vectors that are capable of enhancing the expression of one or more molecules that have been inserted or cloned into the vector, upon transformation of the vector into a cell. Examples of such expression vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids or virus-based vectors such as adenovirus, AAV, lentiviruses. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning® brand PCR cloning (Invitrogen Corp., Carlsbad, Calif.)) can also be applied to clone a nucleic acid into a vector to be used according to the present invention.

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3'recombination arm and a 5' recombination arm. Methods for the construction of targeting vectors have been described in the art, see, for example, Dai et al. (2002) Nature Biotechnology 20:251-255; WO 00/51424, FIG. 6; and *Gene Targeting: A Practical Approach*. Joyner, A. Oxford University Press, USA; $2^{nd}$ ed. Feb. 15, 2000.

Various constructs can be prepared for homologous recombination at a target locus. Usually, the construct can include at least 25 bp, 50 bp, 100 bp, 500 bp, 1 kbp, 2 kbp, 4 kbp, 5 kbp, 10 kbp, 15 kbp, 20 kbp, or 50 kbp of sequence homologous with the target locus.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). Sec Song et al. (1987) Proc. Nat'l Acad. Sci. U.S.A. 84:6820-6824. See also Sambrook et al. (1989) Molecular Cloning—A Laboratory Manual, Cold Spring Harbor Laboratory, Cold Spring Harbor, N.Y., see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, (1982) J. Mol. Appl. Genet. 1:327-341); and the hygromycin resistance gene (hyg) (Nucleic Acids Research 11:6895-6911 (1983), and Te Riele et al. (1990) Nature 348:649-651). Additional reporter genes useful in the methods of the present invention include acetohydroxyacid synthase (AHAS), alkaline phosphatase (AP), beta galactosidase (LacZ), beta glucoronidase (GUS), chloramphenicol acetyl-transferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, blasticidin, zeocin, methotrexate, phosphinothricin, puromycin, and tetracycline. Methods to determine suppression of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Combinations of selectable markers can also be used. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. Selectable markers can also be used for negative selection. Negative selection markets generally kill the cells in which they are expressed either because the expression is per se toxic or produces a catalyst that leads to toxic metabolite, such as Herpes simplex virus Type I thymidine kinase (HSV-tk) or diphtheria toxin A. Generally, the negative selection marker is incorporated into the targeting vector so that it is lost following a precise recombination event. Similarly, conventional selectable markers such as GFP can be used for negative selection using, for example, FACS sorting.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5-non-coding region (transcriptional regulatory region). Thus, the homologous region can extend beyond the coding region into the 5'-non-coding region or alternatively into the 3-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences or even a single nucleotide change such as a point mutation in an active site of an exon. Where mutation of a gene is desired, the marker gene can be inserted into an intron, so as to be excised from the target gene upon transcription.

Various considerations can be involved in determining the extent of homology of target DNA sequences, such as, for example, the size of the target locus, availability of sequences, relative efficiency of double cross-over events at the target locus and the similarity of the target sequence with other sequences. The targeting DNA can include a sequence in which DNA substantially isogenic flanks the desired sequence modifications with a corresponding target sequence in the genome to be modified. The substantially isogenic sequence can be at least about 95%, or at least about 97% or at least about 98% or at least about 99% or between 95 and 100%, 97-98%, 99.0-99.5%, 99.6-99.9%, or 100% identical to the corresponding target sequence (except for the desired sequence modifications). In a particular embodiment, the targeting DNA and the target DNA can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by E. coli, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA or RNA construct entry into the host cell include calcium phosphate/DNA coprecipitation, microinjection of DNA into the nucleus, electroporation, bacterial protoplast fusion with intact cells, transfection, lipofection, infection, particle bombardment, sperm mediated gene transfer, or any other technique known by one skilled in the art. The DNA or RNA can be single or double stranded, linear or circular, relaxed or supercoiled DNA. For various techniques for transfecting mammalian cells, see, for example, Keown et al., Methods in Enzymology Vol. 185, pp. 527-537 (1990).

The following vectors are provided by way of example. Bacterial: pBs, pQE-9 (Qiagen), phagescript, PsiX174, pBluescript SK, pBsKS, pNH8a, pNH16a, pNH18a, pNH46a (Stratagenc); pTrc99A, pKK223-3, pKK233-3, pDR540, pRIT5 (Pharmacia). Eukaryotic: pLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlucBacIII, pCDM8, pcDNA1, pZcoSV, pcDNA3 pREP4, pCEP4, and pEBVHis (Invitrogen, Corp.) and variants or derivatives thereof.

Other vectors include pUC18, pUC19, pBlueScript, pSPORT, cosmids, phagemids, YAC's (yeast artificial chromosomes), BAC's (bacterial artificial chromosomes), P1 (Escherichia coli phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSY- SPORT1 (Invitrogen) and variants or derivatives thereof. Viral vectors can also be used, such as lentiviral vectors (see, for example, WO 03/059923; Tiscornia et al. PNAS 100: 1844-1848 (2003)).

Additional vectors of interest include pTrxFus, pThioHis, pLEX, pTrcHis, pTrcHis2, pRSET, pBlueBacHis2, pcDNA3.1/His, pcDNA3.1 (−)/Myc-His, pSecTag, pEBVHis, pPIC9K, pPIC3.5K, pAO8IS, PPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErOl.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, PREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1λ T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue®, pT7Blue-2, pCITE-4abc(+), pOCUS-2, pTAg, pET-32L1C, pET-30LIC, pBAC-2cp LIC, pBACgus-2cp LIC, pT7Blue-2 LIC, pT7Blue-2, λ SCREEN-1, λ BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd (+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS+/−, pBluescript II SK+/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, POPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Promoters

Vector constructs used to produce the animals of the invention can include regulatory sequences, including, for example, a promoter, operably linked to the sequence. Large numbers of suitable vectors and promoters are known to those of skill in the art, and are commercially available.

In specific embodiments, the present invention provides animals, organs, tissues and cells that express a transgene, and in particular an immunomodulator or anticoagulant transgene, in endothelium. To target expression to a particular tissue, the animal is developed using a vector that includes a promoter specific for endothelial gene expression.

In one embodiment, the nucleic acid construct contains a regulatory sequence operably linked to the transgene sequence to be expressed. In one embodiment, the regulatory sequence can be a promoter sequence. In one embodiment, the promoter can be a regulatable promoter. In such systems, drugs, for example, can be used to regulate whether the peptide is expressed in the animal, tissue or organ. For example, expression can be prevented while the organ or tissue is part of the pig, but expression induced once the pig has been transplanted to the human for a period of time to overcome the cellular immune response. In addition, the level of expression can be controlled by a regulatable promoter system to ensure that immunosuppression of the recipient's immune system does not occur. The regulatable promoter system can be selected from, but not limited to, the following gene systems: a metallothionein promoter, inducible by metals such as copper (see Lichtlen and Schaffner, Swiss Med Wkly., 2001, 131 (45-46): 647-52); a tetracycline-regulated system (see Imhof et al., J Gene Med., 2000, 2 (2): 107-16); an ecdysone-regulated system (see Saez et al., Proc Natl Acad Sci USA., 2000, 97 (26): 14512-7); a cytochrome P450 inducible promoter, such as the CYP1A1 promoter (see Fujii-Kuriyama et al., FASEB J., 1992, 6 (2): 706-10); a mifepristone inducible system (see Sirin and Park, Gene., 2003, 323:67-77); a coumarin-activated system (see Zhao et al., Hum Gene Ther., 2003, 14 (17): 1619-29); a macrolide inducible system (responsive to macrolide antibiotics such as rapamycin, erythromycin, clarithromycin, and roxitiromycin) (see Weber et al., Nat Biotechnol., 2002, 20 (9): 901-7; Wang et al., Mol Ther., 2003, 7 (6): 790-800); an ethanol induced system (see Garoosi et al., J Exp Bot., 2005, 56 (416): 163542; Roberts et al., Plant Physiol., 2005, 138 (3): 1259-67); a streptogramin inducible system (see Fussenegger et al., Nat Biotechnol., 2000 18 (11): 1203-8) an electrophile inducible system (see Zhu and Fahl, Biochem Biophys Res Commun., 2001, 289 (1): 212-9); and a nicotine inducible system (see Malphettes et al., Nucleic Acids Res., 2005, 33 (12): e107).

In particular embodiments, the promoter is a tissue specific promoter such as those described herein. The tissue specific promoter can be used in particular for the expression of an anticoagulant or immunosuppressant. The tissue specific promoter is most preferably a endothelial-specific promoter. In one embodiment, the endothelial-specific promoter is the mouse Tie-2 promoter (see, for example, Schlaeger et al., 1997 Proc Natl Acad Sci USA. April 1; 94 (7): 3058-63). In another embodiment, the endothelial-specific promoter is the porcine ICAM-2 promoter (see, for example, Godwin et al., 2006. Xenotransplantation. November; 13 (6): 514-21). In other embodiments an enhancer element is used in the nucleic acid construct to facilitate increased expression of the transgene in a tissue-specific manner. Enhancers are outside elements that drastically alter the efficiency of gene transcription (Molecular Biology of the Gene, Fourth Edition, pp. 708-710, Benjamin Cummings Publishing Company, Menlo Park, CA © 987). In certain embodiments, the animal expresses a transgene under the control of a promoter in combination with an enhancer element. In particular embodiments, the animal includes an endothelial specific promoter element, such as a porcine ICAM-2 or murine Tie-2 promoter, and further includes an enhancer element. In some embodiments, the promoter is used in combination with an enhancer element which is a non-coding or intronic region of DNA intrinsically associated or co-localized with the promoter. In a specific embodiment, the enhancer element is Tie-2 used in combination with the Tie-2 promoter. In another specific embodiment, the enhancer element is ICAM-2 used in combination with the ICAM-2 promoter. In other embodiments, the promoter can be a ubiquitous promoter. Ubiquitous promoters include, but are not limited to the following: viral promoters like CMV, SV40. Suitable promoters also include beta-Actin promoter, gamma-actin promoter, GAPDH promoters, $H_2K$, ubiquitin and the rosa promoter.

Selection of Transgenic Cells

In some cases, the transgenic cells have genetic modifications that are the result of targeted transgene insertion or integration (i.e. via homologous recombination) into the cellular genome. In some cases, the transgenic cells have genetic modification that are the result of non-targeted (random) integration into the cellular genome. The cells can be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, (or, in non-targeted applications, where random integration techniques have produced the desired result) cells can be identified in which homologous recombination (or desired non-targeted integration events) has occurred to inactivate or otherwise modify the target gene.

The presence of the selectable marker gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. For example, by demonstrating the presence of the primer sequences or the expected size sequence, the occurrence of homologous recombination is supported.

The polymerase chain reaction used for screening homologous recombination events is described in Kim and Smithies, (1988) Nucleic Acids Res. 16:8887-8903; and Joyner et al. (1989) Nature 338:153-156.

The cell lines obtained from the first round of targeting (or from non-targeted (random) integration into a desired location) are likely to be heterozygous for the integrated allele. Homozygosity, in which both alleles are modified, can be achieved in a number of ways. One approach is to grow up a number of cells in which one copy has been modified and then to subject these cells to another round of targeting (or non-targeted (random) integration) using a different selectable marker. Alternatively, homozygotes can be obtained by breeding animals heterozygous for the modified allele. In some situations, it can be desirable to have two different modified alleles. This can be achieved by successive rounds of gene targeting (or random integration) or by breeding heterozygotes, each of which carries one of the desired modified alleles. In certain embodiments, at least one element of the animal is derived by selection of a spontaneously occurring mutation in an allele, in particular to develop a homozygous animal. In certain embodiments, a selection technique is used to obtain homologous knockout cells from heterozygous cells by exposure to very high levels of a selection agent. Such a selection can be, for example, by use of an antibiotic such as geneticin (G418).

Cells that have been transfected or otherwise received an appropriate vector can then be selected or identified via genotype or phenotype analysis. In one embodiment, cells are transfected, grown in appropriately-selected medium to identify cells containing the integrated vector. The presence of the selectable marker gene indicates the presence of the transgene construct in the transfected cells. Those cells which show the desired phenotype can then be further analyzed by restriction analysis, electrophoresis, Southern analysis, polymerase chain reaction, etc to analyze the DNA in order to verify integration of transgene(s) into the genome of the host cells. Primers can also be used which are complementary to transgene sequence(s). The polymerase chain reaction used for screening homologous recombination and random integration events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

Cells that have undergone homologous recombination can be identified by a number of methods. In one embodiment, the selection method can detect the absence of an immune response against the cell, for example by a human anti-gal antibody. In other embodiments, the selection method can include assessing the level of clotting in human blood when exposed to a cell or tissue. Selection via antibiotic resistance has been used most commonly for screening. This method can detect the presence of the resistance gene on the targeting vector, but does not directly indicate whether integration was a targeted recombination event or a random integration. Alternatively, the marker can be a fluorescent marker gene such as GFP or RFP, or a gene that is detectable on the cell surface via cell sorting or FACs analysis. Certain technology, such as Poly A and promoter trap technology, increase the probability of targeted events, but again, do not give direct evidence that the desired phenotype has been achieved. In addition, negative forms of selection can be used to select for targeted integration; in these cases, the gene for a factor lethal to the cells (e.g. Tk or diptheria A toxin) is inserted in such a way that only targeted events allow the cell to avoid death. Cells selected by these methods can then be assayed for gene disruption, vector integration and, finally, gene depletion. In these cases, since the selection is based on detection of targeting vector integration and not at the altered phenotype, only targeted knockouts, not point mutations, gene rearrangements or truncations or other such modifications can be detected.

Characterization can be further accomplished by the following techniques, including, but not limited to: PCR analysis, Southern blot analysis, Northern blot analysis, specific lectin binding assays, and/or sequencing analysis. Phenotypic characterization can also be accomplished, including by binding of anti-mouse antibodies in various assays including immunofluroescence, immunocytochemistry, ELISA assays, flow cytometry, western blotting, testing for transcription of RNA in cells such as by RT-PCR.

In other embodiments, GTKO animals or cells contain additional genetic modifications. Genetic modifications can include more than just homologous targeting, but can also include random integrations of exogenous genes, mutations, deletions and insertions of genes of any kind. The additional genetic modifications can be made by further genetically modifying cells obtained from the transgenic cells and animals described herein or by breeding the animals described herein with animals that have been further genetically modified. Such animals can be modified to eliminate the expression of at least one allele of αGT gene, the CMP-Neu5Ac hydroxylase gene (see, for example, U.S. Pat. No. 7,368,284), the iGb3 synthase gene (see, for example, U.S. Patent Publication No. 2005/0155095), and/or the Forssman synthase gene (see, for example, U.S. Patent Publication No. 2006/0068479). In additional embodiments, the animals described herein can also contain genetic modifications to express fucosyltransferase, sialyltransferase and/or any member of the family of glucosyltransferases. To achieve these additional genetic modifications, in one embodiment, cells can be modified to contain multiple genetic modifications. In other embodiments, animals can be bred together to achieve multiple genetic modifications. In one specific embodiment, animals, such as pigs, lacking expression of functional immunoglobulin, produced according to the process, sequences and/or constructs described herein, can be bred with animals, such as pigs, lacking expression of αGT (for example, as described in WO 04/028243).

In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene.

In addition, genes or cDNA encoding complement related proteins, which are responsible for the suppression of complement mediated lysis can also be expressed in the animals and tissues of the present invention. Such genes include, but are not limited to CD59, DAF (CD55), and CD46 (see, for example, WO 99/53042; Chen et al. Xenotransplantation, Volume 6 Issue 3 Page 194-August 1999, which describes pigs that express CD59/DAF transgenes; Costa C et al, *Xenotransplantation.* 2002 January; 9 (1): 45-57, which describes transgenic pigs that express human CD59 and H-transferase; Zhao L et al.; Diamond L E et al. *Transplantation.* 2001 Jan. 15; 71 (1): 132-42, which describes a human CD46 transgenic pigs.)

Additional modifications can include expression of compounds, such as antibodies, which down-regulate the expression of a cell adhesion molecule by the cells, such as described in WO 00/31126, entitled "Suppression of xenograft rejection by down regulation of a cell adhesion molecules" and compounds in which costimulation by signal 2 is prevented, such as by administration to the organ recipient of a soluble form of CTLA-4 from the xenogeneic donor organism, for example as described in WO 99/57266, entitled "Immunosuppression by blocking T cell costimulation signal 2 (B7/CD28 interaction)".

Nuclear Transfer

Engineered transgenic animals such as ungulates or pigs described herein may be produced using any suitable techniques known in the art. These techniques include, but are not limited to, microinjection (e.g., of pronuclei), sperm-mediated gene transfer, electroporation of ova or zygotes, and/or nuclear transplantation.

In certain embodiments, sperm mediated gene transfer can be used to produce the genetically modified ungulates described herein. The methods and compositions described herein to insert transgenes can be used to genetically modify sperm cells via any technique described herein or known in the art. The genetically modified sperm can then be used to impregnate a female recipient via artificial insemination, intracytoplasmic sperm injection or any other known technique. In one embodiment, the sperm and/or sperm head can be incubated with the exogenous nucleic acid for a sufficient time period. Sufficient time periods include, for example, about 30 seconds to about 5 minutes, typically about 45 seconds to about 3 minutes, more typically about 1 minute to about 2 minutes.

The potential use of sperm cells as vectors for gene transfer was first suggested by Brackeff et al., Proc., Natl. Acad. Sci. USA 68:353-357 (1971). This was followed by reports of the production of transgenic mice and pigs after in vitro fertilization of oocytes with sperm that had been incubated by naked DNA (see, for example, Lavitrano et al., Cell 57:717-723 (1989) and Gandolfi et al. Journal of Reproduction and Fertility Abstract Series 4, 10 (1989)), although other laboratories were not able to repeat these experiments (see, for example, Brinster et al. Cell 59:239-241 (1989) and Gavora et al., Canadian Journal of Animal Science 71:287-291 (1991)). Since then, successful sperm mediated gene transfer has been achieved in chicken (see, for example, Nakanishi and Iritani, Mol. Reprod. Dev. 36:258-261 (1993)); mice (see, for example, Maione, Mol. Reprod. Dev. 59:406 (1998)); and pigs (see, for example, Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; issued Apr. 23, 2002; U.S. Patent Publication Nos. 20010044937, published Nov. 22, 2001, and 20020108132, published Aug. 8, 2002).

In some embodiments, intracytoplasmic sperm injection can be used to produce the genetically modified ungulates described herein. This can be accomplished by coinserting an exogenous nucleic acid and a sperm into the cytoplasm of an unfertilized oocyte to form a transgenic fertilized oocyte, and allowing the transgenic fertilized oocyte to develop into a transgenic embryo and, if desired, into a live offspring. The sperm can be a membrane-disrupted sperm head or a demembranated sperm head. The coinsertion step can include the substep of preincubating the sperm with the exogenous nucleic acid for a sufficient time period, for example, about 30 seconds to about 5 minutes, typically about 45 seconds to about 3 minutes, more typically about 1 minute to about 2 minutes. The coinsertion of the sperm and exogenous nucleic acid into the oocyte can be via microinjection. The exogenous nucleic acid mixed with the sperm can contain more than one transgene, to produce an embryo that is transgenic for more than one transgene as described herein. The intracytoplasmic sperm injection can be accomplished by any technique known in the art, see, for example, U.S. Pat. No. 6,376,743.

Any additional technique known in the art may be used to introduce the transgene into animals. Such techniques include, but are not limited to pronuclear microinjection (see, for example, Hoppe, P. C. and Wagner, T. E., 1989, U.S. Pat. No. 4,873,191); retrovirus mediated gene transfer into germ lines (see, for example, Van der Putten et al., 1985, Proc. Natl. Acad. Sci., USA 82:6148-6152); gene targeting in embryonic stem cells (see, for example, Thompson et al., 1989, Cell 56:313-321; Wheeler, M. B., 1994, WO) 94/26884); electroporation of embryos (see, for example, Lo, 1983, Mol Cell. Biol. 3:1803-1814); cell gun; transfection; transduction; retroviral infection; adenoviral infection; adenoviral-associated infection; liposome-mediated gene transfer; naked DNA transfer; and sperm-mediated gene transfer (see, for example, Lavitrano et al., 1989, Cell 57:717-723); etc. For a review of such techniques, see, for example, Gordon, 1989, Transgenic Anithals, Intl. Rev. Cytol. 115:171-229. In particular embodiments, the expression of CTLA4 and/or CTLA4-Ig fusion genes in ungulates can be accomplished via these techniques.

In one embodiment, microinjection of the constructs encoding the transgene can be used to produce the transgenic animals. In one embodiment, the nucleic acid construct or vector can be microinjection into the pronuclei of a zygote. In one embodiment, the construct or vector can be injected into the male pronuclei of a zygote. In another embodiment, the construct or vector can be injected into the female pronuclei of a zygote. In a further embodiment, the construct or vector can be injected via sperm-mediated gene transfer.

Microinjection of the transgene construct or vector can include the following steps: superovulation of a donor female; surgical removal of the egg, fertilization of the egg; injection of the transgene transcription unit into the pronuclei of the embryo; and introduction of the transgenic embryo into the reproductive tract of a pseudopregnant host mother, usually of the same species. See for example U.S. Pat. No. 4,873,191, Brinster, et al. 1985. PNAS 82:4438; Hogan, et al., in "Manipulating the Mouse Embryo: A Laboratory Manual". Cold Spring Harbor Laboratory, Cold Spring Harbor, N.Y., 1986. Robertson, 1987, in Robertson, ed. "Teratocarcinomas and Embryonic Stem Cells a Practical Approach" IRL Press, Evnsham. Oxford, England. Pedersen, et al., 1990. "Transgenic Techniques in Mice—A Video Guide", Cold Spring Harbor Laboratory, Cold Spring Harbor, N.Y. Transgenic pigs are routinely produced by the microinjection of a transgene construct or vector into pig embryos. In one embodiment, the presence of the transgene can be detected by isolating genomic DNA from tissue from the tail of each piglet and subjecting about 5 micrograms of this genomic DNA to nucleic acid hybridization analysis with a transgene specific probe. In a particular embodiment, transgenic animals can be produced according to any method known to one skilled in the art, for example, as disclosed in Bleck et al., J. Anim. Sci., 76:3072 [1998]; also described in U.S. Pat. Nos. 6,872,868; 6,066,725; 5,523, 226; 5,453,457; 4,873,191; 4,736,866; and/or PCT Publication No. WO/9907829.

In one embodiment, the pronuclear microinjection method can include linking at least approximately 50, 100, 200, 300, 400 or 500 copies of the transgene-containing construct or vector of the present invention to a promoter of choice, for example, as disclosed herein, and then the foreign DNA can be injected through a fine glass needle into fertilized eggs. In one embodiment, the DNA can be injected into the male pronucleus of the zygote. Pig zygotes are opaque and visualization of nuclear structures can be difficult. In one embodiment, the pronuclei or nuclei of pig zygotes can be visualized after centrifugation, for example, at 15000 g for 3 mm. The injection of the pronucleus can be carried out under magnification and use of standard micro-injection apparatus. The zygote can be held by a blunt holding pipette and the zona pellucida, plasma membrane and pronuclear envelope can be penetrated by an injection pipette. The blunt holding pipette can have a small diameter, for example, approximately 50 um. The injection pipette can have a smaller diameter than the holding pipette, for example, approximately 15 um. DNA integration occurs during replication as a repair function of the host DNA. These eggs, containing the foreign DNA, can then be implanted into surrogate mothers for gestation of the embryo according to any technique known to one skilled in the art.

In some embodiments, pronuclear microinjection can be performed on the zygote 12 hours post fertilization. Uptake of such genes can be delayed for several cell cycles. The consequence of this is that depending on the cell cycle of uptake, only some cell lineages may carry the transgene, resulting in mosaic offspring. If desired, mosaic animals can be bred to form true germline transgenic animals.

In other embodiments, ungulate cells such as porcine cells containing transgenes can be used as donor cells to provide the nucleus for nuclear transfer into enucleated oocytes to produce cloned, transgenic animals. In one embodiment, the ungulate cell need not express the transgene protein in order to be useful as a donor cell for nuclear transfer. In one embodiment, the porcine cell can be engineered to express a transgene from a nucleic acid construct or vector that contains a promoter. Alternatively, the porcine cells can be engineered to express transgene under control of an endog-enous promoter through homologous recombination. In one embodiment, the transgene nucleic acid sequence can be inserted into the genome under the control of a tissue specific promoter, tissue specific enhancer or both. In another embodiment, the transgene nucleic acid sequence can be inserted into the genome under the control of a ubiquitous promoter. In certain embodiments, targeting vec-tors are provided, which are designed to allow targeted homologous recombination in somatic cells. These targeting vectors can be transformed into mammalian cells to target the endogenous genes of interest via homologous recombi-nation. In one embodiment, the targeting construct inserts both the transgene nucleotide sequence and a selectable maker gene into the endogenous gene so as to be in reading frame with the upstream sequence and produce an active fusion protein. Cells can be transformed with the constructs using the methods of the invention and are selected by means of the selectable marker and then screened for the presence of recombinants.

The present invention provides a method for cloning an ungulate such as a pig containing certain transgenes via somatic cell nuclear transfer. In general, the pig can be produced by a nuclear transfer process comprising the following steps: obtaining desired differentiated pig cells to be used as a source of donor nuclei; obtaining oocytes from a pig; enucleating said oocytes; transferring the desired differentiated cell or cell nucleus into the enucleated oocyte, e.g., by fusion or injection, to form nuclear transfer (NT) units; activating the resultant NT unit; and transferring said cultured NT unit to a host pig such that the NT unit develops into a fetus.

Nuclear transfer techniques or nuclear transplantation techniques are known in the art (see, for example, Dai et al. Nature Biotechnology 20:251-255; Polejacva et al Nature 407:86-90 (2000); Campbell, et al., *Theriogenology* 68 Suppl 1: S214-3 1 (2007); Vajta, et al., *Reprod Fertil Dev* 19 (2): 403-23 (2007); Campbell et al. (1995) Theriogenology, 43:181; Collas et al. (1994) Mol. Report Dev., 38:264-267; Keefer et al. (1994) Biol. Reprod., 50:935-939; Sims et al. (1993) Proc. Natl. Acad. Sci., USA, 90:6143-6147; WO 94/26884; WO 94/24274, and WO 90/03432, U.S. Pat. Nos. 4,944,384, 5,057,420, WO 97/07669, WO 97/07668, WO 98/30683, WO 00/22098, WO 004217, WO 00/51424, WO 03/055302, WO 03/005810, U.S. Pat. Nos. 6,147,276, 6,215,041, 6,235,969, 6,252,133, 6,258,998, 5,945,577, 6,525,243, 6,548,741, and Phelps et al. (Science 299:411-414 (2003)).

A donor cell nucleus, which has been modified to contain a transgene of the present invention, is transferred to a recipient porcine oocyte. The use of this method is not restricted to a particular donor cell type. The donor cell can be as described in Wilmut et al. (1997) Nature 385:810; Campbell et al. (1996) Nature 380:64-66; or Cibelli et al. (1998) Science 280:1256-1258. All cells of normal karyo-type, including embryonic, fetal and adult somatic cells which can be used successfully in nuclear transfer can in principle be employed. Fetal fibroblasts are a particularly useful class of donor cells. Generally suitable methods of nuclear transfer are described in Campbell et al. (1995) Theriogenology 43:181, Collas et al. (1994) Mol. Reprod. Dev. 38:264-267, Keefer et al. (1994) Biol. Reprod. 50:935-939, Sims et al. (1993) Proc. Nat'l. Acad. Sci. USA 90:6143-6147, WO-A-9426884, WO-A-9424274, WO-A-9807841, WO-A-9003432, U.S. Pat. Nos. 4,994,384 and 5,057,420, Campbell et al., (2007) Theriogenology 68 Suppl 1, S214-231, Vatja et al., (2007) Reprod Fertil Dev 19, 403-423). Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (see, for example, Campbell et al. (1996) Nature, 380:64-68) and Stice et al. (1996) Biol. Reprod., 20 54:100-110). In a particular embodiment, fibroblast cells, such as porcine fibroblast cells can be genetically modified to con-tain the transgene of interest.

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration and in the case of porcine generally occurs at about 35-55 hours. This period of time is known as the maturation period."

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-super-ovulated or superovulated porcine 35 to 48, or 39-41, hours past the onset of estrus or past the injection of human chorionic gonadotropin (hCG) or similar hormone.

After a fixed time maturation period, the oocytes can be enucleated. Prior to enucleation the oocytes can be removed and placed in appropriate medium, such as HECM or TCM199 containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7-10 micrograms per milliliter cytochalasin B, for immediate enucleation, or can be placed in a suitable medium, for example an embryo culture medium such as CR1aa, plus 10% estrus cow serum, and then enucleated later, for example not more than 24 hours later or 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 3-10 microgram per milliliter 33342 Hoechst dye in suitable holding medium, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. Sec, for example, U.S. Pat. No. 4,997,384 by Prather et al. A variety of electrofusion media can be used including, for example, sucrose, mannitol, sorbitol and phosphate buffered solution. For example, the fusion media can comprise a 280 milli molar (mM) solution of mannitol, containing 0.05 mM $MgCl_2$ and 0.001 mM $CaCl_2$) (Walker et al., Cloning and Stem Cells. 2002; 4 (2): 105-12). Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, (1994) Mol. Reprod. Dev., 38:264-267. After fusion, the resultant fused NT units are then placed in a suitable medium until activation, for example, CR1aa medium. Typically activation can be effected shortly thereafter, for example less than 24 hours later, or about 4-9 hours later for bovine NT and 1-4 hours later for porcine NT.

The NT unit can be activated by known methods. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prelusion oocytes to yield greater numbers of viable pregnancies and multiple genetically identical calves after nuclear transfer. Also, treatments such as electrical and chemical shock can be used to activate NT embryos after fusion. Sec, for example, U.S. Pat. No. 5,496,720 to Susko-Parrish et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured until they reach a suitable size for transferring to a recipient female, or alternately, they may be immediately transferred to a recipient female. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's Whitten's media, PZM, NCSU23 and NCSU37. See Yoshioka K, Suzuki C, Tanaka A, Anas I M, Iwamura S. Biol Reprod. (2002) January; 66 (1): 112-9 and Petters R M, Wells K D. J Reprod Fertil Suppl. 1993; 48:61-73.

Afterward, the cultured NT unit or units can be washed and then placed in a suitable media contained in well plates which can optionally contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. NT units can be cultured until at least about 2 to 400 cells, about 4 to 128 cells, or at least about 50 cells. Alternatively, NT units may be immediately transferred to a recipient female.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. Sec, for example, Siedel, G. E., Jr. (1981) "Critical review of embryo transfer procedures with cattle in Fertilization and Embryonic Development in Vitro, L. Mastroianni, Jr. and J. D. Biggers, ed., Plenum Press, New York, N.Y., page 323. Porcine embryo transfer can be conducted according to methods known in the art. For reference, see Youngs et al. "Factors Influencing the Success of Embryo Transfer in the Pig," Theriogenology (2002) 56:1311-1320.

Production of Multi-Transgenic Animals Containing Endothelial Specific (Endo) Transgenes Animals (or fetuses) of the invention can be produced according to the following means, including, but not limited to the group selected from: nuclear transfer (NT), natural breeding, rederivation via NT using cells from an existing cell line, fetus, or animal as nuclear donors-optionally adding additional transgenes to these cells prior to NT, sequential nuclear transfer, artificial reproductive technologies (ART) or any combination of these methods or other methods known in the art. In general, "breeding" or "bred" refers to any means of reproduction, including both natural and artificial means. Further, the present invention provides for all progeny of animals produced by the methods disclosed herein. It is understood that in certain embodiments such progeny can become homozygous for the genes described herein.

In one embodiment, cells are isolated from animals which lack expression of GT (GTKO) and are transgenic for CD46 (GTKO/CD46). These cells are further modified with an endothelial specific TM transgene, and the resulting transgenic cells are used as nuclear donors to generate GTKO/CD46/TM transgenic animals via NT.

In another embodiment, GTKO/CD46 cells are further modified with an endothelial specific CD39 transgene, and the resulting transgenic cells are used as nuclear donors to generate GTKO/CD46/CD39 transgenic animals via NT.

In a further embodiment, GTKO/CD46 cells are further modified with an endothelial specific EPCR transgene, and resulting transgenic cells are used as nuclear donors to generate GTKO/CD46/EPCR transgenic animals via NT.

In a further embodiment, GTKO/CD46 cells are further modified with endothelial specific TM and EPCR transgenes, and resulting transgenic cells are used as nuclear donors to generate GTKO/CD46/TM/EPCR transgenic animals via NT.

In another embodiment, GTKO/CD46/TM animals are mated with GTKO/CD46/CD39 animals to generate GTKO/CD46/TM/CD39 animals via breeding.

In one embodiment, cells are isolated from animals which lack expression of GT (GTKO) and are also transgenic for CD46 and DAF (constitutive expression). These GTKO/CD46/DAF transgenic cells are further modified with one or more endothelial specific transgenes (ESTR), such ESTR include but are not limited to the anticoagulant, immunosuppressant and/or cytoprotective transgenes described herein, and the resulting transgenic cells are used as nuclear donors to generate GTKO/CD46/DAF/ESTR transgenic animals via NT.

In another embodiment, cells are isolated from animals which lack expression of GT (GTKO) and are also transgenic for CD46 and CIITA (constitutive expression). These GTKO/CD46/CIITA transgenic cells are further modified with one or more endothelial specific transgenes (ESTR), such ESTR include but are not limited to the anticoagulant, immunosuppressant and/or cytoprotective transgenes described herein, and the resulting transgenic cells are used as nuclear donors to generate GTKO/CD46/CIITA/ESTR transgenic animals via NT.

In a further embodiment, cells are isolated from animals which lack expression of GT (GTKO) and are transgenic for CD46, DAF and CIITA (constitutive expression). These GTKO/CD46/DAF/CIITA cells are further modified with one or more endothelial specific transgenes (ESTR), such ESTR include but are not limited to the anticoagulant, immunosuppressant and/or cytoprotective transgenes described herein, and resulting transgenic cells are used as nuclear donors in NT to generate GTKO/CD46/DAF/CIITA ESTR transgenic animals.

In a further embodiment, GTKO/CD46/DAF/CIITA animals are bred to GTKO/CD46/endo transgenic animals to generate GTKO/CD46/DAF/CIITA ESTR transgenic animals.

In a further embodiment, GTKO/CD46/TM animals are bred to GTKO/CD46/DAF/CIITA transgenic animals to generate GTKO/CD46/TM/DAF/CIITA animals.

In a further embodiment, GTKO/CD46 animals which additionally contain an endothelial specific transgene are bred to GTKO/CD46/DAF/CIITA transgenic animals to generate GTKO/CD46/DAF/CHITA/ESTR transgenic animals via breeding.

In another embodiment, cells isolated from GTKO/CD46/TM animals are further modified with an immunosuppressant transgene, such as pCTLA4Ig. The resulting transgenic cells are used as nuclear donors to generate GTKO/CD46/TM/CTLA4Ig animals via NT.

In certain embodiments cells isolated from GTKO/CD46/TM animals are further modified with one or more immunomodulatory or anticoagulant transgenes, and the resulting cells containing four or more transgenes are used as nuclear donors to generate multi-transgenic animals via NT.

In further embodiments, any of the multitransgenic animals embodied herein can be bred together naturally, or using artificial reproductive technologies to generate multitransgenic animals with additional genetic modifications via breeding.

In addition, cells isolated from any of the multitransgenic animals (or fetuses) embodied herein can be used in further NT to rederive animals, or to add further genetic modifications to their genome followed by NT to generate multitransgenic animals containing additional genetic modifications via NT.

Whole Organ Xenografts

There is a critical shortage of human organs for the purposes of organ transplantation. In the United States alone approximately 110,000 patients are on waiting lists to receive organs, and yet only 30,000 organs will become available from deceased donors. Almost 20 patients die each day (7000 per year) waiting for an organ (Cooper and Ayares, 2010 International Journal of Surgery, In Press, doi: 10.1016/j.ijsu.2010.11.002). The supply of human organs for use in allotransplantation will never fully meet the population's need. A new source of donor organs is urgently needed.

Xenotransplantation could effectively address the shortage of human donor organs. Xenotransplants are also advantageously (i) supplied on a predictable, non-emergency basis; (ii) produced in a controlled environment; and (iii) available for characterization and study prior to transplant.

Depending on the relationship between donor and recipient species, the xenotransplant can be described as concordant or discordant. Concordant species are phylogenetically closely related species (e.g., mouse to rat). Discordant species are not closely related (e.g., pig to human). Pigs have been the focus of most research in the xenotransplanation area, since the pig shares many anatomical and physiological characteristics with human. Pigs also have relatively short gestation periods, can be bred in pathogen-free environments and may not present the same ethical issues associated with animals not commonly used as food sources (e.g., primates). The transplantation of whole porcine organs into non-human primates has been reviewed (see for example Ekser et al., Transplant Immun. 2009 21:87-92;

Ekser and Cooper. Expert Rev Clin Immunol. 2010 March; 6 (2): 219-30; Mohiuddin, M. PLOS Med. 2007 Mar. 27; 4 (3): e75; Pierson et al., Xenotransplantation. 2009 September-October; 16(5): 263-80). For therapeutic use of porcine organs to become available for use in human medical treatment, improved outcomes must first be obtained in non-human primate pre-clinical trials, followed by duplication or improvement of these results in human clinical trials. The pigs of the current invention can provide a source of porcine donor organs to address these requirements.

In additional embodiments, organs according to the present invention can be selected from the following: heart, lung, liver, kidney, intestine, spleen, and pancreas. In one embodiment, the xenotransplanted organs of the present invention can survive and function in the recipient like an allograft. In other embodiments, the organs described herein can be used as bridge organs until a human organ becomes available. In one embodiment, the bridge organ can be used in a recipient for at least 3 days. In other embodiments, the bridge organ can be used in a recipient a period of time selected from the following: at least 4, 5, 6, 7, 8, 9, 10, 14, 21, 28 days.

Hearts

In one embodiment, hearts obtained from animals of the current invention can be used pre-clinically and clinically to improve outcomes in cardiac xenotransplantation. Heart transplants can be heterotopic (non-life-supporting: the endogenous organ remains in place) or orthotopic (life-supporting, where the heart is replaced with a donor heart). In one embodiment, the heart transplants can be heterotrophic. In another embodiment, the heart transplants can be orthotropic. In non-human primate xenotransplant studies, the majority to date has been heterotopic grafts, but in later studies and in human clinical use, hearts will be transplanted orthotopically.

In one embodiment, hearts from pigs of the invention, when transplanted into a primate, can function for at least six months in a majority of primates. The majority of primates can be at least 70%, at least 75%, at least 80% or at least 90% of primtated. In other embodiments, the transplanted hearts of the present invention can function for a time period of at least 8 months, at least 9 months, at least 10 months, at least 11 months, at least 12 months, at least 15 months, at least 18 months, at least 21 month, at least 24 months, at least 36 months, or at least 48 months. Such transplants can be heterotopic or orthotopic.

In one embodiment, hearts from the pigs of the invention, when orthotopically transplanted in to a human can function for up to 9 months.

Using GTKO pigs and novel immunosuppressant agents, 2 to 6 months' survival of heterotopic heart xenotransplants was achieved (Kuwaki et al. Nat Med 2005:11:29-31; Tseng et al, Transplantation 2005:80:1493-500). Transgenic pigs with the combination of GTKO and expression of CD46 were recently tested in a heterotopic heart model (pig-to-baboon) and provided prolonged survival and function of xenograft hearts for up to 8 months. (Mohiuddin et al., Abstract TTS-1383. Transplantation 2010; 90 (suppl): 325).

In non-human primate heart xenotransplant studies, graft failure has occurred due to the development of a thrombotic microangiopathy that results in vascular occlusion and surrounding ischemic injury. Hearts from the pigs of the current invention, which express anticoagulant transgenes in the vascular endothelium will lesson or prevent thrombotic events, such as, for example, consumptive coagulopathy and thrombotic microangiopathy, from occurring and serve to protect the xenograft from injury. In one embodiment, hearts from the pigs disclosed herein can decrease thrombotic events. In another embodiment, hearts from the pigs disclosed herein can prevent thrombotic events. For reviews of progress in this heart xenotransplantation field over the past 20 years please see for example, Zhu et al, J Heart Lung Transplant. 2007 March; 26 (3): 210-8 and Ekser and Cooper, Curr Opin Organ Transplant. 2008 October; 13 (5): 531-5. The use of porcine donor hearts as a bridge transplant has also been detailed (Cooper and Teuteberg J Heart Lung Transplant. 2010 August; 29 (8): 838-40).

Additional embodiments encompass, pigs of the current invention containing further genetic modifications, for example, immunosuppressant transgenes, for example, endothelial expression of immunosuppressant transgenes, such as CTLA4-Ig, allows for the use of a clinically relevant immunosuppressant regimen to be used in cardiac xenotransplantation.

In other embodiments, the porcine heart can be transferred to a primate and can function in the primate for at least 6 months. In another embodiment, the porcine heart can be transferred to a primate and can function in the primate for at least 9 months. In a further embodiment, the porcine heart can be transferred to a primate and can function in the primate for at least 12 months. In a still further embodiment, the porcine heart can be transferred to a primate and can function in the primate for at least 18 months. In certain embodiments, the primate can be a monkey. In another embodiment, the primate can be a baboon. In a further embodiment, the primate can be a human. In one embodiment, at least 6 primates can be tested with the porcine heart. In another embodiment, at least 8 primates can be tested with the porcine heart. In a further embodiment, at least 10 primates can be tested with the porcine heart.

In one embodiment, hearts from the pigs of the invention, when transplanted into a primate can serve as a bridge to an allotransplant. In a specific embodiment, the hearts can be used as bridge organs for a time selected form but not limited to at least 1 month, at least 2 months or at least 3 months. In one specific embodiment, the porcine heart can be used as a bridge transplant and function in the primate for at least 9 months, at least 12 months or at least 15 months. In one embodiment, the primate can be a non-human primate. In another embodiment, the primate can be human.

For details on the transplantation procedure, see, for example, Handbook of Animal Models in Transplantation Research, Edited by D. V. Cramer, L. Podesta, L. Makowka 1994 CRC Press, for example, Chapters 3, 7, 8, 9 and 14; Cooper et al "Report of the Xenotransplantation Advisory Committee of the International Society for Heart and Lung Transplantation" December 2000 The Journal of Heart and Lung Transplantation, pp 1125-1165.

Kidneys

The use of GTKO pigs and/or transgenic pigs overexpressing human complement inhibitor genes for kidney xenotransplantation has largely overcome the problem of HAR, however problems remain with xeno-kidneys being rejected via AHXR. Yamada et al, (Nat Med. 2005 January; 11 (1): 32-4) obtained survival of >80 days in two baboons. Histology of many of the kidneys showed preserved structure, but the relatively intensive immunosuppressive regimen required to prolong graft survival resulted in complications. Less encouraging data in the GT-KO pig-to-baboon model were reported by Chen et al (Nat Med 2005:11:1295-8) where in contrast to the studies of Yamada et al., an elicited anti-nonGa1 antibody response was not prevented and AHXR resulted in graft failure.

Kidneys from the multi-transgenic pigs of the invention can decrease or eliminate xenorejection, exhibiting improved outcomes when used as a discordant transplant. In one embodiment, kidneys from the pigs of the invention remain functional in a non-human primate and do not exhibit xenorejection for 6 months or more. In another embodiment, kidneys from the pigs of the invention remain functional in a human for a year or more. In other embodiments, the transplanted kidneys of the present invention can function for a time period of at least 8 months, at least 9 months, at least 10 months, at least 11 months, at least 12 months, at least 15 months, at least 18 months, at least 21 month, at least 24 months, at least 36 months, or at least 48 months. Such transplants can be heterotopic or orthotopic.

Additionally, kidneys from pigs of the current invention containing further genetic modifications, for example, immunosuppressant transgenes such as CTLA4-Ig, will allow for clinically acceptable levels immunosuppression to be used, leading to fewer complications as a result of treatment.

Additional embodiments encompass, pigs of the current invention containing further genetic modifications, for example, immunosuppressant transgenes, for example, endothelial expression of immunosuppressant transgenes, such as CTLA4-Ig, allows for the use of a clinically relevant immunosuppressant regimen to be used in renal xenotransplantation.

In one embodiment, the porcine kidney can be transferred to a primate and can function in the primate for at least 6 months. In another embodiment, the porcine kidney can be transferred to a primate and can function in the primate for at least 9 months. In a further embodiment, the porcine kidney can be transferred to a primate and can function in the primate for at least 12 months. In a still further embodiment, the porcine kidney can be transferred to a primate and can function in the primate for at least 18 months. In certain embodiments, the primate can be a monkey. In another embodiment, the primate can be a baboon. In a further embodiment, the primate can be a human. In one embodiment, at least 6 primates can be tested with the porcine kidney. In another embodiment, at least 8 primates can be tested with the porcine kidney. In a further embodiment, at least 10 primates can be tested with the porcine kidney. In one specific embodiment, the porcine kidney can be used as a bridge transplant and function in the primate for at least 9 months. In another specific embodiment, the porcine kidney can be used as a bridge transplant and function in the primate for at least 12 months. In a further specific embodiment, the porcine kidney can be used as a bridge transplant and function in the primate for at least 15 months.

For details on the transplantation procedure, see, for example, Handbook of Animal Models in Transplantation Research, Edited by D. V. Cramer, L. Podesta, L. Makowka 1994 CRC Press, for example, Chapters 3, 7, 8, 9 and 14.

Pancreas

In certain embodiments, the pancreas from the multi-transgenic pigs of the invention can be used. Such pancreas can decrease or eliminate xenorejection, exhibiting improved outcomes when used as a discordant transplant.

In a further embodiment a kidney xenotransplant using kidneys from the pigs of the invention can be combined with a pancreas or pancreatic islet transplant. For example, this is currently performed in allotransplantation to treat patients with type 1 diabetes and late chronic kidney disease (reviewed by Wiseman, Curr Diab Rep. 2010 October; 10 (5): 385-91; Adv Chronic Kidney Dis. 2009 July; 16 (4): 278-87).

In one embodiment, the porcine pancreas can be transferred to a primate and can function in the primate for at least 6 months. In another embodiment, the porcine pancreas can be transferred to a primate and can function in the primate for at least 9 months. In a further embodiment, the porcine pancreas can be transferred to a primate and can function in the primate for at least 12 months. In a still further embodiment, the porcine pancreas can be transferred to a primate and can function in the primate for at least 18 months. In certain embodiments, the primate can be a monkey. In another embodiment, the primate can be a baboon. In a further embodiment, the primate can be a human. In one embodiment, at least 6 primates can be tested with the porcine pancreas. In another embodiment, at least 8 primates can be tested with the porcine pancreas. In a further embodiment, at least 10 primates can be tested with the porcine pancreas. In one specific embodiment, the porcine pancreas can be used as a bridge transplant and function in the primate for at least 9 months. In another specific embodiment, the porcine pancreas can be used as a bridge transplant and function in the primate for at least 12 months. In a further specific embodiment, the porcine pancreas can be used as a bridge transplant and function in the primate for at least 15 months. In alternate embodiments, the uses of the porcine pancreas disclosed herein can be used in combination with a kidney transplant.

Additional embodiments encompass, pigs of the current invention containing further genetic modifications, for example, immunosuppressant transgenes, for example, endothelial expression of immunosuppressant transgenes, such as CTLA4-Ig, allows for the use of a clinically relevant immunosuppressant regimen to be used in pancreatic/renal xenotransplantation.

For details on the transplantation procedure, see, for example, Handbook of Animal Models in Transplantation Research, Edited by D. V. Cramer, L. Podesta, L. Makowka 1994 CRC Press, for example, Chapters 3, 7, 8, 9 and 14.

Lungs

Xenotransplantation of porcine lungs is briefly reviewed in Ekser et al., Transplant Immun. 2009 21:87-92, but there is little data available. Lungs from the pigs of the current invention, will allow for further pre-clinical and clinical progress to be made. The transplanted lungs of the current invention can be a full lung or lung pair.

In embodiments of the present invention, the transplanted lungs of the present invention can function for a time period of at least 1 month, at least 2 months, at least 3 months, at least 4 months, at least 6 months, at least 8 months, at least 9 months, at least 10 months, at least 11 months, at least 12 months, at least 15 months, at least 18 months, at least 21 month, at least 24 months, at least 36 months, or at least 48 months. Such transplants can be heterotopic or orthotopic.

In other embodiments, the porcine lung can be transferred to a primate and can function in the primate for at least 6 months. In another embodiment, the porcine lung can be transferred to a primate and can function in the primate for at least 9 months. In a further embodiment, the porcine lung can be transferred to a primate and can function in the primate for at least 12 months. In a still further embodiment, the porcine lung can be transferred to a primate and can function in the primate for at least 18 months. In certain embodiments, the primate can be a monkey. In another embodiment, the primate can be a baboon. In a further embodiment, the primate can be a human. In one embodiment, at least 6 primates can be tested with the porcine lung. In another embodiment, at least 8 primates can be tested with the porcine lung. In a further embodiment, at least 10 primates can be tested with the porcine lung.

In one embodiment, lungs from the pigs of the invention, when transplanted into a primate can serve as a bridge to an allotransplant. In a specific embodiment, the lungs can be used as bridge organs for a time selected form but not limited to at least 7 days, at least 14 days, at least 21 days or at least 1 months. In one specific embodiment, the porcine lung can be used as a bridge transplant and function in the primate for at least 3 months, at least 4 months or at least 6 months. In another embodiment, the lung can be used as a bridge organ for 3-6 months. In one embodiment, the primate can be a non-human primate. In another embodiment, the primate can be human.

In particular embodiment, lungs are provided from transgenic animals that lack any expression of functional alpha 1,3 galactosyltransferase (GTKO) and specifically expresses at least one transgene in endothelial tissue. In another embodiment, lungs are provided from transgenic animals that lack any expression of functional alpha 1,3 galactosyltransferase (GTKO) and expresses at least one compliment inhibitor and specifically expresses at least one transgene in endothelial tissue selected from the group consisting of anti-coagulants, immunomodulators and cytoprotectants. In a specific embodiment, lungs are provided from transgenic animals with the following genetic modifications: GTKO, ubiquitous expression of at least one complement inhibitor, endothelial specific expression of at least three anticoagulants, and at least one immunomodulators. In an additional embodiment, the animal can also express at least one cytoprotective element. In a particularly specific embodiment, a lung from a transgenic animal is provided wherein the animal has the following genetic modifications: GTKO, DAF, CD46, and endothelial-specific expression of CD39, TM, EPCR, TFPI, CIITA-DN. In a further embodiment, the animal can also express A20 and HO-1.

Additional embodiments encompass, pigs of the current invention containing further genetic modifications, for example, immunosuppressant transgenes, for example, endothelial expression of immunosuppressant transgenes, such as CTLA4-Ig, allows for the use of a clinically relevant immunosuppressant regimen to be used in pulmonary xenotransplantation.

For details on the transplantation procedure, see, for example, Handbook of Animal Models in Transplantation Research, Edited by D. V. Cramer, L. Podesta, L. Makowka 1994 CRC Press, for example, Chapters 3, 7, 8, 9 and 14; Cooper et al "Report of the Xenotransplantation Advisory Committee of the International Society for Heart and Lung Transplantation" December 2000 The Journal of Heart and Lung Transplantation, pp 1125-1165.

Livers

The use of porcine livers in xenotransplantation has been reviewed by Hara (Liver Transpl. 2008 April; 14 (4): 425-34) and porcine livers from GTKO/CD46 pigs have recently shown parameters of liver function in the near-normal range (Ekser et al, Transplantation. 2010 Sep. 15; 90 (5): 483-93). In the human clinic, porcine livers are most likely to be used as a bridge transplant until a human derived liver becomes available for transplant. This use of livers from the pigs of the invention is detailed in the next section.

In other embodiments, the transplanted livers of the present invention can function for a time period of at least 3 months, at least 6 months, 8 months, at least 9 months, at least 10 months, at least 11 months, at least 12 months, at least 15 months, at least 18 months, at least 21 month, at least 24 months, at least 36 months, or at least 48 months.

Such transplants can be heterotopic or orthotopic. In another embodiment, the livers of the present invention can be used as a bridge transplant.

In one specific embodiment, the porcine liver can be used as a bridge transplant and function in the primate for at least 2 weeks, at least 3 weeks, or at least 4 weeks. In another specific embodiment, the porcine liver can be used as a bridge transplant and function in the primate for at least 2 weeks. In a further specific embodiment, the porcine liver can be used as a bridge transplant and function in the primate for at least 6 weeks. In another specific embodiment, the porcine liver can be used as a bridge transplant and function in the primate for at least 8 weeks. In a further specific embodiment, the porcine liver can be used as a bridge transplant and function in the primate for at least 12 weeks.

Additional embodiments encompass, pigs of the current invention containing further genetic modifications, for example, immunosuppressant transgenes, for example, endothelial expression of immunosuppressant transgenes, such as CTLA4-Ig, allows for the use of a clinically relevant immunosuppressant regimen to be used in hepatic xenotransplantation.

For details on the transplantation procedure, see, for example, Handbook of Animal Models in Transplantation Research, Edited by D. V. Cramer, L. Podesta, L. Makowka 1994 CRC Press, for example, Chapters 3, 7, 8, 9 and 14

Other Xenograft Applications

In addition to their use for therapeutic whole organ replacement, the porcine organs tissues and cells of the invention have additional therapeutic applications.

For example, porcine livers of the invention can be used as a bridge to an allotransplant. The use of pig-livers for bridge transplants is reviewed in depth by Ekser et al. (2009. Transplantation. November 15 88 (9): 1041-1049). In embodiments of the invention, porcine liver xenografts can function and serve to stabilize a patient undergoing liver failure for at least 5 days, at least 7 days, at least 14 days at least 21 days or at least 30 days. Such transplants can be used as a bridge until a suitable allotransplant liver becomes available.

Porcine liver tissues and cells of the invention can also be used in bioartificial liver (BAL) devices. BAL devices are used to provide temporary liver support to bridge a patient with rapidly deteriorating liver function to orthotopic liver transplant or to allow time for liver regeneration. There are several groups developing bioartificial liver devices, for example, Circe Biomedical (Lexington, Mass.), Vitagen (La Jolla, Calif.), Excorp Medical (Oakdale, Minn.), and Algenix (Shoreview, Minn.). The Circe Biomedical device integrates viable liver cells with biocompatible membranes into an extracorporeal, bioartificial liver assist system. Formerly developed by Circe and Arbios, this technology, HepaMate™, is now being developed by Hepalife (hepalifebiosystems.com/clinical-trials.php). Vitagen's ELAD (Extracorporeal Liver Assist Device) Artificial Liver is a two-chambered hollow-fiber cartridge containing a cultured human liver cell line (C3A). The cartridge contains a semipermeable membrane with a characterized molecular weight cutoff: This membrane allows for physical compartmentalization of the cultured human cell line and the patient's ultrafiltrate. Algenix provides a system in which an external liver support system uses porcine liver cells. Individual porcine hepatocytes pass through a membrane to process the human blood cells. Excorp Medical's device contains a hollow fiber membrane (with 100 kDa cutoff) bioreactor that separates the patient's blood from approximately 100 grams of primary porcine hepatocytes that have been harvested from, purpose-raised, pathogen-free pigs. Blood passes though a cylinder filled with hollow polymer fibers and a suspension containing billions of pig liver cells. The fibers act as a barrier to prevent proteins and cell byproducts of the pig cells from directly contacting the patient's blood but allow the necessary contact between the cells so that the toxins in the blood can be removed. In certain embodiments the porcine cells of the invention, used in a BAL device, can function and serve to stabilize a patient undergoing liver failure for up to 7 days, up to 14 days, or up to 30 days until a suitable allotransplant liver becomes available. Other uses of porcine livers, tissues or cells of the invention, including in extracorporeal artificial liver devices, in extracorporeal liver perfusion procedures, and for hepatic cell transplantation, as a bridge to an orthotopic allotransplant, or to support patient liver function and regeneration (as detailed for example, in Ekser et al. 2009. Transplantation. November 15 88 (9): 1041-1049) are also embodied herein.

Endothelial cells isolated from the cornea of animals of the invention can be used as a graft to treat cornea dysfunction. Optical surgical transplant procedures known as endothelial keratoplasty (EK) replace dysfunctional cornea endothelium with donor material. A procedure known as Deep Lamellar Endothelial Keratoplasty (DLEK) has become widely used since its introduction (Terry, M. A., Cataract and Refractory Surgery Today February 2004, p. 1-3). For a current review of the various EK procedures see Melles, September 2006 Cornea Volume 25 (8): 879-881.

Endothelial cells isolated from the retina of animals of the invention can be used as a graft to treat retina dysfunction, to treat diseases including acute macular degeneration or diabetes induced retinopathy. In certain embodiments, retinal endothelial cells can be used in the treatment of retinal dysfunction. In another embodiment, retinal endothelial cells can be used in the treatment of acute macular degeneration. In another embodiment, retinal endothelial cells can be used in the treatment of diabetes induced retinopathy.

Porcine tissues and cells from the animals of the invention can be used as vascular grafts. The current clinical source of vascular graft materials is limited to: vessels taken from the patient (autologous), tissue banks (allograft), materials derived from animals and highly processed to remove antigens and viable cells, or synthetic materials. There have also been efforts to develop bio-engineered vascular graft materials, however, challenges remain in this newly developing field, and such grafts are not yet clinically available (Campbell and Campbell, Curr Pharm Biotechnol. 2007 February; 8 (1): 43-50). For an extensive review of existing vascular graft materials and their applications, see for example Leon L, and Greisler H P. Expert Rev Cardiovasc Ther. 2003 November; 1 (4): 581-94. While autologous grafting is the method of choice, many patients do not have suitable vessels available for autologous grafting. Human derived allografts from tissue banks present risk of disease transmission to the recipient (Eastlund T. Cell Transplant. 1995 September-October; 4 (5): 455-77). Highly processed animal materials have shown problems with durability and immunogenicity (Lehalle B, Geschier C, Fiévé G, Stoltz J F. J Vasc Surg. 1997 April; 25 (4): 751-2).

Vascular tissues and cells from the animals of the invention can provide a safe alternate supply of vascular grafts. In certain embodiments of the present invention, vascular grafts can be selected from the group including, heart valves, femoral vein, femoral artery, aortoiliac artery, saphenous vein, ascending aorta, pulmonary artery, thoracic aorta, pulmonary artery, internal mammary artery, radial artery, or any other vessel that is currently used therapeutically as an autologous graft or allograft. In one embodiment, a single valved section of main pulmonary trunk may be used as a mono-cusp patch (www.AccessLifeNetHealth.org). In other embodiments, vascular materials from the animals of the invention can be used for replacement, shunting, patching or repair to treat a vascular defect or disease.

In further embodiments, vascular grafts from the animals of the invention can be used for vascular reconstructive surgery, coronary bypass surgery, or arterial or venous grafting. In certain embodiments, vascular grafts described herein can be used to treat a disease selected from the group including but not limited to atherosclerosis, coronary artery disease, peripheral vascular disease, and aortic aneurysm. In other embodiments, the vascular grafts disclosed herein can be used for peripheral vascular bypass surgery. In certain embodiments, the grafts disclosed herein can be used to treat peripheral arterial disease, critical limb ischemia or any other vascular occlusion.

In further embodiments, the porcine endothelial cells of the invention can also be used to seed vascular grafts, or can be used for seeding during coronary procedures, such as stenting or bypass surgery. Vascular graft materials can be allografts (human origin), or bioengineered devices, or any other material used as a vascular graft. Details on the use of endothelial cells for seeding following coronary procedures can be found for example in Kipshidze et al., J. Am. Coll. Cardiol. 2004; 44; 733-739 and details on the construction of vascular grafts and endothelial cell seeding methods can be found for example in Sarkar et al., J Biomed Mater Res B Appl Biomater. 2007 July; 82 (1): 100-8 and Villalona et al., Tissue Eng Part B Rev. 2010 June; 16 (3): 341-50. For a recent review of vascular engineered biomaterials (including xenograft materials) see Ravi and Chaikof, Regen Med. 2010 January; 5 (1): 107-20.

The methods of the invention also include methods of xenotransplantation wherein the transgenic organs, tissues or cells provided herein are transplanted into a primate and, after the transplant, the primate requires minimal or no immunosuppressive therapy. Reduced or no immunosuppressive therapy includes, but is not limited to, a reduction (or complete elimination of) in dose of the immunosuppressive drug(s)/agent(s) compared to that required by other methods; a reduction (or complete elimination of) in the number of types of immunosuppressive drug(s)/agent(s) compared to that required by other methods; a reduction (or complete elimination of) in the duration of immunosuppression treatment compared to that required by other methods; and/or a reduction (or complete elimination of) in maintenance immunosuppression compared to that required by other methods.

Additional embodiments encompass, pigs of the current invention allows for the use of a clinically relevant immunosuppressant regimen to be used in pulmonary xenotransplantation.

Further embodiments encompass, pigs of the current invention containing genetic modifications of the present invention allows for the use of a clinically relevant immunosuppressant regimen to be used in xenotransplantation. For example, immunosuppressant transgenes can be used. In one embodiment, endothelial expression of immunosuppressant transgenes can be used. The immunosuppressant transgene can be CTLA4-Ig.

The methods of the invention also include methods of treating or preventing organ dysfunction wherein after the transplantation of transgenic organs, tissues or cells, the transplant is repeated. The transplant may be performed twice, three times or more in any one primate. The transplant may occur once a year. The transplant may occur twice a year. The transplant may occur three times a year. The transplant may occur more than three times a year. The transplant may occur at various times over multiple years. The parameters of any one transplant, including, but not limited to, surgical procedures, delivery methods, donor tissues and/or cells used, immunosuppressive regimens used and the like, may be different or the same when compared to other transplants performed in the same primate.

In some embodiments, the method reduces the need for administration of anti-inflammatories to the host. In other embodiments, the method reduces the need for administration of anticoagulant to the host. In certain embodiments, the method reduces the need for administration of immunosuppressive agents to the host. In some embodiments, the host is administered an anti-inflammatory agent for less than thirty days, or less than 20 days, or less than 10 days, or less than 5 days, or less than 4 days, or less than 3 days, or less than 2 days, or less than one day after transplantation. In some embodiments, the host is administered an anticoagulant agent for less than thirty days, or less than 20 days, or less than 10 days, or less than 5 days, or less than 4 days, or less than 3 days, or less than 2 days, or less than one day after transplantation. In some embodiments, the host is administered an immunosuppressive agent for less than thirty days, or less than 20 days, or less than 10 days, or less than 5 days, or less than 4 days, or less than 3 days, or less than 2 days, or less than one day after transplantation.

The recipient (host) may be partially or fully immuno-suppressed or not at all at the time of transplant. Immuno-suppressive agents/drugs that may be used before, during and/or after the time of transplant are any known to one of skill in the art and include, but are not limited to, MMF (mycophenolate mofetil (Cellcept)), ATG (anti-thymocyte globulin), anti-CD154 (CD40L), alemtuzumab (Campath), CTLA4-Ig (Abatacept/Orencia), belatacept (LEA29Y), sirolimus (Rapimune), tacrolimus (Prograf), anti-CD20 (Rituximab), daclizumab (Zenapax), basiliximab (Simulect), infliximab (Remicade), cyclosporin, deoxyspergualin, soluble complement receptor 1, cobra venom, methylprednisolone, FTY720, everolimus, anti-CD154-Ab, leflunomide, anti-IL-2R-Ab, rapamycin, and human anti-CD154 monoclonal antibody. One or more than one immunosuppressive agents/drugs may be used together or sequentially. One or more than one immunosuppressive agents/drugs may be used for induction therapy or for maintenance therapy. The same or different drugs may be used during the induction and maintenance stages. In one embodiment, daclizumab (Zenapax) is used for induction therapy and tacrolimus (Prograf) and sirolimus (Rapimune) is used for maintenance therapy. In another embodiment, daclizumab (Zenapax) is used for induction therapy and low dose tacrolimus (Prograf) and low dose sirolimus (Rapimune) is used for maintenance therapy. In one embodiment, alemtuzumab (Campath) is used for induction therapy. See Teuteberg et al., Am J Transplantation, 10 (2): 382-388. 2010; van der Windt et al., 2009, Am. J. Transplantation 9 (12): 2716-2726. 2009; Shapiro, The Scientist, 20 (5): 43. 2006; Shapiro et al., N Engl J Med. 355:1318-1330. 2006. Immunosuppression may also be achieved using non-drug regimens including, but not limited to, whole body irradiation, thymic irradiation, and full and/or partial splenectomy. These techniques may also be used in combination with one or more immunosuppressive drug/agent.

Sufficient time to allow for engraftment (for example, 1 week, 3 weeks, and the like) is provided and successful engraftment is determined using any technique known to one skilled in the art. These techniques may include, but are not limited to, One or more techniques may be used to determine if engraftment is successful. Successful engraftment may refer to relative to no treatment, or in some embodiments, relative to other approaches for transplantation (i.e., engraftment is more successful than when using other methods/tissues for transplantation). In some cases, successful engraftment is illustrated by a reduced need for immunosuppression. This reduced need for immunosuppression may include the lowering of a dose of one or more immunosuppressive drugs/agents, a decrease in the number of types of immunosuppressive drugs/agents required, a shorter duration of immunosuppression, and/or lower or no maintenance immunosuppression.

In one embodiment, successful engraftment may be assessed by monitoring or testing for functionality (partial or full) of the transplanted tissue. For heart xenografts this may include, for example, monitoring by palpation, or by continuous telemetry. Progressive bradycardia and decreasing QRS amplitude are predictive of imminent graft failure (heterotopic abdominal heart xenotransplant; for technique details see, for example, Adams et al., 1999 Ann Thorac Surg. July; 68 (1): 265-8). Other methods employed by those in the art to monitor cardiac xenograft function (in a heterotopic thoracic heart xenotransplant) include, for example, continuously analyzing heart rate, rhythm and ST-segment in ECG-leads II and V5 (Sirecust 960; Siemens, Erlangen, Germany); continuously monitoring arterial blood pressure and cardiac function via a catheter in the femoral artery (Pulsion, Munich, Germany) and a central venous catheter (Arrow, Erding, Germany) introduced via the cephalic vein; measuring cardiac output with the femoral arterial thermodilution technique (PiCCO; Pulsion); assessing heart rate of the recipient and the graft by external ECG positioned over the right chest wall daily postoperatively; conducting echocardiographic examinations of the graft in regular intervals using an utrasonographic scanner and a 10-MHz phased-array transducer (Sonos 5500; Hewlett Packard, Andover, MA, USA) and performing a CT angiogram (Bauer et al., 2010 Xenotransplantation 17:243-249).

EXAMPLES

Generation and Characterization of Multi-Transgenic Pigs with Endothelial Specific Expression, Using Two Different Anticoagulant Genes.

Example 1: Construction of Endothelial Specific Vectors for Production of Transgenic Pigs Endothelium-specific expression provides a strategy to limit expression of bioactive transgenes that could have adverse effects if expressed ubiquitously. Two expression systems used (in this example) are the porcine ICAM-2 promoter/enhancer system and the mouse Tie-2 promoter/enhancer system.

Examples of anticoagulant transgenes expressed via these endothelial specific vector systems include:
1. human CD39 (vector pREV859B, which utilizes the Tie-2 promoter/enhancer and vector pREV861 which utilizes the ICAM-2 promoter/enhancer),
2. human thrombomodulin (vector pREV872, which utilizes the ICAM-2 promoter/enhancer),
3. human endothelial protein C receptor (vector pREV873, which utilizes the ICAM-2 promoter/enhancer), 4. human tissue factor pathway inhibitor (vector pREV871, which utilizes the ICAM-2 promoter/enhancer).

All of these transgenes encode proteins that can inhibit vascular thrombosis during xenotransplantation. These vectors have been shown to drive transgene expression in transiently or stably-transfected porcine endothelial cells. FIG. 1 shows expression analysis of TM and EPCR in immortalized porcine endothelial cells (IPEC) using flow cytometry. Endothelium specific vectors herein can be used to produce multi-transgenic pigs that exhibit good viability while producing therapeutic anticoagulants locally within the donor organs, cells, or tissues for support of xenotransplantation.

Vector Construction:

The backbone vector for these constructs contained 5' and 3' chicken β-globin insulators, a multiple cloning site (MCS) and an SV40 poly adenylation signal. Transgene inserts were subcloned into the MCS upstream of the SV40 polyadenylation signal using appropriate restriction sites described below for each vector.

The pREV859B, Tie-2 CD39 vector was built by insertion of a Nhe1/Sal1 fragment containing the Tic-2 enhancer/promoter, and an Xho1 fragment containing the CD39 transgene into the base vector.

The pREV861, ICAM-2 CD39 vector was built by excision of the Tie-2 enhancer and promoter in the pREV859B vector with BssHII and BstB1 and insertion of a BssHII/BstBI fragment containing the ICAM-2 enhancer and promoter.

The pREV871, ICAM-2 TFPI vector was built by excising the Tie-2 enhancer/promoter from a previously built Tie-2 TFPI vector and replacing it with a BssHII/BstB1 fragment containing the ICAM-2 enhancer and promoter.

The pREV872, ICAM-2 TM vector was built by insertion of an Spe1/Not1 ICAM-2 enhancer/promoter fragment, as well as a Not1/Sal1 fragment containing the TM transgene into the base vector.

The pREV873, ICAM-2 EPCR vector was built by insertion of an SpeI/NotI fragment containing the ICAM-2 enhancer/promoter, and a NotI/SpeI fragment containing the EPCR transgene into the base vector.

Example 2: Cell Line Preparation for Nuclear Transfer

Isolation of Cell Lines:

One cell line (183-6-6) was used as the genetic background for transfections to add the additional transgenes, and ultimately for nuclear transfer to generate pigs. This cell lines was produced by breeding of GTKO pigs (Dai et al., (2002) Nature biotechnology 20, 251-255; Phelps et al., Science, (2003) 299:411-414) with ubiquitously expressing hCD46 transgenic pig lines (Loveland et al., Xenotransplantation, 2004, 11:171:183). The 186-6-6 cell line was confirmed by genotype and phenotype as homozygous GTKO and hCD46 transgenic. The cells were prepared for use in NT as follows: A fetal fibroblast cell line was isolated from fetus 183-6-6 at day 36 of gestation. The Fetus was mashed through a 60-mesh metal screen using curved surgical forceps slowly so as not to generate excessive heat. The cell suspension was then pelleted and resuspended in DMEM containing 20% fetal calf serum and Antibiotic-Antimycotic (Invitrogen, Carlsbad, CA). Cells were cultured four days, and cryopreserved.

Plasmid Fragment Preparation for Transfection:

The pREV 859B plasmid fragment was prepared for transfection by restriction enzyme digestion with BsmBI and AhdI. pREV 861 was prepared by digestion with BsmBI and Eci1. pREV 872 was prepared by digestion with Drd1. PREV 873 was prepared by digestion with BsmBI and EciI (all restriction enzymes from New England Biolabs, Ipswitch, MA). The plasmid fragments generated by digestion were separated on a 1% low melt agarose gel (Cambrex, East Rutherford, NJ) to remove the plasmid backbone. The transgene-containing cassette fragment of interest was excised and incubated twice in 2 volumes of 1× agarose buffer on ice for 15 minutes. After removing the buffer, the gel was melted at 65° C. 10 minutes. After 10 minutes at 42° C., 1 uL Agarase (New England Biolabs) per 100 μL of gel melt and incubated minimum 1 hour at 42° C. One-tenth volume of 3M Sodium Acctate was added to the gel melt and incubated on ice 15 minutes. Centrifugation at 15000 rpm for 15 minutes at 4° C. separates any undigested agarose. Two volumes of 100% ethanol were added to the supernatant and centrifugation was used to pellet the DNA fragment. 70% ethanol was used to wash the pellet before drying at 37° C. The pellet was resuspended in TE.

Transfection, Selection, Harvesting of Colonies for Screening:

Porcine fibroblasts from pig the 183-6-6 line were transfected with either PREV872 (pICAM-2 hTM), or pREV859B (Tie-2 hCD39) and pREV828 (a Puromycin selectable marker gene vector)

pREV859B (Tie-2/hCD39) Transfection

Approximately 5 million cells were co-electroporated with 3 μg of the pREV859B vector and 0.5 μg of the selectable marker vector. Forty-eight hours post transfection, transfected cells were selected with the addition of 1 μg/ml of the antibiotic Puromycin (InvivoGen, San Diego, CA) in 20×10 cm dishes at a density of approximately 25,000 cells per dish. Media was changed 72 hours post initiation of puromycin selection. Colonies were harvested 9 days post initiation of selection. 60 colonies grew and were split into two samples: one for PCR analysis and one for expansion. PCR analysis for pREV859B was performed as described herein. Thirty-two PCR positive colonies were pooled and cryopreserved for future use in nuclear transfer.

pREV872 (ICAM2/hTM) Transfection

Approximately 5 million cells were co-electroporated with 5 μg of the pREV872 vector and 0.5 μg of the selectable marker vector. Forty-eight hours post transfection, transfected cells were selected with the addition of 1 μg/ml of the antibiotic Puromycin (InvivoGen, San Diego, CA) in 30×10 cm dishes at a density of approximately 65,000 cells per dish. Media was changed 72 hours post initiation of puromycin selection. Colonies were harvested 14 days post initiation of selection. 22 colonies grew and were split into two samples: one for PCR analysis and one for expansion. PCR analysis for pREV872 was performed as described herein. Three PCR positive colonies were pooled and cryopreserved for future use in nuclear transfer.

Similar procedures were used for transfection, selection and harvesting of colonies using the pREV861 vector and the pREV873 (pICAM-2 huEPCR) vector co-transfected in combination with the pREV872 (pICAM-2 huTM) vector.

Example 3: Production of Multi-Transgenic Pigs by Nuclear Transfer (NT)

Various methods can be used to produce the multi-transgenic pigs of the current invention. The following is one example in which donor cells used (line 227-3 and line 183-6-6) were the genetic background homozygous GTKO (lacked any function αGT) and were also transgenic for CD46. Donor cells were transfected, selected and screened positive for the pREV859B, pREV861, pREV872, and/or pREV873 vectors, as described in Example 2, prior to being used for NT. In some cases, multiple colonies of transfected and selected cells, all screening positive for the transgene(s), were pooled together prior to their use in NT.

Donor cells (fetal or adult fibroblast cells) for NT were cultured in Dulbecco's Modified Eagle Medium (DMEM, Gibco, cat #11995-065) supplemented with 10-20% fetal calf serum and 0-4 ng/ml basic fibroblast growth factor, in a humidified incubator at 5% 02, 5% CO2 balanced with nitrogen at 37° C. For culture, cells were seeded 3-7 days prior to the nuclear transfer procedure, at an appropriate dilution such that the cells would reach confluency 24-48 hours prior to nuclear transfer. On the day of nuclear transfer, donor cells were harvested about 30-45 minutes before use in embryo reconstruction by using Trypsin-EDTA (Gibco, cat #25300-054), making a single cell suspension in suitable holding medium (e.g. Hepes buffered M199, Gibco cat #12350-039).

NT procedures were performed on in vitro matured oocytes (Desoto Biosciences, Christiansburg, VA) using methods well known in the art (see, e.g., Polejaeva, et al., (2000) Nature 407, 86-90, Dai et al., (2002) Nature biotechnology 20, 251-255, Campbell et al., (2007) Theriogenology 68 Suppl 1, S214-231, Vatja et al., (2007) Reprod Fertil Dev 19, 403-423). Electrical fusion and activation of reconstructed oocytes was performed using an ECM2001 Electrocell Manipulator (BTX Inc., San Diego). Fused and activated nuclear transfer embryos were held in culture in phosphate buffered NCSU-23 medium (J Rprod Fertil Suppl. 1993; 48:61-73) for 1-4 h at 38.5° C., and then transferred to the oviduct of an estrus-synchronized recipient gilt. Crossbred gilts (large white/Duroc/Landrace) (280-400 lbs) were synchronized as recipient animals by oral administration of 18-20 mg Matrix (Altrenogest, Hoechst, Warren, NJ) mixed into their feed. Matrix was fed for 14 consecutive days. Human Chorionic Gonadotropin (hCG, 1000 units; Intervet America, Millsboro, DE) was administered intramuscularly 105 h after the last Regu-Mate treatment. Embryo transfers were performed by mid-ventral laparotomy 22-26 h after the hCG injection. Pregnant Mare Serum Gonadotropin (PMSG, 1000 IU) and hCG (500 IU) we used on day 10 and 13 post transfer for maintenance of pregnancy. Pregnancy was confirmed via ultrasonography 28 days post-transfer. Pregnancies were monitored thereafter on a weekly basis. All piglets were born via natural parturition.

Example 4: Genotyping of Cells and Transgenic Animals by PCR and Southern Blot Analysis Genotype Analysis:

Genomic DNA was extracted from transfected cells, and blood or tissue samples from each piglet to be tested. In brief, tissue samples were lysed overnight at 60° C. in a shaking incubator with approximately 1 ml lysis solution (50 mM Tris pH8.0, 0.15 M NaCl, 0.01 M EDTA, 1% SDS, 25% Sodium perchlorate and 1% of β-Mercaptoethanol and Proteinase K) per 175 mg tissue. DNA was precipitated with isopropyl alcohol following phenol/chloroform extraction. Resolubilized DNA was treated with RNase (1 mg/ml)+ RNase T1 (1000 U/μl) at 37° C. for 1 hour, with proteinase K (20 mg/ml) at 55° C. for 1 hour, extracted with phenol/chloroform, precipitated and resuspended in Tris Ethylenedeaminetetraacetic acid (EDTA). DNA was isolated from whole blood samples using a DNA isolation kit for mammalian blood (Roche Diagnostics Indianapolis, IN).

For Southern blot analysis, about 10 μg of DNA was digested with the appropriate restriction enzyme (detail below) and separated on a 1% agarose gel. Following electrophoresis, the DNA was transferred to a nylon membrane and probed with a 3'-end digoxigenin-labeled probe (probe sequence below). Bands were detected using a chemiluminescent substrate system (Roche Diagnostics, Indianapolis, IN).

Primers and Probes:

pREV859B—Tie-2/huCD39

The presence of integrated pREV859B construct was determined by PCR using primers CD39L3 and CD39R3 which target a 585 bp fragment within the CD39 coding sequence.

```
CD39L3:
AGTATGGGATTGTGCTGGATG

CD39R3:
CATAGAGGCGAAATTGCAGAG
```

The presence of integrated pREV859B construct was confirmed by Southern blot analysis using a BanHI digest and probing with probe CD39L3/R3-dig.

```
CD39L3/R3-dig probe sequence:
AGTATGGGATTGTGCTGGATGCGGGTTCTTCTCACACAAGTTTATA

CATCTATAAGTGGCCAGCAGAAAAGGAGAATGACACAGGCGTGGT

GCATCAAGTAGAAGAATGCAGGGTTAAAGGTCCTGGAATCTCAAA

ATTTGTTCAGAAAGTAAATGAAATAGGCATTTACCTGACTGATTGC

ATGGAAAGAGCTAGGGAAGTGATTCCAAGGTCCCAGCACCAAGAG

ACACCCGTTTACCTGGGAGCCACGGCAGGCATGCGGTTGCTCAGGA

TGGAAAGTGAAGAGTTGGCAGACAGGGTTCTGGATGTGGTGGAGA

GGAGCCTCAGCAACTACCCCTTTGACTTCCAGGGTGCCAGGATCAT

TACTGGCCAAGAGGAAGGTGCCTATGGCTGGATTACTATCAACTAT

CTGCTGGGCAAATTCAGTCAGAAAACAAGGTGGTTCAGCATAGTCC

CATATGAAACCAATAATCAGGAAACCTTTGGAGCTTTGGACCTTGG

GGGAGCCTCTACACAAGTCACTTTTGTACCCCAAAACCAGACTATC

GAGTCCCCAGATAATGCTCTGCAATTTCGCCTCTATG
```

In some cases, probe Tie2L/R-dig was used:

```
TGGCAGCTTCTGCTTGCTTCGATCAGCTGCCAGTTAGGTAGCAACA

AACTTGGGATAAGTAACATAAGGAGGGTAGTTACAAGCAACAAGT

CATCTTAGAACCTCTGCTAAGTCAAGACCCAGAGGCAAGAAGAAG

TTGGGAATTGGTTGGGGAAAAGTAGGGGGCTCCACCTTGCTGGCTG

GCTGAGTCACAAGCAAGGAATTTCCCCACCAGACAACCCAGCTTTT

TAACAGAAGCCCAGGAACGCAAAGCTTTAAGCCCTTCTCTTCGTTT
```

-continued

TCCTGATACAAAGATGCTCTTTTGCAGTCAAAGCAGCCAGAGTCAG

CCCCACACATATATAAACAGATTAGCTCAGGAATGGAGGCCTGCCC

TGAA

PREV861—pICAM2/CD39

The presence of integrated pREV861 construct was determined by PCR using primers CD39L3 and CD39R3 which targets a 585 bp fragment within the CD39 coding region.

```
CD39L3:
AGTATGGGATTGTGCTGGATG

CD39R3:
CATAGAGGCGAAATTGCAGAG
```

The presence of integrated pREV861 construct was confirmed by Southern blot analysis using a BamHI digest and probing with probe CD39L3/R3-dig.

```
CD39L3/R3-dig probe sequence:
AGTATGGGATTGTGCTGGATGCGGGTTCTTCTCACACAAGTTTATA

CATCTATAAGTGGCCAGCAGAAAAGGAGAATGACACAGGCGTGGT

GCATCAAGTAGAAGAATGCAGGGTTAAAGGTCCTGGAATCTCAAA

ATTTGTTCAGAAAGTAAATGAAATAGGCATTTACCTGACTGATTGC

ATGGAAAGAGCTAGGGAAGTGATTCCAAGGTCCCAGCACCAAGAG

ACACCCGTTTACCTGGGAGCCACGGCAGGCATGCGGTTGCTCAGGA

TGGAAAGTGAAGAGTTGGCAGACAGGGTTCTGGATGTGGTGGAGA

GGAGCCTCAGCAACTACCCCTTTGACTTCCAGGGTGCCAGGATCAT

TACTGGCCAAGAGGAAGGTGCCTATGGCTGGATTACTATCAACTAT

CTGCTGGGCAAATTCAGTCAGAAAACAAGGTGGTTCAGCATAGTCC

CATATGAAACCAATAATCAGGAAACCTTTGGAGCTTTGGACCTTGG

GGGAGCCTCTACACAAGTCACTTTTGTACCCCAAAACCAGACTATC

GAGTCCCCAGATAATGCTCTGCAATTTCGCCTCTATG
```

PREV872—pICAM2/huTM

The presence of integrated pREV872 construct was determined by PCR using primers TML and TMR which targets a 533 bp fragment within the TM coding region.

```
TML:
ACTGCAGCGTGGAGAACGGC

TMR:
GGTGTTGGGGTCGCAGTCGG
```

The presence of integrated pREV872 construct was confirmed by Southern blot analysis using a BamHI digest and probing with probe TML/R-dig.

```
TML/R-dig probe sequence:
ACTGCAGCGTGGAGAACGGCGGCTGCGAGCACGCGTGCAATGCGA

TCCCTGGGGCTCCCCGCTGCCAGTGCCCAGCCGGCGCCGCCCTGCA

GGCAGACGGGCGCTCCTGCACCGCATCCGCGACGCAGTCCTGCAAC

GACCTCTGCGAGCACTTCTGCGTTCCCAACCCCGACCAGCCGGGCT
```

-continued

CCTACTCGTGCATGTGCGAGACCGGCTACCGGCTGGCGGCCGACCA

ACACCGGTGCGAGGACGTGGATGACTGCATACTGGAGCCCAGTCC

GTGTCCGCAGCGCTGTGTCAACACACAGGGTGGCTTCGAGTGCCAC

TGCTACCCTAACTACGACCTGGTGGACGGCGAGTGTGTGGAGCCCG

TGGACCCGTGCTTCAGAGCCAACTGCGAGTACCAGTGCCAGCCCCT

GAACCAAACTAGCTACCTCTGCGTCTGCGCCGAGGGCTTCGCGCCC

ATTCCCCACGAGCCGCACAGGTGCCAGATGTTTTGCAACCAGACTG

CCTGTCCAGCCGACTGCGACCCCAACACC

PREV873—pICAM2/huEPCR

The presence of integrated pREV873 construct was determined by PCR using primers EPCR5' and 858R3381 which targets a 692 bp fragment from within the huEPCR coding region to outside of the huEPCR coding region

```
EPCR5':
TCCTGGGCTGTGAGCTGCCT

858.R3381:
CCCCCTGAACCTGAAACATA
```

The presence of integrated pREV873 construct was confirmed by Southern blot analysis using a BamHI digest and probing with EPCR5'/3'dig probe.

```
EPCR3'/3' dig probe sequence:
TCCTGGGCTGTGAGCTGCCTCCCGAGGGCTCTAGAGCCCATGTCTT

CTTCGAAGTGGCTGTGAATGGGAGCTCCTTTGTGAGTTTCCGGCCG

GAGAGAGCCTTGTGGCAGGCAGACACCCAGGTCACCTCCGGAGTG

GTCACCTTCACCCTGCAGCAGCTCAATGCCTACAACCGCACTCGGT

ATGAACTGCGGGAATTCCTGGAGGACACCTGTGTGCAGTATGTGCA

GAAACATATTTCCGCGGAAAACACGAAAGGGAGCCAAACAAGCCG

CTCCTACACTTCGCTGGTCCTGGGCG
```

Example 5: Phenotypic Analysis (pCTLA4-1g) of Tissues from Transgenic Pigs

Western Blot for pCTLA4-Ig Expression:

Tissue and cell lysates can be prepared by homogenization in the presence of protease inhibitors (Thermo Scientific, Rockford, IL) followed by the addition of SDS (1% final concentration) and centrifugation to remove residual cellular debris. Protein concentration is determined with a bicinchoninic acid (BCA) protein assay kit (Pierce, Rockford, IL). Heat-denatured and β-mercaptoethanol-reduced samples (10-20~g protein) are fractionated on 4-12% Bis-Tris SDS gradient gels (Invitrogen, Carlsbad, CA). Recombinant human CTLA4-Ig/Fc (R&D Systems, Minneapolis, MN) is used as a standard control protein. Following electrophoresis, proteins are transferred to a nitrocellulose membrane, stained with Memcode Protein Stain (Thermo Scientific) for total protein visualization, and blocked with casein-blocking buffer (Sigma-Aldrich., St. Louis, MO). The blocked membrane is incubated in rabbit anti-human IgG1-horseradish peroxidase (HRP) (The Binding Site, San Diego, CA), which recognizes the human IgG1 heavy chain region of pCTLA4-Ig. Immunoreactive bands are detected with Super Signal West Pico Chemiluminescent Substrate (Thermo Scientific) and photographic imaging.

Example 6: Phenotypic Analysis of Animals Expressing Transgenes in Endothelium In order to screen for expression of the various transgenes in the endothelium of transgenic pigs produced, aortic endothelial cells were procured from animals determined to be genotypically positive and examined via flow cytometry.
Aortic Endothelial Cell Isolation 3 to 6 inches of descending aorta (vessel) were removed from the euthanatized pig and placed in RPMI+Antibiotic/Antimycotic (Invitrogen, Carlsbad, CA). The vessel was thoroughly washed using DBPS (Mediatech, Inc. Manassas, VA) by flushing the interior and exterior of the vessel with multiple volumes of DPBS to remove blood. The exterior of the vessel was trimmed of any excess tissue such as muscle and fat. Both ends of vessel were clamped closed. The vessel was filled with RPMI+100 units of activity/ml of collagenase type 4 (Worthington Biochemical, Lakewood, NJ). It was then incubated for 15-30 min at 37 C. The clamps were removed and the vessel contents were emptied into a 15 ml tube and the vessel was flushed with an additional 10 mls of RPMI. This collagenase digestion was repeated up to three times. The fractions were kept separate. The cell fractions were pelleted and washed with 10 mls of RPMI. Each cell fraction was seeded in separate 10 cm plates in 10 mls of RPMI+10% FBS+1× Antibiotic/antimycotic.
Detection of Anticoagulant Transgene Expression (TM and CD39) on Endothelial Cells Via Flow Cytometry Endothelial cells were harvested 24-72 hr post isolation to measure expression of TM or CD39 by flow cytometry. The number of endothelial cells was counted and adjusted by dilution or concentration to $10 \times 10^6$ per ml in Stain buffer (BD Pharmingen, San Diego, CA). The cells were exposed to antibody as per manufacturer's suggestion at a concentration of 20 µl of antibody per $1.0 \times 10^6$ cells.

For TM expression: PE labeled Anti-human CD141 (BD Pharmingen, San Diego, CA) was used. PE mouse IgG1 k was used as the isotype control.

For CD39 expression: PE labeled Anti-human CD39 (BD Pharmingen, San Diego, CA) was used. PE mouse IgG2b was used as the isotype control.

Cells were incubated with the appropriate antibody for 30 min at 4 C. Cells were then washed with 2-5 ml of stain buffer. Cells were resuspended in 0.5 ml of Stain buffer. Antibody labeling was recorded by measuring PE expression level of 10,000 cells per sample using flow cytometry.
Histology and Immunofluorescence (IF):

Porcine endothelial tissue samples can be removed and either fixed in 10% formalin or frozen down in blocks of OCT (Electron Microscopy Sciences, Hatfield, PA). Frozen sections are cut at 5 µm on a cryostat and are stained with rabbit anti-human TFPI (polyclonal, American Diagnostica, Stamford, CT, #4901), sheep anti-human IgG1 (polyclonal, The Binding Site, Birmingham, UK, #AUOO6), mouse anti-human CD46 (clone O.N. 137, mIgG2a, U.S. Biological, Swampscott, MA), mouse anti-human CD39 ((clone A1, AbD Serotec, Oxford, UK), mouse anti-human CD201 (EPCR) (clone RCR-252, BD Pharmingen, San Jose, CA) or mouse anti-human CD141 (TM) (clone 1A4, BD Pharmingen). Isotype controls are run for rabbit IgG (Jackson ImmunoResearch, West Grove, PA), sheep IgG (Jackson), mouse IgG2a (BD Pharmingen) and mouse IgG1 (clone MOPC-31C, BD Pharmingen), respectively. Immunofluorescent (IF) staining is performed using a 3-step procedure.

Frozen sections are dried and fixed in cold acetone (Sigma, St. Louis, MO), followed by avidin-biotin blocking (Invitrogen, Carlsbad, CA). Secondary Ab host species scrum blocking steps ac also included (10% Donkey scrum, Jackson). Primary Abs are diluted in PBS and incubations are performed for 1 h at room temperature in a humidified chamber. The secondary Ab used is biotinylated donkey anti-(rabbit, sheep, or mouse) IgG for 45 mm and the tertiary Ab used is fluorescein-conjugated strep avidin for 30 mm (Jackson). Slides are washed in PBS between steps, are cover slipped using 22×30 mm coverslips (VWR, West Chester, PA) and are preserved using Slowfade with DAPI (Invitrogen). IF pictures can be taken using an Olympus DP71 camera on a Provis microscope, and analyzed using DP controller software (Olympus, Center Valley, PA) with a magnification of 200×.
Cell Smears for IF Analysis:

In some cases cell-smears can be prepared from organs and tissues containing endothelium, to determine presence of the transgenic protein via IF. The following procedure is followed:

Approximately 1×1 cm of tissue is placed in a 4 ml snap cap tube and 1 ml of DMEM+collagenase at 50-100 units activity/ml is added. The tube is incubated for 10 min at 37 C. Next the tissue is minced using a long handle scissor by placing the scissors in the tube and opening and closing scissor blades for 3-5 min. The tube is then incubated for 10 min at 37 C. Mincing is repeated for 3-5 more minutes, 2 ml of DPBS is added and the resulting cells are pelleted via centrifugation. They are then washed in 3 ml DPBS and resuspended in 250 µl of Cytofix Fixation Buffer (BD Biosciences). They are incubated in the buffer for 20 min at 4 C. Next, 2 ml of DPBS is added and the cells are pelleted. They are washed in 3 ml of distilled water and then resuspended in 1 ml of distilled water. 5 µl of cell solution is placed on a superfrost plus glass slide. Slides are allowed to air dry and can be stored at 4 C for up to one week. Slides are stained following the same IF protocol as for blocked and sectioned tissues (see above).
Real Time PCR (RTPCR) to Measure TM Transcript in Samples from Multi-Transgenic Pigs Lung, liver, heart, aorta and kidney samples were obtained from piglets 448-01, 448-02, 448-03 and 450-06 postmortem. Tissues were homogenized and total RNA was isolated using Trizol (Invitrogen, Carlsbad, CA) following the procedure of Chomeyznski and Sacchi (Anal Biochem. 1987 April; 162 (1): 156-9). Reverse transcription was performed using the iScript cDNA Synthesis Kit (Bio-Rad Laboratories, Inc., Hercules, CA) according to the manufacturer's instructions. A reaction mix containing 1 µg of RNA was formulated for the sample, a non-reverse transcriptase and a non-template control reaction. In addition, all the samples were treated with DNase I (Invitrogen, Carlsbad, CA) to prevent DNA contamination.

PCR primers for the amplification of hTM were designed from the 872 construct sequence (forward primer: TTCAGAGCCAACTGCGAGTA and reverse primer: AACCGTCGTCCAGGATGTAG). cDNA was amplified using iQTMSYBR Green Supermix in the MyiQ Reverse Transcription PCR Detection System (Bio-Rad Laboratories, Inc., Hercules, CA, USA). Complementary DNA was amplified using SYBR Green PCR Master Mix in the ABI Prism (R) 7000 Sequence Detection System (Applied Biosystems, Foster City, CA). A no reverse transcriptase, a wild type and a no template sample were included in every plate as negative controls. Three replicates of every tissue were analyzed. The copy number of hTM in all the tissues was calculated using the standard curve method.

Results

Multitransgenic Pigs Produced, Genotypic and Phenotypic Characterization

Figure 4:
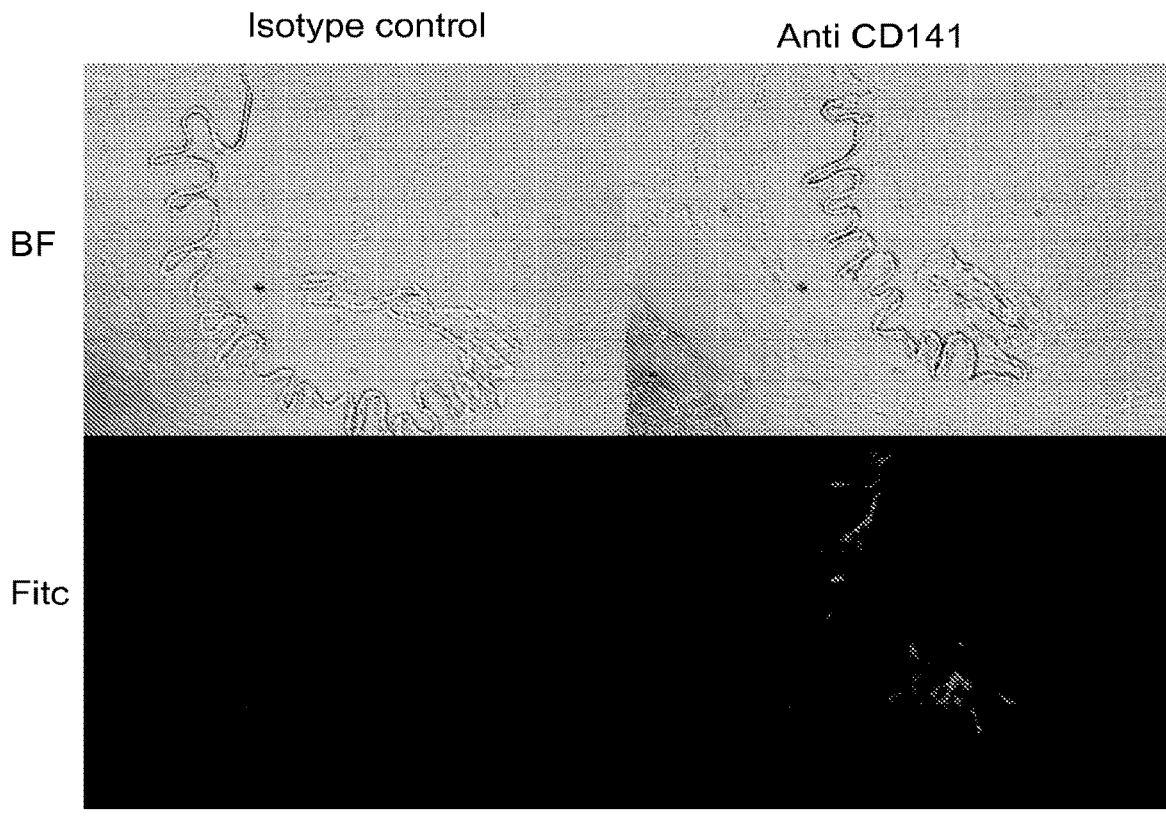
FIG. 4 presents images of cells stained with FITC labeled anti-human TM antibody. TM expression was observed in the endothelium of a vessel from a tail biopsy of piglet 424-03. The background fluorescence (BF) shows vessel morphology. Isotype control is also shown.
Figure 5:
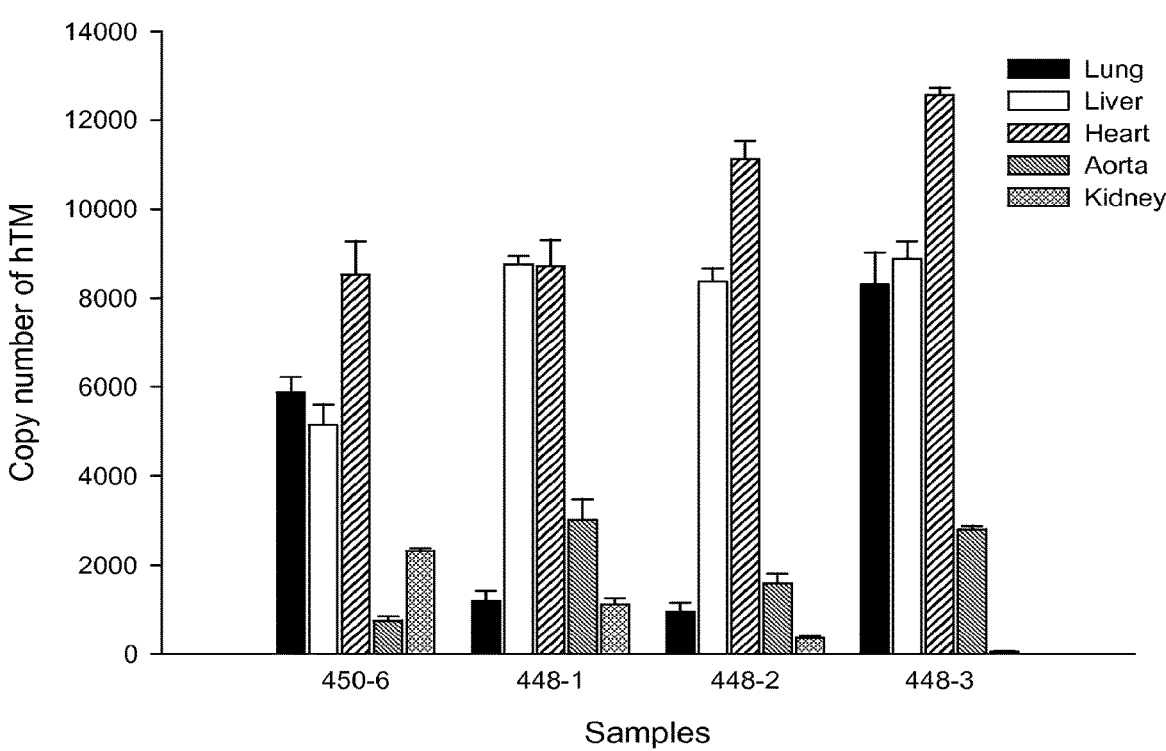
FIG. 5 shows TM transcript expression by RTPCR in samples obtained from multi-transgenic piglets 448-01, 448-02, 448-03 and 450-06. TM copy number shown is the copy number of hTM present in 50 ng of cDNA.

Five sessions of nuclear transfer, using 183-6-6 cells screened transgenic for the pREV859B, pREV861, pREV872 or pREV873 anticoagulant transgenes, as nuclear donors, resulted in the production of five litters of piglets. Thirty three piglets were born, and 23 were alive after birth. Fourteen of these piglets screened positive for an anticoagulant transgene in their genome (thirteen transgenic for TM, and one transgenic for CD39). In some cases, two different anticoagulant transgenes (TM and EPCR) were present in the same piglet. The CD39 multi-transgenic piglet was shown to express CD39 in endothelium via IF flow cytometry of isolated endothelial cells. The thirteen multi-transgenic TM pigs were all shown to express TM in endothelium via IF flow cytometry of isolated endothelial cells. Additionally, a subset of these multi-transgenic TM piglets were tested via immunohistochemistry (IHC) and showed IF expression of TM in organs (via cell smear) and/or endothelium of tail tissue (FIG. 4). Transcript expression of huTM via RTPCR was also determined (FIG. 5). The table below details genotype and TM protein expression data in these animals.

TABLE 1

Multi-transgenic pigs* produced with endothelial-specific anticoagulant transgenes.

| Piglet Generation and Genotype | | | Phenotype Data | | |
|---|---|---|---|---|---|
| Vector present in transgenic cell(s) used to generate piglets via NT | Piglet ID | Anticoagulant Genotype | Flow Cytometry (Endo), TM | IHC, TM | Organ Cell Smear, TM |
| pREV872, pREV873 | 424-01 | TM/EPCR | (+) | (+) tail | (+) ht, ki, li, lu |
| pREV872, pREV873 | 424-02 | TM/EPCR | (+) | (+) lu, li, ht, ao, ki | nd |
| pREV872, pREV873 | 424-03 | TM/EPCR | (+) | (+) tail | nd |
| pREV872 | 448-01 | TM | (+) | nd | (+) ht, ki, li, lu |
| pREV872 | 448-02 | TM | (+) | nd | (+) ht, ki, li, lu |
| pREV872 | 448-03 | TV | (+) | (+) lu, li, ht, ao | (+) ht, ki, li, lu |
| pREV872 | 448-04 | TM | (+) | nd | (+) ht, ki, li, lu |
| pREV872 | 448-05 | TV | (+) | nd | (+) ht, ki, li, lu |
| pREV872 | 450-01 | TV | (+) | nd | nd |
| pREV872 | 450-05 | TM | (+) | nd | nd |
| pREV872 | 450-06 | TM | (+) | (+)lu, li, ht, ao | (+) ht, ki, li, lu |
| pREV872 | 450-07 | TM | (+) | nd | nd |
| pREV872 | 451-03 | TM | (+) | nd | (+) ht, ki, li, lu |
| Donor Transgenic Cell(s) (used for NT) | Piglet ID | Anticoagulant Genotype | Flow Cytometry (Endo), CD39 | IHC, CD39 | Organ Cell Smear, CD39 |
| pREV859B, pREV861 | 440-04 | (Tie-2) CD39 | (+) | (+) ht, ki, li, lu, ao | nd |

* All pigs were additionally trangenic for the GTKO genetic modification and the CD46 transgenc. (Data not shown). This is the background genetics of the 183-6-6 donor cell line used to generate the multi-transgenic piglets with endothelial specific transgenes.

Figure 3:
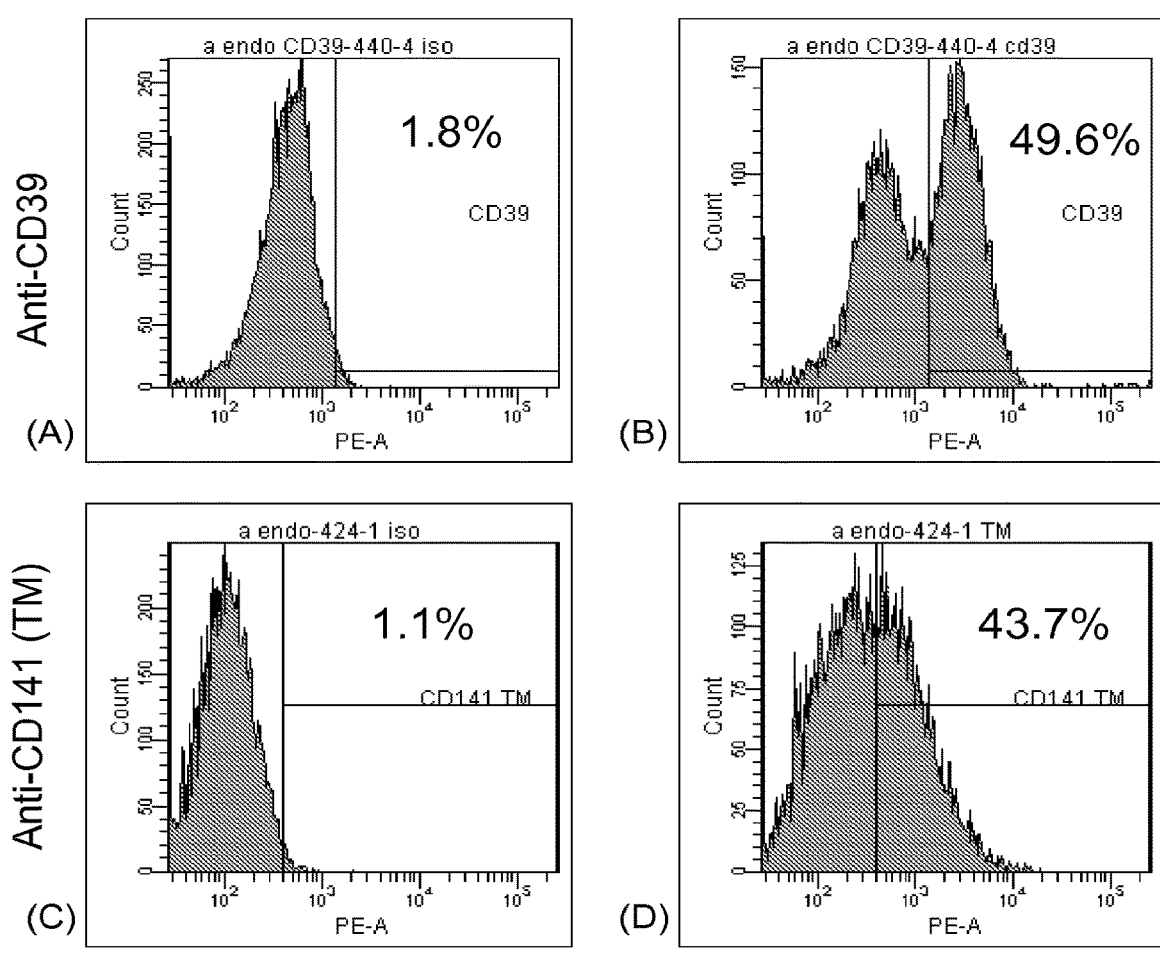
FIG. 3 shows flow cytometric analysis of transgenic protein expression in endothelial cells isolated from piglets 440-04 (CD39 transgenic) and 424-01 (TM transgenic), stained with anti-CD39 and anti-CD141 (TM), respectively. (A) shows isotype control binding to endothelial cells from piglet 440-4. (B) shows anti-human CD39 monoclonal antibody (mAb) binding to CD39 positive endothelial cells from 440-4. (C) shows isotype control binding to endothelial cells from piglet 424-01. (D) shows anti-human CD141 (TM) mAb binding to TM positive endothelial cells from 424-01.

FIG. 3 shows TM expression in endothelial cells isolated from piglet 424-01 determined via flow cytometry and CD39 expression in endothelial cells isolated from piglet 440-04. Samples of tail and organ tissues containing endothelium were collected from piglet 424-01 at approximately one month of age and phenotypically characterized for endothelial expression of TM by IF as described in Example 6.

FIG. 4 shows endothelial specific expression of TM determined via IHC of tail tissue from piglet 424-03.

FIG. 5 shows TM transcript expression by RTPCR in samples obtained from multi-transgenic piglets 448-01, 448-02, 448-03 and 450-06. TM copy number shown is the copy number of hTM present in 50 ng of cDNA.

The invention claimed is:

1. A transgenic animal comprising genetic modifications that result in:
   (i) lack of any expression of a functional alpha 1,3 galactosyltransferase (GTKO); and
   (ii) incorporation into the genome and expression of:
      a cytoprotective transgene that is ubiquitously expressed or is under the control of a constitutive promoter, wherein the cytoprotective transgene is selected from the group consisting of HO-1, FAT-1, A20, and soluble tumor necrosis factor-alpha (TNF-alpha) receptor; and
      an immunosuppressant transgene selected from the group consisting of cluster of differentiation 47 (CD47), and Class II transactivator-DN (CIITA-DN);
      one anticoagulant transgene under the control of an endothelial cell-specific promoter, wherein the at least one anticoagulant transgene is endothelial protein C receptor (EPCR) or thrombomodulin (TBM); wherein the EPCR or the TBM is expressed in an aorta, a lung, a kidney, a heart, a liver, an intestine, a stomach, or a spleen; and
      wherein the transgenic animal is a transgenic ungulate.

2. The transgenic animal of claim 1, wherein:
   (i) at least two transgenes are under the control of an endothelial cell-specific promoter; or
   (ii) the endothelial cell-specific promoter is ICAM-2 or Tie-2.

3. The transgenic animal of claim 2, further comprising one additional transgene, wherein the one additional transgene is a complement inhibitor transgene, and wherein the complement inhibitor transgene is selected from the group consisting of CD46, DAF (CD55), CD59, and CR1.

4. The transgenic animal of claim 3, wherein:
   (i) the anticoagulant transgene is thrombomodulin;
   (ii) the cytoprotective transgene is HO-1;
   (iii) the immunosuppressant transgene is CD47; and
   (iv) the complement inhibitor transgene is CD46 or CD55.

5. The transgenic animal of claim 3, wherein the anticoagulant transgene is EPCR, and
   (i) the complement inhibitor transgene is CD46 or CD59;
   (ii) the cytoprotective transgene is HO-1; and
   (iii) the immunosuppressant transgene is CD47.

6. The transgenic animal of claim 1, wherein the transgenic animal expresses two anticoagulant transgenes, and wherein the two anticoagulant transgenes are TBM and EPCR.

7. A cell isolated from the transgenic animal of claim 1.

8. An organ isolated from the transgenic animal of claim 1.

9. The organ of claim 8, wherein the organ is selected from the group consisting of heart, lung, liver, and kidney.

10. A tissue isolated from the transgenic animal of claim 1.

11. The tissue of claim 10, wherein the tissue is selected from the group consisting of vascular tissue, retinal tissue, and corneal tissue.

12. The tissue of claim 11, wherein the vascular tissue is a vascular graft.

13. A method for xenotransplantation comprising administering to a primate in need thereof organs, tissues, or cells isolated from the transgenic animal of claim 1.

14. The method of claim 13, wherein the primate is a human.

15. The method of claim 13, wherein:

(i) the organ is selected from the group consisting of heart, lung, liver, and kidney; or (ii) the tissue is selected from the group consisting of vascular tissue, retinal tissue and corneal tissue.

16. The transgenic animal of claim 1, wherein the transgenic animal comprises a nucleic acid sequence of SEQ ID NO: 7, SEQ ID NO: 10, or a complementary sequence thereof.

17. A transgenic porcine animal comprising genetic modifications that result in:

(i) lack of expression of functional alpha 1,3 galactosyl-transferase; and (ii) incorporation into the genome and expression of (a) two complement inhibitor transgenes, wherein the two complement inhibitors are CD46 and DAF; CD46 and CD59; or DAF and CD59, and wherein the complement inhibitors are ubiquitously expressed and are under the control of a constitutive promoter; and (b) two anticoagulant transgenes under the control of an endothelial cell-specific promoter, wherein the two anticoagulant transgenes are endothelial protein C receptor (EPCR), and thrombomodulin, and wherein the EPCR and the thrombomodulin are expressed in an aorta, a lung, a kidney, a heart, a liver, an intestine, a stomach, or a spleen; and (c) a CD47 transgene under the control of a constitutive promoter.

18. A transgenic porcine animal comprising genetic modifications that result in:

(i) lack of expression of functional alpha 1,3 galactosyl-transferase; and (ii) incorporation into the genome and expression of:

(a) one complement inhibitor transgene, wherein the complement inhibitor is selected from the group consisting of CD46 and DAF, and wherein the complement inhibitor is ubiquitously expressed and is under the control of a constitutive promoter;

(b) a CD47 transgene under the control of a constitutive promoter;

(c) a HO-1 transgene; and (d) one anticoagulant transgene under the control of an endothelial cell-specific promoter, wherein the anticoagulant transgene is selected from the group consisting of endothelial protein C receptor (EPCR) and thrombomodulin, and wherein the anticoagulant transgene is expressed in an aorta, a lung, a kidney, a heart, a liver, an intestine, a stomach, or a spleen.

\* \* \* \* \*

SEQUENCE LISTING

<160> NUMBER OF SEQ ID NOS: 12

<210> SEQ ID NO 1
<211> LENGTH: 21
<212> TYPE: DNA

```
<213> ORGANISM: Artificial Sequence
<220> FEATURE:
<223> OTHER INFORMATION: synthesized primer

<400> SEQUENCE: 1
agtatgggat tgtgctggat g                                              21

<210> SEQ ID NO 2
<211> LENGTH: 21
<212> TYPE: DNA
<213> ORGANISM: Artificial Sequence
<220> FEATURE:
<223> OTHER INFORMATION: synthesized primer

<400> SEQUENCE: 2
catagaggcg aaattgcaga g                                              21

<210> SEQ ID NO 3
<211> LENGTH: 585
<212> TYPE: DNA
<213> ORGANISM: Artificial Sequence
<220> FEATURE:
<223> OTHER INFORMATION: synthesized CD39L3/R3-dig probe

<400> SEQUENCE: 3
agtatgggat tgtgctggat gcgggttctt ctcacacaag tttatacatc tataagtggc     60
cagcagaaaa ggagaatgac acaggcgtgg tgcatcaagt agaagaatgc agggttaaag    120
gtcctggaat ctcaaaattt gttcagaaag taaatgaaat aggcatttac ctgactgatt    180
gcatggaaag agctagggaa gtgattccaa ggtcccagca ccaagagaca cccgtttacc    240
tgggagccac ggcaggcatg cggttgctca ggatggaaag tgaagagttg gcagacaggg    300
ttctggatgt ggtggagagg agcctcagca actacccctt tgacttccag ggtgccagga    360
tcattactgg ccaagaggaa ggtgcctatg gctggattac tatcaactat ctgctgggca    420
aattcagtca gaaaacaagg tggttcagca tagtcccata tgaaaccaat aatcaggaaa    480
cctttggagc tttggacctt gggggagcct ctacacaagt cacttttgta ccccaaaacc    540
agactatcga gtccccagat aatgctctgc aatttcgcct ctatg                    585

<210> SEQ ID NO 4
<211> LENGTH: 370
<212> TYPE: DNA
<213> ORGANISM: Artificial Sequence
<220> FEATURE:
<223> OTHER INFORMATION: synthesized Tie2L/R-dig probe

<400> SEQUENCE: 4
tggcagcttc tgcttgcttc gatcagctgc cagttaggta gcaacaaact tgggataagt     60
aacataagga gggtagttac aagcaacaag tcatcttaga acctctgcta agtcaagacc    120
cagaggcaag aagaagttgg gaattggttg gggaaaagta gggggctcca ccttgctggc    180
tggctgagtc acaagcaagg aatttcccca ccagacaacc cagcttttta acagaagccc    240
aggaacgcaa agctttaagc ccttctcttc gttttcctga tacaaagatg ctctttttgca    300 gtcaaagcag ccagagtcag ccccacacat atataaacag attagctcag gaatggaggc    360
ctgccctgaa                                                           370

<210> SEQ ID NO 5
<211> LENGTH: 20
<212> TYPE: DNA
<213> ORGANISM: Artificial Sequence
```

-continued

```
<220> FEATURE:
<223> OTHER INFORMATION: synthesized primer

<400> SEQUENCE: 5
actgcagcgt ggagaacggc                                                  20

<210> SEQ ID NO 6
<211> LENGTH: 20
<212> TYPE: DNA
<213> ORGANISM: Artificial Sequence
<220> FEATURE:
<223> OTHER INFORMATION: synthesized primer

<400> SEQUENCE: 6
ggtgttgggg tcgcagtcgg                                                  20

<210> SEQ ID NO 7
<211> LENGTH: 533
<212> TYPE: DNA
<213> ORGANISM: Artificial Sequence
<220> FEATURE:
<223> OTHER INFORMATION: synthesized TML/R-dig probe

<400> SEQUENCE: 7
actgcagcgt ggagaacggc ggctgcgagc acgcgtgcaa tgcgatccct ggggctcccc      60
gctgccagtg cccagccggc gccgccctgc aggcagacgg gcgctcctgc accgcatccg     120
cgacgcagtc ctgcaacgac ctctgcgagc acttctgcgt tcccaacccc gaccagccgg     180
gctcctactc gtgcatgtgc gagaccggct accggctggc ggccgaccaa caccggtgcg     240
aggacgtgga tgactgcata ctggagccca gtccgtgtcc gcagcgctgt gtcaacacac     300
agggtggctt cgagtgccac tgctacccta actacgacct ggtggacggc gagtgtgtgg     360
agcccgtgga cccgtgcttc agagccaact gcgagtacca gtgccagccc ctgaaccaaa     420
ctagctacct ctgcgtctgc gccgagggct tcgcgcccat tccccacgag ccgcacaggt     480
gccagatgtt ttgcaaccag actgcctgtc cagccgactg cgaccccaac acc            533

<210> SEQ ID NO 8
<211> LENGTH: 20
<212> TYPE: DNA
<213> ORGANISM: Artificial Sequence
<220> FEATURE:
<223> OTHER INFORMATION: synthesized primer

<400> SEQUENCE: 8
tcctgggctg tgagctgcct                                                  20

<210> SEQ ID NO 9
<211> LENGTH: 20
<212> TYPE: DNA
<213> ORGANISM: Artificial Sequence
<220> FEATURE:
<223> OTHER INFORMATION: synthesized primer

<400> SEQUENCE: 9
ccccctgaac ctgaaacata                                                  20

<210> SEQ ID NO 10
<211> LENGTH: 300
<212> TYPE: DNA
<213> ORGANISM: Artificial Sequence
<220> FEATURE:
<223> OTHER INFORMATION: synthesized EPCR3'/3' dig probe
```

-continued

```
<400> SEQUENCE: 10
tcctgggctg tgagctgcct cccgagggct ctagagccca tgtcttcttc gaagtggctg     60
tgaatgggag ctcctttgtg agtttccggc cggagagagc cttgtggcag gcagacaccc    120
aggtcacctc cggagtggtc accttcaccc tgcagcagct caatgcctac aaccgcactc    180
ggtatgaact gcgggaattc ctggaggaca cctgtgtgca gtatgtgcag aaacatattt    240
ccgcggaaaa cacgaaaggg agccaaacaa gccgctccta cacttcgctg gtcctgggcg    300

<210> SEQ ID NO 11
<211> LENGTH: 20
<212> TYPE: DNA
<213> ORGANISM: Artificial Sequence
<220> FEATURE:
<223> OTHER INFORMATION: synthesized primer

<400> SEQUENCE: 11
ttcagagcca actgcgagta                                                  20

<210> SEQ ID NO 12
<211> LENGTH: 20
<212> TYPE: DNA
<213> ORGANISM: Artificial Sequence
<220> FEATURE:
<223> OTHER INFORMATION: synthesized primer

<400> SEQUENCE: 12
aaccgtcgtc caggatgtag                                                  20
```